US010751291B2

(12) United States Patent
Fahmy et al.

(10) Patent No.: US 10,751,291 B2
(45) Date of Patent: Aug. 25, 2020

(54) NANOPARTICULATE COMPOSITIONS COMPRISING INTERFERON GAMMA AND LOSARTAN FOR IMMUNOTHERAPY

(71) Applicant: Yale University, New Haven, CT (US)

(72) Inventors: Tarek Fahmy, New Haven, CT (US); Brian Horsburgh, New Canaan, CT (US)

(73) Assignee: Yale University, New Haven, CT (US)

( * ) Notice: Subject to any disclaimer, the term of this patent is extended or adjusted under 35 U.S.C. 154(b) by 24 days.

(21) Appl. No.: 15/860,888

(22) Filed: Jan. 3, 2018

(65) Prior Publication Data

US 2018/0200196 A1  Jul. 19, 2018

Related U.S. Application Data

(63) Continuation-in-part of application No. 15/034,106, filed as application No. PCT/US2014/063545 on Oct. 31, 2014, now Pat. No. 9,884,026.

(60) Provisional application No. 61/899,080, filed on Nov. 1, 2013, provisional application No. 62/040,242, filed on Aug. 21, 2014.

(51) Int. Cl.
| | |
|---|---|
| *A61K 38/21* | (2006.01) |
| *A61K 9/51* | (2006.01) |
| *A61K 31/4178* | (2006.01) |
| *A61K 38/17* | (2006.01) |
| *A61K 35/30* | (2015.01) |
| *A61P 37/04* | (2006.01) |
| *A61P 35/00* | (2006.01) |
| *A61K 9/127* | (2006.01) |
| *A61K 31/704* | (2006.01) |
| *A61K 38/20* | (2006.01) |
| *A61K 45/06* | (2006.01) |
| *A61K 31/4439* | (2006.01) |
| *A61K 35/17* | (2015.01) |

(52) U.S. Cl.
CPC .......... *A61K 9/5153* (2013.01); *A61K 9/1271* (2013.01); *A61K 9/5146* (2013.01); *A61K 31/4178* (2013.01); *A61K 31/4439* (2013.01); *A61K 31/704* (2013.01); *A61K 35/17* (2013.01); *A61K 35/30* (2013.01); *A61K 38/1709* (2013.01); *A61K 38/208* (2013.01); *A61K 38/2013* (2013.01); *A61K 38/2086* (2013.01); *A61K 38/217* (2013.01); *A61K 45/06* (2013.01); *A61P 35/00* (2018.01); *A61P 37/04* (2018.01)

(58) Field of Classification Search
CPC .................................................... A61K 38/21
See application file for complete search history.

(56) References Cited

U.S. PATENT DOCUMENTS

| | | |
|---|---|---|
| 5,128,355 A | 7/1992 | Carini |
| 5,138,069 A | 8/1992 | Carini |
| 5,153,197 A | 10/1992 | Carini |
| 5,155,118 A | 10/1992 | Carini |
| 5,210,079 A | 5/1993 | Carini |
| 5,354,867 A | 10/1994 | Carini |
| 7,052,694 B2 | 5/2006 | Pease |
| 7,390,888 B2 | 6/2008 | Pease |
| 7,411,051 B2 | 8/2008 | Rosen |
| 8,114,845 B2 | 2/2012 | Langermann |
| 8,263,125 B2 | 9/2012 | Vaya |
| 8,609,089 B2 | 12/2013 | Langermann |
| 8,709,416 B2 | 4/2014 | Langermann |
| 2004/0071761 A1 | 4/2004 | Miller |
| 2006/0099203 A1 | 5/2006 | Pease |
| 2006/0110383 A1 | 5/2006 | Honjo |
| 2007/0014845 A1 | 1/2007 | Zhang |
| 2007/0166281 A1 | 7/2007 | Kosak |
| 2007/0219122 A1 | 9/2007 | Glazer |
| 2008/0050920 A1 | 2/2008 | Kawahara |
| 2008/0187595 A1 | 8/2008 | Jordan |

(Continued)

FOREIGN PATENT DOCUMENTS

| | | |
|---|---|---|
| CA | 2869748 | 10/2013 |
| EP | 2177230 A1 | 4/2010 |

(Continued)

OTHER PUBLICATIONS

Egilmez et al., "Cytokine immunotherapy of cancer with controlled release biodegradable microspheres in a human tumor xenograft/SCID mouse model," 1998, Cancer Immunol. Immunother. 46:21-24.

(Continued)

*Primary Examiner* — Prema M Mertz
(74) *Attorney, Agent, or Firm* — Riverside Law LLP

(57) ABSTRACT

Nanoparticulate compositions are disclosed. The nanoparticulate compositions typically include at least one, preferably two or more, active agent(s), one of which is an immunomodulatory compound, loaded into, attached to the surface of and/or enclosed within a delivery vehicle. The delivery vehicles can be nanolipogels including a polymeric core and a lipid shell or a biodegradable polymeric nanoparticle such as a PLGA nanoparticle. Typically, at least one of the active agents is an immunomodulator that increases an immune stimulatory response or decreases an immune suppressive response. In some embodiments, the particle includes both an immunomodulator that increases an immune stimulatory response and an immunomodulator that decreases an immune suppressive response. The particles can be decorated with a targeting moiety that improves delivery to a target cell. Methods of using the compositions to enhance an immune response and treat diseases such as cancer are also disclosed.

20 Claims, 16 Drawing Sheets

Specification includes a Sequence Listing.

(56) References Cited

U.S. PATENT DOCUMENTS

| | | | |
|---|---|---|---|
| 2009/0004213 A1 | 1/2009 | Singh | |
| 2011/0262406 A1 | 10/2011 | Del | |
| 2015/0064265 A1 | 3/2015 | Fahmy | |
| 2015/0118318 A1 | 4/2015 | Fahmy | |

FOREIGN PATENT DOCUMENTS

| | | |
|---|---|---|
| EP | 2389928 A2 | 11/2011 |
| EP | 2494960 A1 | 9/2012 |
| JP | 2008512350 | 4/2008 |
| RU | 2480201 C2 | 9/2009 |
| RU | 2473331 C2 | 5/2011 |
| WO | 9515746 A1 | 6/1995 |
| WO | 03099196 A2 | 12/2003 |
| WO | 2004004771 A1 | 1/2004 |
| WO | 2004056875 A1 | 7/2004 |
| WO | 2006080951 | 8/2006 |
| WO | 2006121168 A1 | 11/2006 |
| WO | 2006133396 A2 | 12/2006 |
| WO | 2007005754 A2 | 1/2007 |
| WO | 2007005874 A2 | 1/2007 |
| WO | 2007056539 A2 | 5/2007 |
| WO | 2007072286 A2 | 6/2007 |
| WO | 2008083174 A2 | 7/2008 |
| WO | 2009014708 A2 | 1/2009 |
| WO | 2009073533 A2 | 6/2009 |
| WO | 2010083337 A2 | 7/2010 |
| WO | 2012009611 A2 | 1/2012 |
| WO | 2012068531 A2 | 5/2012 |
| WO | 2013155487 | 10/2013 |
| WO | 2015066535 A1 | 5/2015 |

OTHER PUBLICATIONS

Yao et al., "Effective melanoma immunotherapy with interleukin-2 delivered by a novel polymeric nanoparticle," 2011, Mol Cancer Ther. 10(6):1082-92.
Khalil, et al., "Angiotensin II type 1 receptor antagonist (losarian) down-regulates transforming growth factor-beta in experimental acute pyelonephritis," 2000, J Urology, 164(1):186-91.
Park, et al., "Combination delivery TGF-2 inhibitor and IL-2 nanoscale liposomal polymeric gels enhances tumor immunotherapy," 2012, Nat Mater., 11(20):895-905.
Altincicek, et al., 'Identification of collagen IV derived danger/alarm signals in insect immunity by nanoLC-FTICR MS', 2009, Biol Chem., 390:1303-11.
Anderson and Shive, et al., "Biodegradation and biocompatibility of PLA and PLGA microspheres," 1997, Adv Drug Deliv Rev 28(1):5-24.
Argyo, et al., "Multifunctional Mesoporous Silica Nanoparticles as a Universal Platform for Drug Delivery", 2014, Chem. Mater., 26(1):435-451.
Aubert, et al., "Antigen-specific CD4 T-cell help rescues exhausted CD8 T cells during chronic viral infection," 2011, PNAS, 108:21182-7.
Barbe, et al., "Silica Particles: A Novel Drug-Delivery System," 2004, Advanced Materials, 16(21):1959-66.
Berger et al., "Phase I safety and pharmacokinetic study of CT-011, a humanized antibody interacting with PD-1, in patients with advanced hematologic malignancies," 2008, Clin. Cancer Res., 14:3044-51.
Blanco, et al., "Induction of dendritic cell differentiation by IFN-alpha in systemic lupus erythematosus," 2001, Science 294(5546)1540-3.
Blanco, et al., "Nanomedicine in cancer therapy: innovative trends and prospects," 2011, Cancer Sci, 102(7):1247-52.
Bonifaz, et al., 'Efficient targeting of protein antigen to the dendritic cell receptor DEC-205 in the steady state leads to antigen presentation on major histocompatibility complex class I products and peripheral CD8+ T cell tolerance', J. Exp. Med., 196(12)1627-38 (2002).
Bonifaz, et al., "In vivo targeting of antigens to maturing dendritic cells via the DEC-205 receptor improves T cell vaccination," 2004, J. Exp. Med., 199(6):815-24.
Braumuller, et al., "T-helper-1-cell cytokines drive cancer into senescence," 2012, Nature, 494:361-365.
Butte, et al., "Programmed death-1 ligand 1 interacts specifically with the B7-1 costimulatory molecule to inhibit T cell responses", Immunity, vol. 27, pp. 111-122, (2007).
Capurso, et al., 'Development of a nanoparticulate formulation of retinoic acid that suppresses Th17 cells and upregulates regulatory T cells', Self Nonself, 1:4:335-40 (2010).
Cavalli, et al., 'Solid lipid nanoparticies as carriers of hydrocortisone and progesterone complexes with beta-cyclodextrins', Intl J Pharma., 182:59-69 (1999).
Chen, et al. 'Evaluation of ion-exchange microspheres as carriers for the anticancer drug doxorubicin: in vitro studies.' J. Pharm. Pharmacol. 44(3):211-5 (1992).
Chen, et al., 'A facile construction strategy of stable lipid nanoparticles for drug delivery using a hydrogel-thickened microemulsion system', 2010, Nanotechnoiogy 21:015101.
Clarke, et al., 'Cancer stem cells—perspectives on current status and future directions: AACR Workshop on cancer stem cells', Cancer Res., 66:9339-9344 (2006).
Clawson, et al., 'Synthesis and characterization of lipid-polymer hybrid nanoparticles with pH-triggered PeG shedding', Langmuir, 27(17):10556-61 (2011).
Corradetti, et al., "Paracrine signaling events in embryonic stem cell renewal mediated by affinity targeted nanoparticles", Biomaterials, 33(28):6634-43 (2012).
Corthay, et al., "Primary antitumor immune response mediated by CD4+ T cells", Immunity, 22, 371-83 (2005).
Cubillos-Ruiz, et al., "Polyethylenimine-based siRNA nanocomplexes reprogram tumor-associated dendritic cells via TLR5 to elicit therapeutic antitumor immunity", J. Clin. Invest. 119(8): 2231-44 (2009).
Curie!, 'Regulatory T cells and treatment of cancer', Curr. Opin. Immunol., 20(2):241-6 (2008).
DaCosta, et al., 'SB-505124 is a selective inhibitor of transforming growth factor-beta type I receptors ALK4, ALK5, and ALK7', Mol Pharmacol. 65:744-52 (2004).
Dalerba, et al., 'Cancer stem cells: models and concepts', Annu. Rev. Med., 58:267-84 (2007).
Danhier, et al., 'PLGA-based nanoparticles: an overview of biomedical applications', J. Control Release, 161(2):505-22 (2012).
De Miguel, et al., "Proofs of the structure of lipid coated nanoparticles (SMBV) used as drug carriers", Pharma Res., 17(7):817-24 (2000).
De Rezende, et al., 'Regulatory T cell as a target for cancer therapy', Arch. Immunol. Ther. Exp., 58(3):179-90 (2010).
Demento, et al., 'Inflammasome-activating nanoparticles as modular systems for optimizing vaccine efficacy', Vaccine, 27(23):3013-21 (2009).
Demento, et al., "Role of sustained antigen release from nanoparticle vaccines in shaping the T cell memory phenotype", Biomaterials, 33(19):4957-64 (2012).
Diop-Frimpong, et al., 'Losartan inhibits collagen I synthesis and improves the distribution and efficacy of nanotherapeutics in tumors', PNAS, 108(7):2909-14 (2011).
Elamanchili, et al., 'Characterization of poly(D,L-lactic-co-glycolic acid) based nanoparticulate system for enhanced delivery of antigens to dendritic cells', Vaccine, 22(19):2406-12 (2004).
Elbarbry, et al., 'Liquid chromatographic determination of mycophenolic acid and its metabolites in human kidney transplant plasma: pharmacokinetic application', J Chromatogr B Analyt Technol Biomed Life Sci, 859(2):276-81(2007).
Erbe, et al., 'Small molecule ligands define a binding site on the immune regulatory protein B7.1.', J. Biol. Chem., 277:7363-8 (2002).
Fahmy, et al., 'Targeted for drug delivery', Materials Today, 8(8):18-26 (2005).
Farag, et al. 'Rate of release of organic carboxylic acids from ion exchange resins' J. Pharm. Sci. 77(10):872-5(1988).
Filler, et al., 'Random pharmacokinetic profiles of EC-MPS in children with autoimmune disease', Pediatric Rheumatol., 8:1 (2010).

(56) References Cited

OTHER PUBLICATIONS

Flavell, et al., The polarization of immune cells in the tumour enviroment by TGFbeta, Nat Rev Immunol., 10(8):1-27 (2010).
Freeman, "Structures of PD-1 with its ligands: sideways and dancing cheek to cheek", PNAS, 105:10275-6 (2008).
Frey, et al., 'Signaling defects in anti-tumor T cells', Immunol. Rev., 222:192-205 (2008).
Ginzler, et al., 'Mycophenolate mofetil or intravenous cyclophosphamide for lupus nephritis', N Engl J Med, 353(21):2219-28 (2005).
Gorelik, et al., 'Immune-mediated eradication of tumors through the blockade of transforming growth factor-beta signaling in T cells', Nat Med., 7(10):1118-22 (2001).
Grell, et al., 'The transmembrane form of tumor necrosis factor is the prime activating ligand of the 80 kDa tumor necrosis factor receptor', Cell, 83:793-802 (1995).
Guo, et al., 'Losartan downregulates the expression of transforming growth factor beta type I and type II receptors in kidney of diabetic rat.', Zhonghua Nei Ke Za Zhi, 42:403-8 (2003).
Hamidi, et al., 'Hydrogel nanoparticles in drug delivery', Adv Drug Deily Rev., 60(15):1638-49 (2008).
Hawiger, et al., "Dendritic cells induce peripheral T cell unresponsiveness under steady state conditions in vivo", J. Exp. Med., 194(6):769-79 (2001).
Honeychurch, et al., 'Anti-CD40 monoclonal antibody therapy in combination with irradiation results in a CD8 T-cell-dependent immunity to B-cell lymphoma', Blood, 102:1449-1457 (2003).
Hong, 'Lipid-hydrogel nanoparticles synthesis methods and characterization',Theses from DRUM, pp. 1-91 (2009).
Hu, et al., "Reaction parameters of targeted gene repair in mammalian cells", Mol. Biotech., 29:197-210 (2005).
Hunder, et al., 'Treatment of metastatic melanoma with autologous CD4+ T cells against NY-ESO-1', NEJM, 358:2698-2703 (2008).
Jain, et al., "Nanolipobeads bases drug delivery system for effective management of peptic ulcer", Intl J Curr Pharmaceutical Res., 3(2):141-9 (2011).
Jhunjhunwala, et al., 'Controlled release formulations of IL-2, TGF-21 and rapamycin for the induction of regulatory T cells', J Cont Rel., 159(1):78-84 (2012).
Jonsson, et al., 'Inosine monophosphate dehydrogenase (IMPDH) inhibition in vitro suppresses lymphocyte proliferation and the production of immunoglobulins, autoantibodies and cytokines in splenocytes from MRLIpr/lpr mice', Clin Exp Immunol, 124(3):486-91 (2001).
Jonsson, et al., "Mycophenolic acid inhibits inosine 5'-monophosphate dehydrogenase and suppresses immunoglobulin and cytokine production of B cells", Int Immunopharmacol, 3(1):31-7 (2003).
Joshi, et al., 'Targeting tumor antigens to dendritic cells using particulate carriers', J. Control Release, 161(1):25-37 (2012).
Kahn, 'CD4+ T cell clones specific for the human p97 melanoma-associated antigen can eradicate pulmonary metastases from a murine tumor expressing the p97 antigen', J Immunol, 146:3235-41 (1991).
Kamen, et al., "Mycophenolic acid differentially impacts B cell function depending on the stage of differentiation", J Immunol, 187(7):3603-12 (2011).
Kong, et al., 'Combination therapy with losartan and piog;otazone additively reduces renal oxidative and nitrative stress induced by chronic high fat, sucrose, and sodium intake', Oxid Med Cell. Longev, doi: 10.1155/2012/856085 (2012). (10 pages).
Lagaraine, et al., 'Induction of human CD4+ regulatory T cells by mycophenolic acid-treated dendritic cells', J Leukoc Biol, 84(4):1057-64 (2008).
Lagaraine, et al., 'Mycophenolic acid-treated human dendritic cells have a mature migratory phenotype and inhibit allogeneic responses via direct and indirect pathways', Int Immunol, 17(4):351-63 (2005).
Lazar-Molnar, et al., 'Crystal structure of the complex between programmed death-1 (PD-1) and its ligand PD-L2', PNAS, 105:10483-8 (2008).
Lee, et al., "Induction and maintenance therapy for lupus nephritis: a systematic review and meta-analysis", Lupus, 19(6):703-10 (2010).

Lipsky, 'Mycophenolate mofetil', Lancet, 348:L1357-9 (1996).
Look, et al., 'Application of nanotechnologies for improved immune response against infectious diseases in the developing world', Adv Drug Deilv Rev, 62(4-5):378-93 (2010).
Look, et al., 'Nanogel-based delivery of mycophenolic acid ameliorates systemic lupus erythematosus in mice', J. Clin Invest., 123(4):1741-9 (2013).
Look, et al., 'The nanomaterial-dependent modulation of dendritic cells and its potential influence on therapeutic immunosuppression in lupus', Biomaterials, 35(3):1089-95 (2014).
Losartan, from Wikipedia encyclopedia, https://en.wikipedia.org/wiki/Losartan, 4 pages, retrieved from the internet Oct. 22, 2013.
Luchini, et al. 'Smart hydrogel nanoparticles for serum cancer biomarkers harvesting', AACR annual meeting, Apr. 14-18, Los Angles CA, 2007. (1 page).
Lui, et al., 'Effect of mycophenolate mofetil on severity of nephritis and nitric oxide production in lupus-prone MRL/lpr mice', Lupus, 11(7):411-8 (2002).
Lund, et al., 'Toll-like receptor 9-mediated recognition of Herpes simplex virus-2 by plasmacytoid dendritic cells', J Exp Med, 198(3):513-20 (2003).
Ma et al., 'The comparison of different daidzein-PLGA nanoparticles in increasing its oral bioavailability', Int J Nanomed., 7:559-570 (2012).
Matreya, '1,2-Distearoylphosphatidylethanolamine-methyl-polyethyleneglycol conjugate-200(Na+salt)', http://www.matreya.com/ProductInfo.aspx?peoductid=1439, 2 pages, retrieved from the Internet Mar. 30, 2012. (2 pages).
Maurer, et al., 'Developments in liposomal drug delivery systems', Expert Opin Biol Ther., 1(6):923-47 (2001).
Mehling, et al., Mycophenolate mofetil impairs the maturation and function of murine dendritic cells, J Immunol, 165(5):2374-81 (2000).
Monneaux, et al., 'Molecular therapies for systemic lupus erythematosus: clinical trials and future prospects', Arthritis Res Ther, 11(3):234 (2009).
Moroni, et al., 'A randomized pilot trial comparing cyclosporine and azathioprine for maintenance therapy in diffuse lupus nephritis over four years', Olin J Am Soc Nephrol, 1(5):925-32 (2006).
Mougiakakos, et al., 'Regulatory T cells in cancer', Adv Cancer Res, 107:57-117 (2010).
Mura, et al., "Development of a new delivery system consisting in drug-in cyclodextrin-in PLGA nanoparticles", J Microencapsulation, 27(6):479-86 (2010).
Murphy, et al., "Targeted Nanogels: A Versatile Platform for Drug Delivery to Tumors", Mole Cancer Therapeutics, 10(6):972-82 (2011).
Nagaraj, et al., 'Anti-inflammatory triterpenoid blocks immune suppressive function of MDSCs and improves immune response in cancer', Clin Cancer Res., 16(6):1812-23 (2010).
Navarra, et al., 'Efficacy and safety of belimumab in patients with active systemic lupus erythematosus: a randomised, placebo-controlled, phase 3 trial', Lancet, 377(9767):721-31 (2011).
Nesbeth, et al., 'CD4+ T cells elicit host immune responses to MHC class II-negative ovarian cancer through CCL5 secretion and CD40-mediated licensing of dendritic cells' , J Immunol., 184:5654-62 (2010).
Olsen, et al., 'Genomic sequence correction by single-stranded DNA oligonucleotides: role of DNA synthesis and chemical modifications of the oligonucleotide ends'. J. Gene Med., 7:1534-44 (2005).
Opal and DePalo, 'Anti-inflammatory cytokines', Chest, 117(4):1162-72 (2000).
Park, 'Rationally engineered nanoparticles for therapeutic modulation of transforming growth factor beta signaling', Dissertation confidentially presented May 2011, not publically available other than abstract from ProQuest UMI No. 3467563, pp. 1-25 only distributed to one party prior to filing of U.S. Appl. No. 61/623,486 on Apr. 12, 2012.
Patel,et al., 'Review on hydrogel nanoparticles in drug delivery' AJPTR, 1(3):19-38 (2011).

(56) References Cited

OTHER PUBLICATIONS

Peer, et al., "Systemic leukocyte-directed siRNA delivery revealing cyclin D1 as an anti-inflammatory target", Science, 319:627-30 (2008).
Perez-Diez, 'CD4 cells can be more efficient at tumor rejection than CD8 cells' Blood, 109:5346-54 (2007).
Petersen, et al., 'Accumulation in tumor tissue of adoptively transferred T cells: A comparison between intravenous and intraperitoneal injection', J Immunother 29, 241-9 (2006).
Punyamoonwongsa and Tighe, 'A smart hydrogel-based system for controlled drug release', Chiang Mai J Sci., 32(3):471-8 (2005).
Quemeneur, et al., Mycophenolic acid inhibits IL-2-dependent T cell proliferation, but not IL-2-dependent survival and sensitization to apoptosis, J Immunol, 169(5):2747-55 (2002).
Rahman, et al., 'Systemic lupus erythematosus', N Engl J Med, 358(9):929-39 (2008).
Ramos, et al., 'Modulation of autoantibody production by mycophenolate mofetil: effects on the development of SLE in (NZB x NZVV)F1 mice', Nephrol Dial Transplant, 18(5):878-83 (2003).
Rehman, et al., "Angiotensin Type 2 receptor agonist compound 21 reduces vascular injury and myocardial fibrosis in stroke-prone spontaneously hypertensive rats", Hypertension, 59(2):291-9 (2012).
Ronnblom, et al., 'Cytokines as therapeutic targets in SLE', Nat Rev Rheumatol, 6(6):339-47 (2010).
Ruoslahti, et al., "RGD and other recognition sequences for integrins", Annu. Rev. Cell Dev. Biol., 12:697-715 (1996).
Ruoslahti, et al., 'Specialization of tumour vasculature', Nat. Rev. Cancer, 2:83-90 (2002).
Sammartino, et al., 'Anti-GBM disease following CTLA4 blockade in a patient with metastatic melanoma', Clinical Kidney J, 3(2):135-137 (2010).
Samstein, et al., 'The use of deoxycholic acid to enhance the oral bioavailability of biodegradable nanoparticles', Biomaterials., 29(6):703-8 (2008).
Sawhney, et al., 'Bioerodible hydrogels based on photopolymerized poly(ethylene glycol)-co-poly(.alpha.-hydroxy acid) diacrylate macromers', Macromolecules, 26:581-7 (1993).
Schneider, et al., 'Conversion of membrane-bound Fas(CD95) ligand to its soluble form is associated with downregulation of its proapoptotic activity and loss of liver toxicity', J. Exp. Med.,187:1205-121 (1998).
Scindia, et al., 'Anti-alpha8 integrin immunoliposomes in glomeruli of lupus-susceptible mice: a novel system for delivery of therapeutic agents to the renal glomerulus in systemic lupus erythematosus', Arthritis Rheum, 58(12):3884-91 (2008).
Selleckchem,'TGF-beta/Smad Inhibitors' http://www.selleckchem.com/products/sb-505124.html, 4 pages, Retrieved from the internet Oct. 22, 2013.
Serkova, et al., 'Renal inflammation: targeted iron oxide nanoparticles for molecular MR imaging in mice', Radiology, 255(2):517-26 (2010).
Sfikakis, et al., 'Rituximab anti-B-cell therapy in systemic lupus erythematosus: pointing to the future', Curr Opin Rheumatol, 17(5):550-7 (2005).
Shafer-Weaver, et al., 'Immunity to murine prostatic tumors: continuous provision of T-cell help prevents CD8 T-cell tolerance and activates tumor-infiltrating dendritic cells', Cancer Research, 69:6256-64 (2009).
Shirali, et al., 'Nanoparticle delivery of mycophenolic acid upregulates PD-L1 on dendritic cells to prolong murine allograft survival', Am J Transplant, 11(12):2582-92 (2011).

Shlomchik, et al., 'From T to B and back again: positive feedback in systemic autoimmune disease', Nat Rev Immunol, 1(2):147-53 (2001).
Steenblock, et al., 'A Comprehensive Platform for Ex Vivo T-cell Expansion Based on Biodegradable Polymeric Artificial Antigen-presenting Cells', Mole Therapy, 16(4):765-72 (2008).
Tanaka, et al., "Downregulation of Fas ligand by shedding", Nat. Med., 4: 31-36 (1998).
Teichmann, et al., 'Dendritic cells in lupus are not required for activation of T and B cells but promote their expansion, resulting in tissue damage', Immunity, 33(6):967-78 (2010).
Torchilin, et al., 'Multifunctional nanocarriers', Adv Drug Deliv Rev., 58(14):1532-55 (2006).
Trevelyan, et al., 'Effect of enalapril and losartan on cytokines in patients with stable angina pectoris awaiting coronary artery bypass grafting and their interaction with polymorphisms in the interleukin-6 gene', Am J Caridol., 94(5):564-9 (2004).
Triantafyllopoulou, et al., 'Proliferative lesions and metalloproteinase activity in murine lupus nephritis mediated by type I interferons and macrophages', PNAS, 107(7):3012-7 (2010).
Vonderheide, "Prospect of targeting the CD40 pathway for cancer therapy", Clin Cancer Res, 13(4):1083-1088 (2007).
Wadia, et al., "Mycophenolic acid inhibits maturation and function of human dendritic cells and B cells", Hum Immunol, 70(9):692-700 (2009).
Wang, et al., 'Immune suppression by tumor-specific CD4+ regulatory T-cells in cancer', Semin Cancer Biol., 16:73-9 (2006).
Willimsky, et al., 'The adaptive immune response to sporadic cancer', Immunol. Rev., 220:102-12 (2007).
Wofsy, et al., 'Reversal of advanced murine lupus in NZB/NZW F1 mice by treatment with monoclonal antibody to L314', J Immunol, 138(10):3247-53 (1987).
Wofsy, et al., 'Successful treatment of autoimmunity in NZB/NZW F1 mice with monoclonal antibody to L3T4', J Exp Med, 161(2):378-91 (1985).
Wong, et al., 'Simultaneous delivery of doxorubicin and GG918 (Elacridar) by new polymer-lipid hybrid nanoparticles (PLN) for enhanced treatment of multidrug-resistant breast cancer', J Cont Rel., 116:275-84 (2006).
Xiao, et al., 'Recent advances in PEG-PLA block copolymer nanoparticles', Int J Nanomed., 5:1057-65 (2010).
Yang, et al., 'Preparation of gel-core-solid lipid nanoparticle: A novel way to improve the encapsulation of protein and peptide', Chem Pharm Bull., 58(9):1195-202 (2010).
Yoshida, et al., 'Effect of poly(lactic-co-glycolic acid) contact on maturation of murine bone marrow-derived dendritic cells', J Biomed Mater Res A, 80(1):7-12 (2007).
Zhang, et al., 'Self-assembled lipid-polymer hubrid nanoparticles: A robust drug delivery platform', ACS Nano, 2(8):1696-1702 (2008).
Ziai, et al., 'Renal allograft protection with losartan in Fisher Lewis rats: Hemodynamics, macrophages, and cytokines', Kidney Int., 57(6):2618-25 (2000).
Xiang, S.D. et al., 'Promising particle-based vaccines in cancer therapy', Expert Review of Vaccines. 2008, vol. 7, No. 7, pp. 1103-1119.
Health Day, 'Blood pressure drug might boost chemo success, mouse study suggests', http://consumer.healthday.com/circulatory-system-information-7/blood-pres- sure-news-70/blood-pressure-drug-might-boost-chemo-success-mouse-study-sug- gests-680633.html,Retrieved from the internet Oct. 2, 2013. (1 page).
Hoare, et al., 'Hydrogels in drug delivery: Process and challenges', Polymer, 49:1993-2007 (2008).
Rosenholm, et al., Multifunctional Mesoporous Silica Nanoparticles for Combined Therapeutic, Diagnostic and Targeted Action in Cancer Treatment, 2011, Curr Drug Targets 12:1166-86.

NANOPARTICULATE COMPOSITIONS COMPRISING INTERFERON GAMMA AND LOSARTAN FOR IMMUNOTHERAPY

CROSS-REFERENCE TO RELATED APPLICATIONS

The present application is a continuation of U.S. patent application Ser. No. 15/034,106, filed on May 3, 2016, which is a national phase application filed under 35 U.S.C. § 371 claiming benefit to International Patent Application No. PCT/US2014/063545, filed Oct. 31, 2014 which is entitled to priority under to U.S. Provisional Application No. 61/899,080, filed on Nov. 1, 2013 and U.S. Provisional Application No. 62/040,242, filed Aug. 21, 2014, each of which applications is incorporated herein by reference in their entireties.

REFERENCE TO SEQUENCE LISTING

The Sequence Listing submitted Apr. 2, 2018, as a text file named "47162-5233-01-US606191 Seq List_ST25.txt," is hereby incorporated by reference.

FIELD OF THE INVENTION

The invention is generally directed to nanoparticulate compositions and methods of use thereof for immunotherapy.

BACKGROUND OF THE INVENTION

Although efficacy of therapeutic treatments is dependent upon the mechanism of action of the agent used, other factors can also be important for eliciting an optimal response. For example, dosage and timing of administration relative to onset of disease as well as a number of complex issues involving pharmacokinetic and pharmacodynamic characteristics can be important considerations.

Over the years a variety of studies have been carried out with an array of therapeutic agents in an effort to establish optimal strategies for drug delivery. Drug regimens for many different types of diseases have evolved into combination therapies. For example, in some instances, combinations are used to improve efficacy by (1) combining drugs that have the same or different disease targets; (2) combining two drugs where the activity of the two in combination is greater than the sum of the activities of each alone; and (3) a combination of two drugs wherein one drugs one acts directly on the disease state, while the other improves the subject's symptoms indirectly. However, such disparate drugs with disparate roles in disease treatment often differ dramatically with respect to chemical nature, and drug delivery issues in combination therapy can be very challenging.

Therefore, it is an object of the invention to provide compositions and methods for improved drug delivery and disease treatment.

It is another object of the invention to provide compositions and methods for improving delivery and efficacy of an active agent to a target cell.

It is a further object of the invention to provide compositions and methods for improving delivery and efficacy of combination therapies including at least two active agents.

It is yet a further object of the invention to provide specific combination therapies to induce or enhance an immune stimulatory response in a subject in need thereof.

SUMMARY OF THE INVENTION

Nanoparticulate compositions are disclosed. The nanoparticulate compositions typically including one, preferably two or more active agents loaded into, attached to the surface of, and/or enclosed within a delivery vehicle. The delivery vehicles can be nanolipogels including a polymeric core and a lipid shell or a biodegradable polymeric nanoparticle such as a PLGA nanoparticle. The active agents can be therapeutic or diagnostic agents, targeting moieties, antigens, or adjuvants. The relative concentrations of each of the two or more active agents and their location on or within the delivery vehicle can be manipulated during manufacture of the compositions to adapt a preferred dosage and presentation that will be received by the target cell. Loading of two or more active agents into or onto the same delivery vehicle allows the two or more active agents to be presented to the target cell simultaneously or in an otherwise predetermined order.

In the most preferred embodiments, the nanoparticulate composition includes at least one immunomodulator. The immunomodulator can be an agent that increases or enhances an immune stimulatory response, for example, an agent that enhances a T cell response, increases T cell activity, increases T cell proliferation, reduces a T cell inhibitory signal, enhances production of cytokines, stimulates T cell differentiation or effector functions, promotes survival of T cells or any combination thereof. Exemplary agents that increase or enhance an immune stimulatory response include, but are not limited to, cytokines and chemokines such as Interleukin-2 (IL-2) and Interferon γ (IFNγ).

The immunomodulator can be an agent that decreases or inhibits an immune suppressive response, for example, an agent that depletes regulatory T cells (Treg); blocks Treg differentiation, trafficking, effector functions, or a combination thereof; raises effector cell suppression threshold, or any combination thereof. Exemplary agents that decrease or inhibit an immune suppressive response include, but are not limited to, TGF-β inhibitors such as SB505124 or losartan.

The compositions can include a targeting moiety. Preferred targeting moieties include RGD peptide, CD40 agonist, T cell receptor that recognizes p53 antigen, and IL-15/IL-15Rα complex.

Specific combinations of active agents are also disclosed. For example, in some embodiments, the delivery vehicle is loaded with or decorated with IL-2 or IFNγ in combination with losartan. In other embodiments, the delivery vehicle is loaded with IL-2 or IFNγ and decorated with a targeting moiety such as RGD peptide or an anti-CD40 antibody or antigen binding fragment thereof.

Artificial dendritic cells and compositions that mimic dendritic cells are also disclosed. In a particular embodiment, an artificial dendritic cell is composed of a nanolipogel with a polymeric core and a lipid shell or a biodegradable polymeric nanoparticle. The nanolipogel or polymeric nanoparticle, for example a PLGA nanoparticle, is decorated with an IL-15/IL-15Rα complex. The artificial dendritic cell can be loaded with one or more additional active agents such as IL-2, IFNγ, losartan, SB505124, or any combination thereof.

Methods of stimulating or enhancing an immune response in a subject and treating a subject for cancer are also disclosed. Typically, the methods include administering to the subject an effective amount of the nanoparticulate composition to increase an immune response, destroy cancer cells, interfere with cancer growth and/or metastasis, and/or reduce one or more adverse consequences and/or sequelae of the cancer. This mode of action can be therapeutic or prophylactic. As such, enhancement, stimulation or interference of the immune response using administered particles is useful for both vaccine development with known antigens or suppression of autoimmune disorders.

Methods of treating subjects in need thereof including administering the subject a nanoparticulate composition including a delivery vehicle such as a nanolipogel or a polymeric particle having one or more active agents loaded into, onto, or otherwise associated therewith in combination with administering the subject an additional active agent are also provided. The nanoparticulate composition and the additional active agent can be administered in a single pharmaceutical composition or separately in different pharmaceutical compositions. In a particularly preferred embodiment, the nanoparticulate composition includes nanolipogels or other polymeric particles having a proinflammatory cytokine (e.g., IL-2) and/or a TGFβ inhibitor (e.g., losartan) and the additional active agent is an immune modulator or a chemotherapeutic agent. In a particularly preferred embodiment the one or more active agents is an immune response stimulator or enhancer such as a PD-1 antagonist (e.g., antagonistic anti-PD1 antibody, anti-B7-H1 antibody, etc.), or a CTLA4 antagonist (e.g., antagonistic anti-CTLA4 antibody), or even more preferably a combination thereof. In another preferred embodiment, the additional active agent is a chemotherapeutic agent, for example doxorubicin.

The method can be used to treat a subject in whom an enhanced immune response (e.g, an increase or induction of T cell responses such as T cell proliferation or activation) is desired. Exemplary subjects include those with cancer or an infectious disease. The immune response (e.g., increased or induced T cell response) can be against a cancer or disease antigen. The immune response can be effective to treat the cancer or infection. In some embodiments, the immune response is against cancerous and/or disease infected cells and can reduce one or more symptoms of the cancer and/or disease (e.g., tumor burden, tumor progression, disease progression, etc.). Treatment regimens are also provided.

DETAILED DESCRIPTION OF THE INVENTION

I. Definitions

Figure 1A:
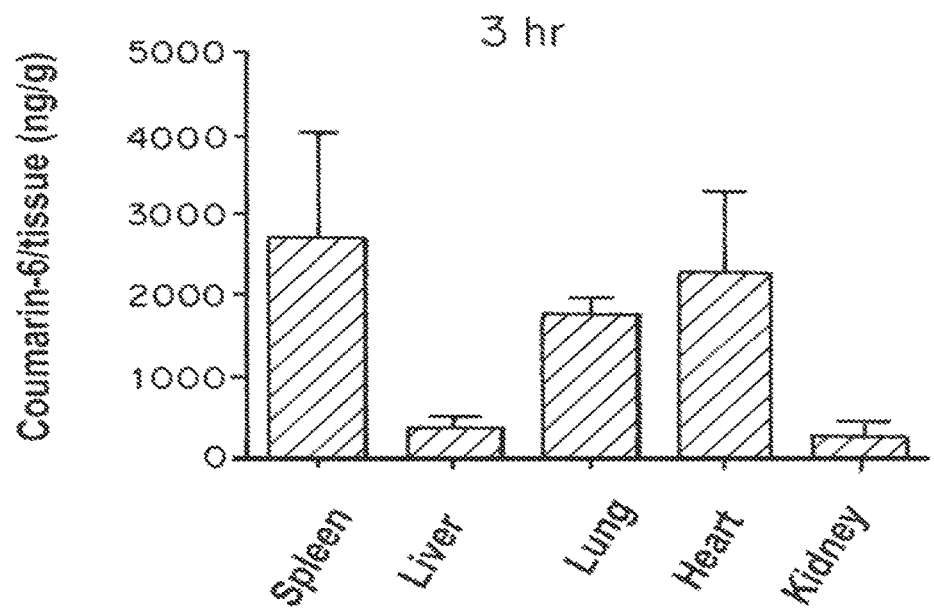
FIG. 1A is a bar graph showing the distribution of coumarin-6/tissue (ng/g) in the spleen, liver, lung, heart, and kidney of mice three (3) hours after injection with coumarin-6-loaded PLGA nanoparticles.

"Nanolipogel," as used herein, refers to a core-shell nanoparticle having a polymer matrix core, which can contain a host molecule, within a liposomal shell, which may be unilamellar or bilamellar, optionally crosslinked.

"Host molecule," as used herein, refers to a molecule or material which reversibly associates with an active agent to form a complex. In particular embodiments, the host is a molecule that forms an inclusion complex with an active agent. Inclusion complexes are formed when an active agent (i.e., the guest) or portion of an active agent inserts into a cavity of another molecule, group of molecules, or material (i.e., the host). The host may be a small molecule, an oligomer, a polymer, or combinations thereof. Exemplary hosts include polysaccharides such as amyloses, cyclodextrins, and other cyclic or helical compounds containing a plurality of aldose rings, for example, compounds formed through 1,4 and 1,6 bonding of monosaccharides (such as glucose, fructose, and galactose) and disaccharides (such as sucrose, maltose, and lactose). Other exemplary host compounds include cryptands, cryptophanes, cavitands, crown ethers, dendrimers, ion-exchange resins, calixarenes, valinomycins, nigericins, catenanes, polycatenanes, carcerands, cucurbiturils, and spherands.

"Small molecule," as used herein, refers to molecules with a molecular weight of less than about 2000 g/mol, more preferably less than about 1500 g/mol, most preferably less than about 1200 g/mol.

"Hydrogel," as used herein, refers to a water-swellable polymeric matrix formed from a three-dimensional network of macromolecules held together by covalent or non-covalent crosslinks, that can absorb a substantial amount of water (by weight) to form a gel.

"Nanoparticle", as used herein, generally refers to a particle having a diameter from about 10 nm up to, but not including, about 1 micron, preferably from 100 nm to about 1 micron. The particles can have any shape. Nanoparticles having a spherical shape are generally referred to as "nanospheres".

"Molecular weight" as used herein, generally refers to the relative average chain length of the bulk polymer, unless otherwise specified. In practice, molecular weight can be estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

"Mean particle size" as used herein, generally refers to the statistical mean particle size (diameter) of the particles in a population of particles. The diameter of an essentially spherical particle may refer to the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering.

"Monodisperse" and "homogeneous size distribution", are used interchangeably herein and describe a population of nanoparticles or microparticles where all of the particles are the same or nearly the same size. As used herein, a monodisperse distribution refers to particle distributions in which 90% of the distribution lies within 15% of the median particle size, more preferably within 10% of the median particle size, most preferably within 5% of the median particle size.

"PD-1 antagonist" as used herein means any molecule that attenuates inhibitory signal transduction mediated by PD-1, found on the surface of T cells, B cells, natural killer (NK) cells, monocytes, DC, and macrophages. Such an antagonist includes a molecule that disrupts any inhibitory signal generated by a PD-1 molecule on a T cell. Therefore, PD-1 antagonist can be a molecule that inhibits, reduces, abolishes or otherwise reduces inhibitory signal transduction through the PD-1 receptor signaling pathway. Such decrease may result where: (i) the PD-1 antagonist binds to a PD-1 receptor without triggering signal transduction, to reduce or block inhibitory signal transduction; (ii) the PD-1 antagonist binds to a ligand (e.g. an agonist) of the PD-1 receptor, preventing its binding thereto (for example, where said agonist is B7-H1); (iii) the PD-1 antagonist binds to, or otherwise inhibits the activity of, a molecule that is part of a regulatory chain that, when not inhibited, has the result of stimulating or otherwise facilitating PD-1 inhibitory signal transduction; or (iv) the PD-1 antagonist inhibits expression of a PD-1 receptor or expression ligand thereof, especially by reducing or abolishing expression of one or more genes encoding PD-1 or one or more of its natural ligands. Thus, a PD-1 antagonist can be a molecule that affects a decrease in PD-1 inhibitory signal transduction, thereby increasing T cell response to one or more antigens.

"CTLA4 antagonist" as used herein means a compound that reduces CTLA4-mediated inhibition of T cell reactions. For example, in an T cell, CTLA4 delivers an inhibitory impulse upon binding of B7 ligands, such B7-1 and B7-2. A CTLA4 antagonist is one that disrupts binding of said ligands to CTLA4 on activated T cells.

II. Nanoparticulate Compositions

Nanoparticulate compositions including one or more active agents each loaded into, attached to the surface of, and/or enclosed within a delivery vehicle, are disclosed. The nanoparticulate compositions offer a number of advantages over delivering the active agent or agents to the target cells in solution. For example, the nanoparticulate compositions present a localized concentration of the one or more active agents on or in a nanoparticle leading to increased avidity when the nanoparticle encounters the target cells. The nanoparticulate compositions can also serve as a depot of active agent with tunable release kinetics that can extend over several days to prolong effective systemic half-life and efficacy of the agent or agents.

Typically, two or more active agents are loaded into, attached to the surface of, and/or enclosed within a delivery vehicle. The relative concentrations of each of the two or more active agents and their location on or within the delivery vehicle can be manipulated during manufacture of the compositions to adapt a preferred dosage and presentation that will be received by the target cell. Loading of two or more active agents into or onto the same delivery vehicle allows the two or more active agents to be presented to the target cell simultaneously or in an otherwise predetermined order to the target cell.

A. Delivery Vehicles

The nanoparticulate delivery vehicles can be, for example, nanolipogels, polymeric particles, silica particles, liposomes, or multilamellar vesicles. In the most preferred embodiments, the particulate delivery vehicles are nanoscale compositions, for example, 10 nm up to, but not including, about 1 micron. However, it will be appreciated that in some embodiments, and for some uses, the particles can be smaller, or larger (e.g., microparticles, etc.). Although the compositions disclosed herein are referred to nanoparticulate compositions throughout, it will be appreciated that in some embodiments and for some uses the particulate compositions can be somewhat larger than nanoparticles. For example, particulate compositions can be between about 1 micron to about 1000 microns. Such compositions can be referred to as microparticulate compositions.

In preferred embodiments for treating cancer it is desirable that the particle be of a size suitable to access the tumor microenvironment. In particular embodiments, the particle is of a size suitable to access the tumor microenvironment and/or the tumor cells by enhanced permeability and retention (EPR) effect. EPR refers to the property by which certain sizes of molecules (e.g., the particulate compositions discussed herein) tend to accumulate in tumor tissue much more than they do in normal tissues. Therefore, in compositions for treatment of cancer, the delivery vehicle is preferably in the range of about 25 nm to about 500 nm inclusive, more preferably in the range of about 50 nm to about 300 nm inclusive.

1. Nanolipogels

Nanolipogels are core-shell nanoparticulates that combine the advantages of both liposomes and polymer-based particles for sustained delivery of active agents. In some embodiments, nanolipogels may be preferred over polymeric nanoparticles as the delivery vehicles. Generally, nanolipogels may be selected for co-loading of a small molecule hydrophobic drug in combination with a biologic (e.g., protein, peptide, antibody, etc.), co-loading a combination of a hydrophobic and a hydrophilic drug, single or combinations or biologics such as cytokines, antibodies, growth or suppressive protein/peptide factors or whole cells, secreted products thereof or cellular lysates, and/or for applications wherein internalization of the particle and intracellular delivery of the active agent(s) is desired. In some of these embodiments and applications nanolipogels can exhibit, increased loading efficiency, increased sustained release, and improved therapeutic efficacy for combinations of macromolecules and molecules compared to conventional nanoparticle compositions.

As discussed in more detail below, typically, the outer shell of the nanolipogel protects cargo and, provides biocompatibility as well as a surface for functionalization with targeting molecule(s). The outer shell encapsulates components so they are not exposed until desired, for example, in response to environmental conditions or stimuli, creating monodisperse, reproducible particle populations, and mediating internalization into desired cell types. The inner core, which can be a dendrimer or other polymer, has separate and additive functionalities to the outer shell. For example, the inner shell allows for secondary deposition of drug, vaccine, or imaging agent; increases loading of components with different physiochemical properties into the particle; allows for tunable release of contents from particles; increases cytosolic availability of DNA/RNA, drug, and/or protein by disrupting endosomes, all leading to enhanced drug effects, antigen presentation, and transfection/silencing Nanolipogels have a polymer matrix core containing one or more host molecules. The polymeric matrix is preferably a hydrogel, such as a crosslinked block copolymer containing one or more poly(alkylene oxide) segments, such as polyethylene glycol, and one or more aliphatic polyester segments, such as polylactic acid. One or more host molecules, such as a cyclodextrin, dendrimer, or ion exchange resin, is dispersed within or covalently bound to the polymeric matrix. The hydrogel core is surrounded by a liposomal shell.

Nanolipogels can be constructed to incorporate a variety of active agents that can subsequently be released in a controlled fashion. Active agents can be dispersed within the hydrogel matrix, associated with one or more host molecules, dispersed within the liposomal shell, covalently attached to the liposomal shell, and combinations thereof. Active agents can be selectively incorporated at each of these locales within the nanolipogel. Furthermore, the release rate of active agents from each of these locales can be independently tuned. Because each of these locales possesses distinct properties, including size and hydrophobicity/hydrophilicity, the chemical entities independently incorporated at each of these locales can differ dramatically with respect to size and composition. For example, nanolipogels can be loaded with one or more proteins dispersed within the polymeric matrix as well as small molecule hydrophobic drugs associated with host molecules.

For example, in certain embodiments, the nanolipogel core contains two or more active agents. In preferred embodiments, the nanolipogel core contains both a small molecule hydrophobic active agent, preferably associated with one or more suitable host molecules, and a hydrophilic active agent dispersed within the polymeric matrix. In particular embodiments, the hydrophilic active agent is a protein, such as a therapeutic cytokine. By incorporating a hydrophobic active agent in association with a host molecule and a hydrophilic molecule dispersed within the polymeric matrix, controlled release of two or more active agents, including two or more active agents with varied physiochemical characteristics (such as solubility, hydrophobicity/hydrophilicity, molecular weight, and combinations thereof), can be achieved.

In a preferred embodiment, the host molecule is used to deliver a low molecular weight compound such as a chemotherapeutic, where the host molecule retards release of the low molecular weight compound, and a larger hydrophilic compound, such as a cytokine, so that release of both molecules occurs over a similar time period.

In this way, nanolipogels can provide simultaneous sustained release of agents that differ widely in chemical composition and molecular weight. In a non-limiting example, nanolipogels may be loaded with both a hydrophobic, small molecule antigen associated with a host molecule and an immunoadjuvant, such as an immunostimulatory protein, dispersed within the polymeric matrix. These nanolipogels can provide sustained release of the antigen together with the adjuvant, so as to optimize an immune response.

In a particular example, simultaneous sustained delivery by nanolipogels of an immunostimulatory protein, Interleukin-2 (IL-2), as well as a low molecular weight organic molecule, 2-(5-benzo[1,3]dioxol-5-yl-2-tert-butyl-3H-imidazol-4-yl)-6-methylpyridine hydrochloride, an inhibitor of transforming growth factor-$\beta$ (TGF-$\beta$), is achieved. This construct leads to an anti-tumor response in a murine system that is far superior to that achievable with the administration in solution of either agent alone or a combination of the two.

Additionally, nanolipogels can favorably modulate biodistribution of one or more active agents encapsulated therein.

Nanolipogels are typically spherical in shape, with average particle sizes ranging between about 50 nm and about 1000 nm, more preferably between about 75 nm and about 300 nm, most preferably between about 90 nm and about 200 nm. In certain embodiments, the nanolipogels possess an average particle size between about 100 nm and about 140 nm. Particles may be non-spherical.

Depending upon the nature of the lipids present in the liposomal shell of the nanolipogels, nanolipogels having a positive, negative, or near neutral surface charge may be prepared. In certain embodiments, the nanolipogels possess a near neutral surface charge. In certain embodiments, the nanolipogels possess a $\zeta$-potential of between about 10 mV and about −10 mV, more preferably between about 5 mV and about −5 mV, more preferably between about 3 mV and about −3 mV, most preferably between about 2 mV and about −2 mV.

Hydrophobic active agents, such as proteins, may be covalently connected to the surface of the nanolipogel, whereas hydrophilic active agents may be covalently connected to the surface of the nanolipogel or dispersed within the liposomal shell. In certain embodiments, the liposomal shell includes one or more PEGylated lipids. In these cases, one or more active agents may be conjugated to the terminus of one or more PEG chains present on the surface of the liposomal shell.

In another embodiment, the lipid is modified to include an avidin moiety, enabling a biotinylated targeting moiety, detectable label, or other active agent to be coupled thereto, if so desired.

In particular embodiments, one or more active agents are covalently connected to the surface of the nanolipogel via a linking group that is cleaved in response to an external chemical or physical stimulus, such as a change in ambient pH, so as to trigger release of the active agent at a desired physiological locale.

a. Core

The nanolipogel core is formed from a polymeric matrix. The matrix can include one or more host molecules as discussed in more detail below. The nanolipogel core may further include one or more active agents. The active agents may be complexed to a host molecule, dispersed with polymeric matrix, or combinations thereof.

The polymeric matrix of the nanolipogels may be formed from one or more polymers or copolymers. By varying the composition and morphology of the polymeric matrix, one can achieve a variety of controlled release characteristics, permitting the delivery of moderate constant doses of one or more active agents over prolonged periods of time.

The polymeric matrix may be formed from non-biodegradable or biodegradable polymers; however, preferably, the polymeric matrix is biodegradable. The polymeric matrix can be selected to degrade over a time period ranging from one day to one year, more preferably from seven days to 26 weeks, more preferably from seven days to 20 weeks, most preferably from seven days to 16 weeks.

In general, synthetic polymers are preferred, although natural polymers may be used. Representative polymers include poly(hydroxy acids) such as poly(lactic acid), poly (glycolic acid), poly(lactic acid-co-glycolic acids), polyhydroxyalkanoates such as poly3-hydroxybutyrate or poly4-hydroxybutyrate; polycaprolactones; poly(orthoesters); polyanhydrides; poly(phosphazenes); poly(lactide-co-caprolactones); poly(glycolide-co-caprolactones); polycarbonates such as tyrosine polycarbonates; polyamides (including synthetic and natural polyamides), polypeptides, and poly(amino acids); polyesteramides; other biocompatible polyesters; poly(dioxanones); poly(alkylene alkylates); hydrophilic polyethers; polyurethanes; polyetheresters; polyacetals; polycyanoacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), polyvinyl alcohols, polyvinylpyrrolidone; poly(alkylene oxides) such as polyethylene glycol (PEG); derivativized celluloses such as alkyl celluloses (e.g., methyl cellulose), hydroxyalkyl celluloses (e.g., hydroxypropyl cellulose), cellulose ethers, cellulose esters, nitrocelluloses, polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), as well as derivatives, copolymers, and blends thereof.

As used herein, "derivatives" include polymers having substitutions, additions of chemical groups and other modifications to the polymeric backbones described above routinely made by those skilled in the art. Natural polymers, including proteins such as albumin, collagen, gelatin, prolamines, such as zein, and polysaccharides such as alginate and pectin, may also be incorporated into the polymeric matrix. While a variety of polymers may be used to form the polymeric matrix, generally, the resulting polymeric matrix will be a hydrogel. In certain cases, when the polymeric matrix contains a natural polymer, the natural polymer is a biopolymer which degrades by hydrolysis, such as a polyhydroxyalkanoate.

In preferred embodiments, the polymeric matrix contains one or more crosslinkable polymers. Preferably, the crosslinkable polymers contain one or more photo-polymerizable groups, allowing for the crosslinking of the polymeric matrix following nanolipogel formation. Examples of suitable photo-polymerizable groups include vinyl groups, acrylate groups, methacrylate groups, and acrylamide groups. Photo-polymerizable groups, when present, may be incorporated within the backbone of the crosslinkable polymers, within one or more of the sidechains of the crosslinkable polymers, at one or more of the ends of the crosslinkable polymers, or combinations thereof.

The polymeric matrix may be formed from polymers having a variety of molecular weights, so as to form nanolipogels having properties, including drug release rates, optimal for specific applications. Generally, the polymers which make up the polymeric matrix possess average molecular weights ranging between about 500 Da and 50 kDa. In cases where the polymeric matrix is formed from non-crosslinkable polymers, the polymers typically possess average molecular weights ranging between about 1 kDa and about 50 kDa, more preferably between about 1 kDa and about 70 kDa, most preferably between about 5 kDa and about 50 kDa. In cases where the polymeric matrix is formed from crosslinkable polymers, the polymers typically possess lower average molecular weights ranging between about 500 Da and about 25 kDa, more preferably between about 1 kDa and about 10 kDa, most preferably between about 3 kDa and about 6 kDa. In particular embodiments the polymeric matrix is formed from a crosslinkable polymer having an average molecular weight of about 5 kDa.

In some embodiments, the polymeric matrix is formed from a poly(alkylene oxide) polymer or a block copolymer containing one or more poly(alkylene oxide) segments. The poly(alkylene oxide) polymer or poly(alkylene oxide) polymer segments may contain between 8 and 500 repeat units, more preferably between 40 and 300 repeat units, most preferably between 50 and 150 repeat units. Suitable poly(alkylene oxides) include polyethylene glycol (also referred to as polyethylene oxide or PEG), polypropylene 1,2-glycol, poly(propylene oxide), polypropylene 1,3-glycol, and copolymers thereof.

In some embodiments, the polymeric matrix is formed from an aliphatic polyester or a block copolymer containing one or more aliphatic polyester segments. Preferably the polyester or polyester segments are poly(lactic acid) (PLA), poly(glycolic acid) PGA, or poly(lactide-co-glycolide) (PLGA).

In preferred embodiments, the polymeric matrix is formed from a block copolymer containing one or more poly(alkylene oxide) segments, one or more aliphatic polyester segments, and optionally one or more photo-polymerizable groups. In these cases, the one or more poly(alkylene oxide) segments imbue the polymer with the necessary hydrophilicity, such that the resultant polymer matrix forms a suitable hydrogel, while the polyester segments provide a polymeric matrix with tunable hydrophobicity/hydrophilicity and/or the desired in vivo degradation characteristics.

The degradation rate of the polyester segments, and often the corresponding drug release rate, can be varied from days (in the case of pure PGA) to months (in the case of pure PLA), and may be readily manipulated by varying the ratio of PLA to PGA in the polyester segments. In addition, the poly(alkylene oxides), such as PEG, and aliphatic polyesters, such as PGA, PLA, and PLGA have been established as safe for use in humans; these materials have been used in human clinical applications, including drug delivery systems, for more than 30 years.

In certain embodiments, the polymeric matrix is formed from a tri-block copolymer containing a central poly(alkylene oxide) segment, adjoining aliphatic polyester segments attached to either end of the central poly(alkylene oxide) segment, and one or more photo-polymerizable groups. Preferably, the central poly(alkylene oxide) segment is PEG, and aliphatic polyesters segments are PGA, PLA, or PLGA.

Generally, the average molecular weight of the central poly(alkylene oxide) segment is greater than the average molecular weight of the adjoining polyester segments. In certain embodiments, the average molecular weight of the central poly(alkylene oxide) segment is at least three times greater than the average molecular weight of one of the adjoining polyester segments, more preferably at least five times greater than the average molecular weight of one of the adjoining polyester segments, most preferably at least ten times greater than the average molecular weight of one of the adjoining polyester segments.

In some cases, the central poly(alkylene oxide) segment possesses an average molecular weight ranging between about 500 Da and about 10,000 Da, more preferably between about 1,000 Da and about 7,000 Da, most preferably between about 2,500 Da and about 5,000 Da. In particular embodiments, average molecular weight of the central poly(alkylene oxide) segment is about 4,000 Da. Typically, each adjoining polyester segment possesses an average molecular weight ranging between about 100 Da and about 3,500 Da, more preferably between about 100 Da and about 1,000 Da, most preferably between about 100 Da and about 500 Da.

In a preferred embodiment, the polymeric matrix is formed from the tri-block copolymer shown below

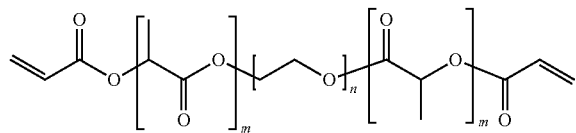

where m and n are, independently for each occurrence, integers between 1 and 500, more preferably between 10 and 150.

Examples of preferred natural polymers include proteins such as albumin, collagen, gelatin and prolamines, for example, zein, and polysaccharides such as alginate, cellulose derivatives and polyhydroxyalkanoates, for example, polyhydroxybutyrate. The in vivo stability of the microparticles can be adjusted during the production by using polymers such as poly(lactide-co-glycolide) copolymerized with polyethylene glycol (PEG). If PEG is exposed on the external surface, it may increase the time these materials circulate due to the hydrophilicity of PEG.

Examples of preferred non-biodegradable polymers include ethylene vinyl acetate, poly(meth)acrylic acid, polyamides, copolymers and mixtures thereof.

The matrix can also be made of gel-type polymers, such as alginate, produced through traditional ionic gelation techniques. The polymers are first dissolved in an aqueous solution, mixed with barium sulfate or some bioactive agent, and then extruded through a microdroplet forming device, which in some instances employs a flow of nitrogen gas to break off the droplet. A slowly stirred (approximately 100-170 RPM) ionic hardening bath is positioned below the extruding device to catch the forming microdroplets. The microparticles are left to incubate in the bath for twenty to thirty minutes in order to allow sufficient time for gelation to occur. Microparticle size is controlled by using various size extruders or varying either the nitrogen gas or polymer solution flow rates. Chitosan microparticles can be prepared by dissolving the polymer in acidic solution and crosslinking it with tripolyphosphate. Carboxymethyl cellulose (CMC) microparticles can be prepared by dissolving the polymer in acid solution and precipitating the microparticle with lead ions. In the case of negatively charged polymers (e.g., alginate, CMC), positively charged ligands (e.g., polylysine, polyethyleneimine) of different molecular weights can be ionically attached.

Perhaps the most widely used are the aliphatic polyesters, specifically the hydrophobic poly(lactic acid) (PLA), more hydrophilic poly(glycolic acid) PGA and their copolymers, poly(lactide-co-glycolide) (PLGA). The degradation rate of these polymers, and often the corresponding drug release rate, can vary from days (PGA) to months (PLA) and is easily manipulated by varying the ratio of PLA to PGA. Second, the physiologic compatibility of PLGA and its homopolymers PGA and PLA have been established for safe use in humans; these materials have a history of over 30 years in various human clinical applications including drug delivery systems. PLGA nanoparticles can be formulated in a variety of ways that improve drug pharmacokinetics and biodistribution to target tissue by either passive or active targeting. The microparticles are designed to release molecules to be encapsulated or attached over a period of days to weeks. Factors that affect the duration of release include pH of the surrounding medium (higher rate of release at pH 5 and below due to acid catalyzed hydrolysis of PLGA) and polymer composition. Aliphatic polyesters differ in hydrophobicity and that in turn affects the degradation rate. Specifically the hydrophobic poly(lactic acid) (PLA), more hydrophilic poly (glycolic acid) PGA and their copolymers, poly(lactide-co-glycolide) (PLGA) have various release rates. The degradation rate of these polymers, and often the corresponding drug release rate, can vary from days (PGA) to months (PLA) and is easily manipulated by varying the ratio of PLA to PGA.

b. Shell Components

Nanolipogels include a liposomal shell composed of one or more concentric lipid monolayers or lipid bilayers. The shell can further include one or more active agents, targeting molecules, or combinations thereof.

Nanolipogels include a liposomal shell composed of one or more concentric lipid monolayers or lipid bilayers. The composition of the liposomal shell may be varied to influence the release rate of one or more active agents in vivo. The lipids may also be covalently crosslinked, if desired, to alter in vivo drug release.

The lipid shell can be formed from a single lipid bilayer (I.e., the shell may be unilamellar) or several concentric lipid bilayers (i.e., the shell may be multilamellar). The lipid shell may be formed from a single lipid; however, in preferred embodiments, the lipid shell is formed from a combination of more than one lipid. The lipids can be neutral, anionic or cationic at physiologic pH.

Suitable neutral and anionic lipids include sterols and lipids such as cholesterol, phospholipids, lysolipids, lysophospholipids, and sphingolipids. Neutral and anionic lipids include, but are not limited to, phosphatidylcholine (PC) (such as egg PC, soy PC), including 1,2-diacyl-glycero-3-phosphocholines; phosphatidylserine (PS), phosphatidylglycerol, phosphatidylinositol (PI); glycolipids; sphingophospholipids, such as sphingomyelin; sphingoglycolipids (also known as 1-ceramidyl glucosides), such as ceramide galactopyranoside, gangliosides and cerebrosides; fatty acids, sterols containing a carboxylic acid group such as cholesterol or derivatives thereof; and 1,2-diacyl-sn-glycero-3-phosphoethanolamines, including 1,2-dioleoyl-sn-Glycero-3-phosphoethanolamine or 1,2-dioleolylglyceryl phosphatidylethanolamine (DOPE), 1,2-dihexadecylphosphoethanolamine (DHPE), 1,2-distearoylphosphatidylcholine (DSPC), 1,2-dipalmitoylphosphatidylcholine (DPPC), and 1,2-dimyristoylphosphatidylcholine (DMPC). Also suitable are natural (e.g., tissue derived L-α-phosphatidyl: egg yolk, heart, brain, liver, soybean) and/or synthetic (e.g., saturated and unsaturated 1,2-diacyl-sn-glycero-3-phosphocholines, 1-acyl-2-acyl-sn-glycero-3-phosphocholines, 1,2-diheptanoyl-SN-glycero-3-phosphocholine) derivatives of these lipids.

Suitable cationic lipids include N-[1-(2,3-dioleoyloxy) propyl]-N,N,N-trimethyl ammonium salts, also referred to as TAP lipids, for example as a methylsulfate salt. Suitable TAP lipids include, but are not limited to, DOTAP (dioleoyl-), DMTAP (dimyristoyl-), DPTAP (dipalmitoyl-), and DSTAP (distcaroyl-). Other suitable cationic lipids include dimethyldioctadecyl ammonium bromide (DDAB), 1,2-diacyloxy-3-trimethylammonium propanes, N-[1-(2,3-dioloxy)propyl]-N,N-dimethyl amine (DODAP), 1,2-diacyloxy-3-dimethylammonium propanes, N-[1-(2,3-diolcyloxy)propyl]-N,N,N-trimethylammonium chloride (DOTMA), 1,2-dialkyloxy-3-dimethylammonium propanes, dioctadecylamidoglycylspermine (DOGS), 3-[N—(N',N'-dimethylamino-ethane)carbamoyl]cholesterol (DC-Chol);

2,3-dioleoyloxy-N-(2-(sperminecarboxamido)-ethyl)-N,N-dimethyl-1-propanaminium trifluoro-acetate (DOSPA), β-alanyl cholesterol, cetyltrimethylammonium bromide (CTAB), $diC_{14}$-amidine, N-tert-butyl-N'-tetradecyl-3-tetradecylamino-propionamidine, N-(alpha-trimethylammonio-acetyl)didodecyl-D-glutamate chloride (TMAG), ditetradecanoyl-N-(trimethylammonio-acetyl)diethanolamine chloride, 1,3-dioleoyloxy-2-(6-carboxy-spermyl)-propylamide (DOSPER), and N,N,N',N'-tetramethyl-, N'-bis(2-hydroxylethyl)-2,3-dioleoyloxy-1,4-butanediammonium iodide, 1-[2-(acyloxy)ethyl]2-alkyl(alkenyl)-3-(2-hydroxyethyl)-imidazolinium chloride derivatives, such as 1-[2-(9(Z)-octadecenoyloxy)ethyl]-2-(8(Z)-heptadecenyl-3-(2-hydroxyethyl)imidazolinium chloride (DOTIM) and 1-[2-(hexadecanoyloxy)ethyl]-2-pentadecyl-3-(2-hydroxyethyl) imidazolinium chloride (DPTIM), and 2,3-dialkyloxypropyl quaternary ammonium derivatives containing a hydroxyalkyl moiety on the quaternary amine, for example, 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimethyl-hydroxypropyl ammonium bromide (DORIE-HP), 1,2-dioleyl-oxy-propyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxylethyl ammonium bromide (DMRIE), 1,2-dipalmityloxypropyl-3-dimethyl-hydroxyethyl ammonium bromide (DPRIE), and 1,2-disteryloxypropyl-3-dimethyl-hydroxyethyl ammonium bromide (DSRIE).

Other suitable lipids include PEGylated derivatives of the neutral, anionic, and cationic lipids described above. Incorporation of one or more PEGylated lipid derivatives into the lipid shell can result in a nanolipogel which displays polyethylene glycol chains on its surface. The resulting nanolipogels may possess increased stability and circulation time in vivo as compared to nanolipogels lacking PEG chains on their surfaces. Examples of suitable PEGylated lipids include distearoylphosphatidylethanolamine-polyethylene glycol (DSPE-PEG), including DSPE PEG (2000 MW) and DSPE PEG (5000 MW), dipalmitoyl-glycero-succinate polyethylene glycol (DPGS-PEG), stearyl-polyethylene glycol and cholesteryl-polyethylene glycol.

In preferred embodiments, the lipid shell is formed from a combination of more than one lipid. In certain embodiments the lipid shell is formed from a mixture of at least three lipids. In particular embodiments, the lipid shell is formed from a mixture of phosphatidyl choline (PC), 1,2-distearoyl-sn-glycero-3-phosphoethanolamine-N-[amino(polyethylene glycol)-2000] (DSPE-PEG), and cholesterol.

In some embodiments, the lipid shell is formed from a mixture of one or more PEGylated phospholipids and one or more additional lipids or sterols. In certain instances, the molar ratio of the one or more PEGylated lipids to the one or more additional lipids or sterols ranges from about 1:1 to about 1:6, more preferably from about 1:2 to about 1:6, most preferably from about 1:3 to about 1:5. In particular embodiments, the molar ratio of the one or more PEGylated lipids to the one or more additional lipids or sterols is about 1:4.

In some embodiments, the lipid shell is formed from a mixture of one or more phospholipids and one or more additional lipids or sterols. In certain instances, the molar ratio of the one or more phospholipids to the one or more additional lipids or sterols ranges from about 1:1 to about 6:1, more preferably from about 2:1 to about 6:1, most preferably from about 3:1 to about 5:1. In particular embodiments, the molar ratio of the one or more phospholipids to the one or more additional lipids or sterols is about 4:1.

In preferred embodiments, the lipid shell is formed from a mixture of a phospholipid, such as phosphatidyl choline (PC), a PEGylated phospholipid, such as 1,2-distearoyl-sn-glycero-3-phosphoethanolamine-N-[amino(polyethylene glycol)-2000] (DSPE-PEG), and cholesterol. In particular embodiments, the lipid shell is formed from a mixture of phosphatidyl choline, 1,2-distearoyl-sn-glycero-3-phosphoethanolamine-N-[amino(polyethylene glycol)-2000] (DSPE-PEG), and cholesterol in a 3:1:1 molar ratio.

2. Polymeric Particles

The nanoparticulate delivery vehicle can also be a polymeric particle, for example a micro- or a nanoparticle.

The particles can be biodegradable or non-biodegradable.

Exemplary polymers that can be used to manufacture polymeric particles are discussed above with respect to the polymeric matrix component of nanolipogels.

Examples of preferred biodegradable polymers include polymers of hydroxy acids such as lactic acid and glycolic acid, and copolymers with PEG, polyanhydrides, poly(ortho)esters, polyurethanes, poly(butyric acid), poly(valeric acid), poly(lactide-co-caprolactone), blends and copolymers thereof. In preferred embodiments, the particles are composed of one or more polyesters.

For example, particles can contain one more of the following polyesters: homopolymers including glycolic acid units, referred to herein as "PGA", and lactic acid units, such as poly-L-lactic acid, poly-D-lactic acid, poly-D,L-lactic acid, poly-L-lactide, poly-D-lactide, and poly-D,L-lactide, collectively referred to herein as "PLA", and caprolactone units, such as poly(s-caprolactone), collectively referred to herein as "PCL"; and copolymers including lactic acid and glycolic acid units, such as various forms of poly(lactic acid-co-glycolic acid) and poly(lactide-co-glycolide) characterized by the ratio of lactic acid:glycolic acid, collectively referred to herein as "PLGA"; and polyacrylates, and derivatives thereof. Exemplary polymers also include copolymers of polyethylene glycol (PEG) and the aforementioned polyesters, such as various forms of PLGA-PEG or PLA-PEG copolymers, collectively referred to herein as "PEGylated polymers". In certain embodiments, the PEG region can be covalently associated with polymer to yield "PEGylated polymers" by a cleavable linker. Alginate polymers may also be used.

In some embodiments, the particles are composed of PLGA. PLGA is a safe, FDA approved polymer. PLGA particles are advantageous because they can protect the active agent (i.e., the encapsulant), promote prolonged release, and are amenable to the addition of targeting moieties. For example, the polymer of the particle can have the structure:

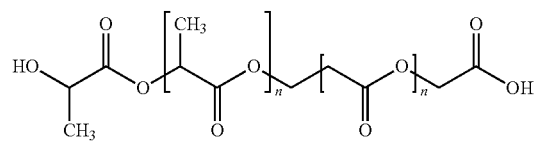

(poly(lactic co-glycolic acid) PLGA+$H_2O$=variable degradation (days to weeks).

The particles can contain one or more polymer conjugates containing end-to-end linkages between the polymer and a targeting moiety, detectable label, or other active agent. For example, a modified polymer can be a PLGA-PEG-phosphonate. In another example, the particle is modified to include an avidin moiety and a biotinylated targeting moiety, detectable label, or other active agent can be coupled thereto.

Examples of preferred natural polymers include proteins such as albumin, collagen, gelatin and prolamines, for example, zein, and polysaccharides such as alginate, cellulose derivatives and polyhydroxyalkanoates, for example, polyhydroxybutyrate. The in vivo stability of the particles can be adjusted during the production by using polymers such as poly(lactide-co-glycolide) copolymerized with polyethylene glycol (PEG). If PEG is exposed on the external surface, it may increase the time these materials circulate due to the hydrophilicity of PEG.

Examples of preferred non-biodegradable polymers include ethylene vinyl acetate, poly(meth)acrylic acid, polyamides, copolymers and mixtures thereof.

3. Other Delivery Vehicles

In some embodiments, the delivery vehicles are liposomes. Liposomes are typically spherical vesicles composed of a lamellar phase lipid bilayer. The liposomes can be, for example, multilamellar vesicles (MLV), small unilamellar liposome vesicles (SUV), large unilamellar vesicles (LUV), or cochleate vesicles. Liposomes, miscelles, and other lipid-based delivery vehicles useful for preparation of the disclosed nanoparticulate compositions are known in the art. See, for example, Torchilin, et al., *Advanced Drug Delivery Reviews,* 58(14):1532-55 (2006).

The delivery vehicle can also be silica particles. Suitable silica particles useful for preparation of the disclosed nanoparticulate compositions are also known in the art. See, for example, Barbe, et al., *Advanced Materials,* 16(21):1959-1966 (2004) and Argyo, et al., *Chem. Mater.,* 26(1):435-451 (2014).

B. Active Agents

The nanoparticulate compositions disclosed herein typically include a nanolipogel or micro- or nanoparticle or other delivery vehicle wherein one or more active agents are loaded into, attached to the surface of, and/or enclosed within the delivery vehicle. In some embodiments, two, three, four, or more active agents are loaded into, attached to the surface of, and/or enclosed within the delivery vehicle. The two or more agents can be loaded into, attached to the surface of, and/or enclosed within the same particle, or different particles.

In some embodiments, the formulation includes two or more different types of particles having the same or different active agent(s) associated therewith.

The formulation can include one or more active agents that are not loaded into, attached to the surface of, and/or enclosed within the disclosed delivery vehicle(s). For example, such active agents can be free or soluble active agent(s), or active agent(s) in a different carrier or dosage form but are nonetheless part of the same pharmaceutical composition as the nanoparticulate composition.

As described in more detail below, in some embodiments, the disclosed methods include administering to a subject in need thereof a nanoparticulate composition that includes one, two, three or more active agents loaded into, attached to the surface of, and/or enclosed within the delivery vehicle in combination with one, two, three or more additional active agents that are administered to the subject as one or more separate formulations. In some embodiments, additional active agents are co-administered to the subject but are not loaded into, attached to the surface of, and/or enclosed within the disclosed delivery vehicle(s), and can be, for example, free or soluble, or in a different carrier or dosage form. Any of the disclosed active agents can be loaded into, attached to the surface of, and/or enclosed within the delivery vehicle and administered to a subject in need thereof as part of a nanoparticulate composition. Any of the disclosed active agents can be administered to a subject as free or soluble or as part of another dosage unit or dosage form administered to a subject in combination with a nanoparticulate composition.

Exemplary active agents include, for example, tumor antigens, CD4+ T-cell epitopes, cytokines, chemotherapeutic agents, radionuclides, small molecule signal transduction inhibitors, photothermal antennas, immunologic danger signaling molecules, other immunotherapeutics, enzymes, antibiotics, antivirals, anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, immunomodulators (including ligands that bind to Toll-Like Receptors (including but not limited to CpG oligonucleotides) to activate the innate immune system, molecules that mobilize and optimize the adaptive immune system, molecules that activate or up-regulate the action of cytotoxic T lymphocytes, natural killer cells and helper T-cells, and molecules that deactivate or down-regulate suppressor or regulatory T-cells), agents that promote uptake of the delivery vehicle into cells (including dendritic cells and other antigen-presenting cells), nutraceuticals such as vitamins, and oligonucleotide drugs (including DNA, RNAs, antisense, aptamers, small interfering RNAs, ribozymes, external guide sequences for ribonuclease P, and triplex forming agents).

In preferred embodiments, one or more of the active agents is an immunomodulator such as an immune response stimulating agent or an agent that blocks immunosuppression. In particularly preferred embodiments, the active agents target tumor checkpoint blockade or costimulatory molecules. It is believed that the nanoparticulate compositions and methods of use disclosed herein can increase the efficacy and/or reduce the toxicity compared to administered the same agent alone. For example, as discussed in more detail below, some of the compositions and methods include co-administering a nanoparticulate adjuvant (typically a biodegradable nanoparticulate composition encapsulating a small molecule drug and or biological agent) in combination with conventional cancer treatments (e.g., immunotherapies or chemotherapies associated with immune signaling properties). Such combination therapies and regimens can increase efficacy, reduce toxicity and lower the overall dose at administration. Particular embodiments are discussed in more detail below.

1. Immune Response Stimulating Agents

One or more of the active agents can be an immune response stimulating agent. The immune system is composed of cellular (T-cell driven) and humoral (B-cell driven) elements. It is generally accepted that for cancer, triggering of a powerful cell-mediated immune response is more effective than activation of humoral immunity. Cell-based immunity depends upon the interaction and co-operation of a number of different immune cell types, including antigen-presenting cells (APC; of which dendritic cells are an important component), cytotoxic T cells, natural killer cells and T-helper cells. Therefore, the active agent can be an agent that increases a cell (T-cell driven) immune response, a humoral (B-cell driven) immune response, or a combination thereof. For example, in some embodiments, the agent enhances a T cell response, increases T cell activity, increases T cell proliferation, reduces a T cell inhibitory signal, enhances production of cytokines, stimulates T cell differentiation or effector function, promotes survival of T cells or any combination thereof.

Exemplary immunomodulatory agents include cytokines, xanthines, interleukins, interferons, oligodeoxynucleotides, glucans, growth factors (e.g., TNF, CSF, GM-CSF and G-CSF), hormones such as estrogens (diethylstilbestrol, estradiol), androgens (testosterone, HALOTESTIN® (fluoxymesterone)), progestins (MEGACE® (megestrol acetate), PROVERA® (medroxyprogesterone acetate)), and corticosteroids (prednisone, dexamethasone, hydrocortisone).

In some embodiments the agent is an inflammatory molecule such as a cytokine, metalloprotease or other molecule including, but not limited to, IL-1β, TNF-α, TGF-beta, IFN-γ, IL-17, IL-6, IL-23, IL-22, IL-21, and MMPs.

a. Cytokines

In a preferred embodiment, at least one of the active agents is a proinflammatory cytokine. Cytokines typically act as hormonal regulators or signaling molecules at nano- to-picomolar concentrations and help in cell signaling. The cytokine can be a protein, peptide, or glycoprotein. Exemplary cytokines include, but are not limited to, interleukins (e.g., IL-1, IL-2, IL-4, IL-5, IL-6, L-7, IL-12, IL-15, etc.), interferons (e.g., interferon-γ), macrophage colony stimulating factor, granulocyte colony stimulating factor, tumor necrosis factor, Leukocyte Inhibitory Factor (LIF), chemokines, SDF-1α, and the CXC family of cytokines.

b. Chemokines

In another embodiment, at least one of the active agents is a proinflammatory chemokine. Chemokines are a family of small cytokines. Their name is derived from their ability to induce directed chemotaxis in nearby responsive cells. Therefore, they are chemotactic cytokines. Proteins are classified as chemokines according to shared structural characteristics such as small size (they are all approximately 8-10 kilodaltons in size), and the presence of four cysteine residues in conserved locations that are key to forming their 3-dimensional shape. Chemokines have been classified into four main subfamilies: CXC, CC, CX3C and XC. Chemokines induce cell signaling by binding to G protein-linked transmembrane receptors (i.e., chemokine receptors).

2. Agents that Block Immune Suppression

At least one of the active agents can be an agent that blocks, inhibits or reduces immune suppression or that that blocks, inhibits or reduces the bioactivity of a factor that contributes to immune suppression. It has become increasingly clear that tumor-associated immune suppression not only contributes greatly to tumor progression but is also one of the major factors limiting the activity of cancer immunotherapy. Antigen-specific T-cell tolerance is one of the major mechanisms of tumor escape, and the antigen-specific nature of tumor non-responsiveness indicates that tumor-bearing hosts are not capable of maintaining tumor-specific immune responses while still responding to other immune stimuli (Willimsky, et al., *Immunol. Rev.*, 220:102-12 (2007), Wang, et al. *Semin Cancer Biol.*, 16:73-9 (2006), Frey, et al., *Immunol. Rev.*, 222:192-205 (2008), Nagaraj, et al., *Clinical Cancer Research*, 16(6):1812-23 (2010)).

a. Agents that Deplete Tregs

Regulatory T cells (Tregs) are essential for maintaining self-tolerance as defects in their compartment lead to severe autoimmune diseases. However, this important function is contrasted with their detrimental effects on tumor immunosurveillance and antitumor immunity. Increases in Tregs within tumors and circulation of cancer patients have been implicated in cancer pathogenesis and disease progression and mechanisms ranging from proliferation to specific trafficking networks have been identified to account for their accumulation. In vitro experiments indicate several soluble or contact-dependent tumor factors contributing to Treg generation including cyclooxygenase-2, CD70, Gal1, TGF-β, indoleamine 2,3-dioxygenase, and other yet-to-be-identified factors. Enhanced local Treg proliferation or reduced apoptosis could contribute to increased tumor Treg numbers. Accordingly, in some embodiments, at least one of the agents reduces cyclooxygenase-2, CD70, Gal1, TGF-β or indoleamine 2,3-dioxygenase, reduces local Treg proliferation and/or increases Treg apoptosis, particularly in or near the tumor.

Various immunotherapeutic approaches for overcoming the antagonistic effects exerted by Tregs are reviewed in Mougiakakos *Adv Cancer Res*, 107:57-117 (2010), De Rezende, et al., *Arch. Immunol. Ther. Exp.*, 58(3):179-90 (2010), and Curiel, *Curr. Opin. Immunol.*, 20(2):241-246 (2008).

In some embodiments, the agent depletes Tregs; blocks Treg differentiation, trafficking, effector functions, or a combination thereof; raises effector cell suppression threshold, or any combination thereof. Exemplary agents that deplete Tregs or block their function include anti-CD25 antibody, cyclophosphamide, denileukin diftitox (Ontak, a protein fusing IL-2 and diphtheria toxin, LMB-2 (a CD25-directed *Pseudomonas* immunotoxin), CpG treatment, and anti-CTLA4 antibody (Curiel, *Curr Opin Immunol.*, 20(2):241-246 (2008)).

Targeting tumor antigen-specific Tregs might also be effective to reduce the ability of tumors to evade the immune system. Tumor antigen-specific Tregs occur naturally and are induced by vaccination. Folate receptor 4-expressing tumor Tregs may be enriched for antigen-specific cells, and their depletion in tumor-bearing mice improved immune-mediated tumor rejection. Accordingly, in some embodiments, the nanoparticulate compositions are targeted to folate receptor 4-expressing tumor Tregs.

In some embodiments at least one of the agents is a TGF-β modulator. After latent TGF-β is released from a tumor cell, it binds with integrin on the surface of the tumor cell, leading to the activation of the latent TGF-β. As a result, increased TGF-β concentrations in the tumor microenvironment support immune suppression by recruiting regulatory T cells (Massayo, et al., *Eur J Clin Med Oncol.*, (4):27-32 (2013).

i SB505124

Elevated TGF-β molecules can be inhibited by a TGF-β inhibitor such as SB505124 (2-(5-benzo[1,3]dioxol-5-yl-2-tert-butyl-3H-imidazol-4-yl)-6-methylpyridine hydrochloride). SB505124 (also known as SB-505124 or abbreviated as SB) is a selective inhibitor of TGF-β type I receptors ALK4, ALK5, and ALK7 (DaCosta, et al., *Mol Pharmacol.* 65:744-52 (2004)). In a particular embodiment, SB505124 is complexed with a host molecule such as cyclodextrin.

ii. Losartan

Another TGF-β modulator is losartan (also known as COZAAR®). Losartan, best known as an angiotensin II receptor antagonist, also down-regulates TGF-β (Guo, et al., *Zhonghua Nei Ke Za Zhi*, 42:403-8 (2003)). Losartan (2-butyl-4-chloro-1-{[2'-(1H-tetrazol-5-yl)biphenyl-4-yl] methyl}-1H-imidazol-5-yl)methanol) has the structure:

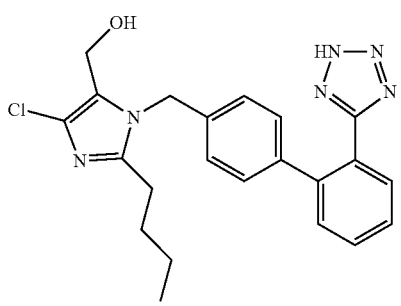 [SMILES: CCCCc1nc(Cl)c(CO)n1Cc1ccc(-c2ccccc2-c2nn[nH]n2)cc1]

Losartan is well absorbed following oral administration and undergoes significant first-pass metabolism to produce 5-carboxylic acid metabolite, designated as EXP3174. This metabolite is a long-acting (6 to 8 hr), noncompetitive antagonist at the AT1 receptor, and contributes to the pharmacological effects of losartan. Losartan has been identified as a treatment for a number of indications including hypertension, optionally in combination with other antihypertensives, diabetic neuropathy, optionally in combination with hypoglycemic agents, chronic heart failure and in combination with Hydrochlorothiazide (HCTZ) for decreasing the risk of stroke. The potassium salt has been formulated as tablets with the strength of 12.5, 25, 50 and 100 mg and also as a 2.5 mg/ml powder for suspension. A combination product of losartan with HCTZ (Hyzaar) is also available as tablets with the strength of 50 mg/12.5 mg, 100 mg/12.5 mg and 100 mg/25 mg. Compositions and formulations including losartan and pharmaceutical salts and imidazole derivatives thereof, and methods of use thereof are discussed in U.S. Pat. Nos. 5,138,069, 5,153,197, 5,128,355, 5,155,118, 5,210,079, and 5,354,867.

In some embodiments, losartan, or a pharmaceutical salt, imidazole derivative, or metabolite thereof is loaded into, attached to the surface of, and/or enclosed within a delivery vehicle, for example a polymeric nanoparticle or a nanolipogel. Preferably, a second active agent is also loaded into, attached to the surface of, and/or enclosed within the delivery vehicle. The second active agent can be a second immunomodulator, for example IL-2. In a particular embodiment, PLGA nanoparticles or nanolipogels are loaded with losartan and IL-2. In some embodiments, the delivery vehicles include a targeting moiety such as RGD peptide.

Methods for loading these agents onto nanoparticles can include methods such as those described below in Examples 3 and 7, respectively. The particles can be PLGA nanoparticles, nanolipogels, or other biodegradable polymers.

In an exemplary assay to test the anti-tumor efficacy of different particles and/or dosages of the active agents, animals are inoculated with B16F10 melanoma cells in the hind limb. Tumor growth is monitored and, beginning approximately 7 days later, when the tumor reaches 0.5 mm² in area, animals are subjected to a course of peritrumoral injections of 5 ug of nanoparticles (a) loaded with IL-2 and Losartan; or, as controls, (b) blank particles (similar to assays described in the Examples below).

b. Agents that Deplete Myeloid-Derived Suppressor Cells

Myeloid-derived suppressor cells (MDSC) may represent a major population of antigen presenting cells responsible for the induction of antigen-specific CD8+ T-cell tolerance in cancer. Therefore, in some embodiments, the composition includes an agent that reduces the number or activity of MDSC. Exemplary agents that can be used to eliminate MDSC include, but are not limited to, differentiating agents such as all-trans retinoic acid, chemotherapeutic drugs, aminobiphosphonates, tyrosine kinase inhibitors (e.g., sunitinib), cyclooxygenase 2 inhibitors, and inhibition of MDSC function by the phosphodiesterase-5 inhibitors (sildanefil), and synthetic triterpenoids, (e.g., methyl ester of 2-cyano-3,12-dioxooleana-1,9(11)-dien-28-oic acid (also referred to as CDDO-Me and bardoxolone methyl) ((Nagaraj, et al., *Clinical Cancer Research*, 16(6):1812-23 (2010)).

c. PD-1 antagonists

In some embodiments, the active agents are PD-1 antagonists. Activation of T cells normally depends on an antigen-specific signal following contact of the T cell receptor (TCR) with an antigenic peptide presented via the major histocompatibility complex (MHC) while the extent of this reaction is controlled by positive and negative antigen-independent signals eminating from a variety of co-stimulatory molecules. The latter are commonly members of the CD28/B7 family. Conversely, Programmed Death-1 (PD-1) is a member of the CD28 family of receptors that delivers a negative immune response when induced on T cells. Contact between PD-1 and one of its ligands (B7-H1 or B7-DC) induces an inhibitory response that decreases T cell multiplication and/or the strength and/or duration of a T cell response. Suitable PD-1 antagonists are described in U.S. Pat. Nos. 8,114,845, 8,609,089, and 8,709,416, and include compounds or agents that either bind to and block a ligand of PD-1 to interfere with or inhibit the binding of the ligand to the PD-1 receptor, or bind directly to and block the PD-1 receptor without inducing inhibitory signal transduction through the PD-1 receptor.

In some embodiments, the PD-1 receptor antagonist binds directly to the PD-1 receptor without triggering inhibitory signal transduction and also binds to a ligand of the PD-1 receptor to reduce or inhibit the ligand from triggering signal transduction through the PD-1 receptor. By reducing the number and/or amount of ligands that bind to PD-1 receptor and trigger the transduction of an inhibitory signal, fewer cells are attenuated by the negative signal delivered by PD-1 signal transduction and a more robust immune response can be achieved.

It is believed that PD-1 signaling is driven by binding to a PD-1 ligand (such as B7-H1 or B7-DC) in close proximity to a peptide antigen presented by major histocompatibility complex (MHC) (see, for example, Freeman, *Proc. Natl. Acad. Sci. U. S. A*, 105:10275-10276 (2008)). Therefore, proteins, antibodies or small molecules that prevent co-ligation of PD-1 and TCR on the T cell membrane are also useful PD-1 antagonists.

In preferred embodiments, the PD-1 receptor antagonists are small molecule antagonists or antibodies that reduce or interfere with PD-1 receptor signal transduction by binding to ligands of PD-1 or to PD-1 itself, especially where co-ligation of PD-1 with TCR does not follow such binding, thereby not triggering inhibitory signal transduction through the PD-1 receptor.

Other PD-1 antagonists contemplated by the methods of this invention include antibodies that bind to PD-1 or ligands of PD-1, and other antibodies.

Suitable anti-PD-1 antibodies include, but are not limited to, those described in the following publications:
PCT/IL03/00425 (Hardy et al., WO/2003/099196)
PCT/JP2006/309606 (Korman et al., WO/2006/121168)
PCT/US2008/008925 (Li et al., WO/2009/014708)
PCT/JP03/08420 (Honjo et al., WO/2004/004771)
PCT/JP04/00549 (Honjo et al., WO/2004/072286)
PCT/IB2003/006304 (Collins et al., WO/2004/056875)

PCT/US2007/088851 (Ahmed et al., WO/2008/083174)
PCT/US2006/026046 (Korman et al., WO/2007/005874)
PCT/US2008/084923 (Terrett et al., WO/2009/073533)
Berger et al., *Clin. Cancer Res.*, 14:30443051 (2008).

A specific example of an anti-PD-1 antibody is MDX-1106 (see Kosak, US 20070166281 (pub. 19 Jul. 2007) at par. 42), a human anti-PD-1 antibody, preferably administered at a dose of 3 mg/kg.

Exemplary anti-B7-H1 antibodies include, but are not limited to, those described in the following publications:
PCT/US06/022423 (WO/2006/133396, pub. 14 Dec. 2006)
PCT/US07/088851 (WO/2008/083174, pub. 10 Jul. 2008)
US 2006/0110383 (pub. 25 May 2006)

A specific example of an anti-B7-H1 antibody is MDX-1105 (WO/2007/005874, published 11 Jan. 2007)), a human anti-B7-H1 antibody.

For anti-B7-DC antibodies see U.S. Pat. Nos. 7,411,051, 7,052,694, 7,390,888, and U.S. Published Application No. 2006/0099203.

The antibody can be a bi-specific antibody that includes an antibody that binds to the PD-1 receptor bridged to an antibody that binds to a ligand of PD-1, such as B7-H1. In some embodiments, the PD-1 binding portion reduces or inhibits signal transduction through the PD-1 receptor.

Other exemplary PD-1 receptor antagonists include, but are not limited to B7-DC polypeptides, including homologs and variants of these, as well as active fragments of any of the foregoing, and fusion proteins that incorporate any of these. In a preferred embodiment, the fusion protein comprises the soluble portion of B7-DC coupled to the Fc portion of an antibody, such as human IgG, and does not incorporate all or part of the transmembrane portion of human B7-DC.

The PD-1 antagonist can also be a fragment of a mammalian B7-H1, preferably from mouse or primate, preferably human, wherein the fragment binds to and blocks PD-1 but does not result in inhibitory signal transduction through PD-1. The fragments can also be part of a fusion protein, for example an Ig fusion protein.

Other useful polypeptides PD-1 antagonists include those that bind to the ligands of the PD-1 receptor. These include the PD-1 receptor protein, or soluble fragments thereof, which can bind to the PD-1 ligands, such as B7-H1 or B7-DC, and prevent binding to the endogenous PD-1 receptor, thereby preventing inhibitory signal transduction. B7-H1 has also been shown to bind the protein B7.1 (Butte et al., *Immunity*, Vol. 27, pp. 111-122, (2007)). Such fragments also include the soluble ECD portion of the PD-1 protein that includes mutations, such as the A99L mutation, that increases binding to the natural ligands (Molnar et al., *PNAS*, 105:10483-10488 (2008)). B7-1 or soluble fragments thereof, which can bind to the B7-H1 ligand and prevent binding to the endogenous PD-1 receptor, thereby preventing inhibitory signal transduction, are also useful.

PD-1 and B7-H1 anti-sense nucleic acids, both DNA and RNA, as well as siRNA molecules can also be PD-1 antagonists. Such anti-sense molecules prevent expression of PD-1 on T cells as well as production of T cell ligands, such as B7-H1, PD-L1 and/or PD-L2. For example, siRNA (for example, of about 21 nucleotides in length, which is specific for the gene encoding PD-1, or encoding a PD-1 ligand, and which oligonucleotides can be readily purchased commercially) complexed with carriers, such as polyethyleneimine (see Cubillos-Ruiz et al., J. Clin. Invest. 119(8): 2231-2244 (2009), are readily taken up by cells that express PD-1 as well as ligands of PD-1 and reduce expression of these receptors and ligands to achieve a decrease in inhibitory signal transduction in T cells, thereby activating T cells.

d. CTLA4 Antagonists

Other molecules useful in mediating the effects of T cells in an immune response are also contemplated as active agents. For example, in some embodiments, the molecule is an agent binds to an immune response mediating molecule that is not PD-1. In a preferred embodiment, the molecule is an antagonist of CTLA4, for example an antagonistic anti-CTLA4 antibody. An example of an anti-CTLA4 antibody contemplated for use in the methods of the invention includes an antibody as described in PCT/US2006/043690 (Fischkoff et al., WO/2007/056539).

Dosages for anti-PD-1, anti-B7-H1, and anti-CTLA4 antibody, are known in the art and can be in the range of 0.1 to 100 mg/kg, with shorter ranges of 1 to 50 mg/kg preferred and ranges of 10 to 20 mg/kg being more preferred. An appropriate dose for a human subject is between 5 and 15 mg/kg, with 10 mg/kg of antibody (for example, human anti-PD-1 antibody, like MDX-1106) most preferred.

Specific examples of an anti-CTLA4 antibody useful in the methods of the invention are Ipilimumab, also known as MDX-010 or MDX-101, a human anti-CTLA4 antibody, preferably administered at a dose of about 10 mg/kg, and Tremelimumab a human anti-CTLA4 antibody, preferably administered at a dose of about 15 mg/kg. See also Sammartino, et al., *Clinical Kidney Journal*, 3(2):135-137 (2010), published online December 2009.

In other embodiments, the antagonist is a small molecule. A series of small organic compounds have been shown to bind to the B7-1 ligand to prevent binding to CTLA4 (see Erbe et al., *J. Biol. Chem.*, 277:7363-7368 (2002). Such small organics could be administered alone or together with an anti-CTLA4 antibody to reduce inhibitory signal transduction of T cells.

3. Adjuvants and Antigens

In some embodiments, the nanoparticulate compositions are used as part of vaccine formulations or as adjuvants to stimulate the immune system. In some embodiments an antigen and/or adjuvant is loaded into, attached to the surface of, and/or enclosed within the delivery vehicle. In some embodiments an antigen and/or adjuvant is administered in combination with an active agent loaded into, attached to the surface of, and/or enclosed within the delivery vehicle. The antigen and/or adjuvant can be free from the particles. For example, the antigen and/or adjuvant can be soluble.

These antigens may also be absorbed after administration. For example, since NLGs can absorb tumor antigens in situ, the NLGs may be administered with immunestimulant and/or chemotherapeutic, then absorb tumor antigen as the tumor cells die. Peptide, protein, and DNA based vaccines may be used to induce immunity to various diseases or conditions. Cell-mediated immunity is needed to detect and destroy virus-infected cells. Most traditional vaccines (e.g. protein-based vaccines) can only induce humoral immunity. DNA-based vaccines represent a unique means to vaccinate against a virus or parasite because a DNA-based vaccine can induce both humoral and cell-mediated immunity. In addition, DNA-based vaccines are potentially safer than traditional vaccines. DNA vaccines are relatively more stable and more cost-effective for manufacturing and storage. DNA vaccines consist of two major components, DNA carriers (or delivery vehicles) and DNAs encoding antigens. DNA carriers protect DNA from degradation, and can facilitate DNA entry to specific tissues or cells and expression at an efficient level.

a. Adjuvants

Examples of immunological adjuvants that can be associated with the particles include, but are not limited to, TLR ligands, C-Type Lectin Receptor ligands, NOD-Like Receptor ligands, RLR ligands, and RAGE ligands. TLR ligands can include lipopolysaccharide (LPS) and derivatives thereof, as well as lipid A and derivatives thereof including, but not limited to, monophosphoryl lipid A (MPL), glycopyranosyl lipid A, PET-lipid A, and 3-O-desacyl-4'-monophosphoryl lipid A. In a specific embodiment, the immunological adjuvant is MPL. In another embodiment, the immunological adjuvant is LPS. TLR ligands can also include, but are not limited to, TLR3 ligands (e.g., polyinosinic-polycytidylic acid (poly(I:C)), TLR7 ligands (e.g., imiquimod and resiquimod), and TLR9 ligands.

b. Antigens

Antigens can be peptides, proteins, polysaccharides, saccharides, lipids, nucleic acids, or combinations thereof. The antigen can be derived from a virus, bacterium, parasite, plant, protozoan, fungus, tissue or transformed cell such as a cancer or leukemic cell and can be a whole cell or immunogenic component thereof, e.g., cell wall components or molecular components thereof.

Suitable antigens are known in the art and are available from commercial government and scientific sources. In one embodiment, the antigens are whole inactivated or attenuated organisms. These organisms may be infectious organisms, such as viruses, parasites and bacteria. These organisms may also be tumor cells. The antigens may be purified or partially purified polypeptides derived from tumors or viral or bacterial sources. The antigens can be recombinant polypeptides produced by expressing DNA encoding the polypeptide antigen in a heterologous expression system. The antigens can be DNA encoding all or part of an antigenic protein. The DNA may be in the form of vector DNA such as plasmid DNA.

Antigens may be provided as single antigens or may be provided in combination. Antigens may also be provided as complex mixtures of polypeptides or nucleic acids.

i. Viral Antigens

A viral antigen can be isolated from any virus including, but not limited to, a virus from any of the following viral families: Arenaviridae, Arterivirus, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae, Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenzavirus A and B and C), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxviridae (e.g., vaccinia and smallpox virus), Reoviridae (e.g., rotavirus), Retroviridae (e.g., lentivirus, such as human immunodeficiency virus (HIV) 1 and HIV 2), Rhabdoviridae (for example, rabies virus, measles virus, respiratory syncytial virus, etc.), Togaviridae (for example, rubella virus, dengue virus, etc.), and Totiviridae. Suitable viral antigens also include all or part of Dengue protein M, Dengue protein E, Dengue D1NS1, Dengue D1NS2, and Dengue D1NS3.

Viral antigens may be derived from a particular strain such as a papilloma virus, a herpes virus, i.e. herpes simplex 1 and 2; a hepatitis virus, for example, hepatitis A virus (HAV), hepatitis B virus (HBV), hepatitis C virus (HCV), the delta hepatitis D virus (HDV), hepatitis E virus (HEV) and hepatitis G virus (HGV), the tick-borne encephalitis viruses; parainfluenza, varicella-zoster, cytomeglavirus, Epstein-Barr, rotavirus, rhinovirus, adenovirus, coxsackieviruses, equine encephalitis, Japanese encephalitis, yellow fever, Rift Valley fever, and lymphocytic choriomeningitis.

ii. Bacterial Antigens

Bacterial antigens can originate from any bacteria including, but not limited to, *Actinomyces, Anabaena, Bacillus, Bacteroides, Bdellovibrio, Bordetella, Borrella, Campylobacter, Caulobacter, Chlamydla, Chloroblum, Chromatium, Clostridium, Corynebacterium, Cytophaga, Deinococcus, Escherichia, Francisella, Halobacterium, Heliobacter, Haemophilus, Hemophilus influenza* type B (HIB), *Hyphomicrobium, Legionella, Leptspirosls, Listerla, Meningococcus* A, B and C, *Methanobacterlum, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus*, and *Treponema, Vibrio*, and *Yersinia*.

ii. Parasite Antigens

Parasite antigens can be obtained from parasites such as, but not limited to, an antigen derived from *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydlal trachomatls, Plasmodlum falclparum, Trypanosoma brucei, Entamoeba histolytica, Toxoplasma gondii, Trichomonas vaginalis* and *Schistosoma mansoni*. These include Sporozoan antigens, Plasmodian antigens, such as all or part of a Circumsporozoite protein, a Sporozoite surface protein, a liver stage antigen, an apical membrane associated protein, or a Merozoite surface protein.

iv. Allergens and Environmental Antigens

The antigen can be an allergen or environmental antigen, such as, but not limited to, an antigen derived from naturally occurring allergens such as pollen allergens (tree-, herb, weed-, and grass pollen allergens), insect allergens (inhalant, saliva and venom allergens), animal hair and dandruff allergens, and food allergens. Important pollen allergens from trees, grasses and herbs originate from the taxonomic orders of Fagales, Oleales, Pinales and platanaceae including i.a. birch (*Betula*), alder (*Alnus*), hazel (*Corylus*), hornbeam (*Carpinus*) and olive (*Olea*), cedar (*Cryptomeriaand Juniperus*), Plane tree (*Platanus*), the order of Poales including i.e. grasses of the genera *Lolium, Phleum, Poa, Cynodon, Dactylis, Holcus, Phalaris, Secale*, and Sorghum, the orders of Asterales and Urticales including i.a. herbs of the genera *Ambrosia, Artemisia*, and *Parietaria*. Other allergen antigens that may be used include allergens from house dust mites of the genus *Dermatophagoides* and *Euroglyphus*, storage mite e.g. *Lepidoglyphys, Glycyphagus* and *Tyrophagus*, those from cockroaches, midges and fleas e.g. *Blatella, Periplaneta, Chironomus* and *Ctenocepphalides*, those from mammals such as cat, dog and horse, birds, venom allergens including such originating from stinging or biting insects such as those from the taxonomic order of Hymenoptera including bees (superfamily Apidae), wasps (superfamily Vespidea), and ants (superfamily Formicoidae). Still other allergen antigens that may be used include inhalation allergens from fungi such as from the genera *Alternaria* and *Cladosporium*.

v. Tumor Antigens

The antigen can be a tumor antigen, including a tumor-associated or tumor-specific antigen, such as, but not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, Triosephosphate isomeras, Bage-1, Gage 3,4,5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-I, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, and TPS.

4. Other Active Agents

Other active agents that can be loaded into, attached to the surface of, and/or enclosed within a delivery vehicle or administered in combination with a nanoparticulate composition include therapeutic, nutritional, diagnostic, and prophylactic agents. The active agents can be small molecule active agents or biomacromolecules, such as proteins, polypeptides, or nucleic acids. Suitable small molecule active agents include organic and organometallic compounds. The small molecule active agents can be hydrophilic, hydrophobic, or amphiphilic compounds.

Exemplary diagnostic agents include paramagnetic molecules, fluorescent compounds, magnetic molecules, and radionuclides, x-ray imaging agents, and contrast agents.

In certain embodiments, the delivery vehicle includes one or more anti-cancer agents. Representative anti-cancer agents include, but are not limited to, alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and decetaxel and *vinca* alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), topoisomerase inhibitors (including camptothecins such as camptothecin, irinotecan, and topotecan as well as derivatives of epipodophyllotoxins such as amsacrine, etoposide, etoposide phosphate, and teniposide), antibodies to vascular endothelial growth factor (VEGF) such as bevacizumab (AVASTIN®), other anti-VEGF compounds; thalidomide (THALOMID®) and derivatives thereof such as lenalidomide (REVLIMID®); endostatin; angiostatin; receptor tyrosine kinase (RTK) inhibitors such as sunitinib (SUTENT®); tyrosine kinase inhibitors such as sorafenib (Nexavar®), erlotinib (Tarceva®), pazopanib, axitinib, and lapatinib; transforming growth factor-α or transforming growth factor-β inhibitors, and antibodies to the epidermal growth factor receptor such as panitumumab (VECTIBIX®) and cetuximab (ERBITUX®).

In preferred embodiments, particularly those for treating cancer, one or more of the active agents can be a chemotherapeutic agent that has immune signaling properties.

5. Targeting Moieties

One or more targeting moieties (also referred to herein as targeting molecules) can be loaded into, attached to the surface of, and/or enclosed within the delivery vehicle. Preferably, the targeting moiety is displayed on the exterior surface of the delivery vehicle.

Exemplary target molecules include proteins, peptides, nucleic acids, lipids, saccharides, or polysaccharides that bind to one or more targets associated with an organ, tissue, cell, or extracellular matrix, or specific type of tumor or infected cell. The degree of specificity with which the delivery vehicles are targeted can be modulated through the selection of a targeting molecule with the appropriate affinity and specificity. For example, antibodies are very specific. These can be polyclonal, monoclonal, fragments, recombinant, or single chain, many of which are commercially available or readily obtained using standard techniques. T-cell specific molecules and antigens which are bound by antigen presenting cells as well as tumor targeting molecules can be bound to the surface of the nanolipogel and/or to the host molecule. The targeting molecules may be conjugated to the terminus of one or more PEG chains present on the surface of the particle.

In some embodiments, the targeting moiety is an antibody or antigen binding fragment thereof that specifically recognizes a tumor marker that is present exclusively or in elevated amounts on a malignant cell (e.g., a tumor antigen). Suitable targeting molecules that can be used to direct nanoparticles to cells and tissues of interest, as well as methods of conjugating target molecules to nanoparticles, are known in the art. See, for example, Ruoslahti, et al. *Nat. Rev. Cancer*, 2:83-90 (2002). Exemplary tumor antigens that can be targeted with antigen binding molecules such as antibodies are discussed above with respect to vaccine antigens.

Targeting molecules can also include neuropilins and endothelial targeting molecules, integrins, selectins, and adhesion molecules.

In some embodiments, the targeting moiety targets the particle to antigen-presenting cells (APCs), and particularly to a subclass of APCs known as dendritic cells. Dendritic cells express a number of cell surface receptors that can mediate endocytosis. Targeting exogenous antigens to internalizing surface molecules on systemically-distributed antigen presenting cells facilitates uptake of the particle and can overcomes a major rate-limiting step in the therapy.

Dendritic cell targeting molecules include monoclonal or polyclonal antibodies or fragments thereof that recognize and bind to epitopes displayed on the surface of dendritic cells. Dendritic cell targeting molecules also include ligands which bind to a cell surface receptor on dendritic cells. One such receptor, the lectin DEC-205, has been used in vitro and in mice to boost both humoral (antibody-based) and cellular (CD8 T cell) responses by 2-4 orders of magnitude (Hawiger, et al., J. Exp. Med., 194(6):769-79 (2001); Bonifaz, et al., *J. Exp. Med.*, 196(12): 1627-38 (2002); Bonifaz, et al., *J. Exp. Med.,* 199(6):815-24 (2004)). In these experiments, antigens were fused to an anti-DEC205 heavy chain and a recombinant antibody molecule was used for immunization.

A variety of other endocytic receptors, including a mannose-specific lectin (mannose receptor) and IgG Fc receptors, have also been targeted in this way with similar enhancement of antigen presentation efficiency. Other suitable receptors which may be targeted include, but are not limited to, DC-SIGN, 33D1, SIGLEC-H, DCIR, CD11c, heat shock protein receptors and scavenger receptors.

Other receptors which may be targeted include the toll-like receptors (TLRs). TLRs recognize and bind to pathogen-associated molecular patterns (PAMPs). PAMPs target the TLR on the surface of the dendritic cell and signals internally, thereby potentially increasing DC antigen uptake, maturation and T-cell stimulatory capacity. PAMPs conjugated to the particle surface or co-encapsulated include unmethylated CpG DNA (bacterial), double-stranded RNA (viral), lipopolysacharride (bacterial), peptidoglycan (bacterial), lipoarabinomannin (bacterial), zymosan (yeast), mycoplasmal lipoproteins such as MALP-2 (bacterial), flagellin (bacterial) poly(inosinic-cytidylic) acid (bacterial), lipoteichoic acid (bacterial) or imidazoquinolines (synthetic).

Targeting molecules can be covalently bound to delivery vehicles using a variety of methods known in the art. In preferred embodiments the targeting moiety is attached to the delivery vehicle by PEGylation or a biotin-avidin bridge.

a. CD40 Agonist

In a particular embodiment, the targeting moiety targets CD40. The moiety can be a CD40 agonist. The cell surface molecule CD40 is a member of the tumor necrosis factor receptor superfamily and is broadly expressed by immune, hematopoietic, vascular, epithelial, and other cells, including a wide range of tumor cells Vonderheide, *Clin Cancer Res,* 13(4):1083-1088 (2007). As a potential target for cancer therapy, CD40 may mediate tumor regression through both an indirect effect of immune activation and a direct cytotoxic effect on the tumor, resulting in a "two-for-one" mechanism of action of CD40 agonists. CD40 agonists are known in the art and reviewed in Vonderheide, *Clin Cancer Res,* 13(4): 1083-1088 (2007). Exemplary agonists include, but are not limited to recombinant CD40L (recombinant human trimer), CD-870, 893 (fully human IgG2 mAb), SGN-40 (humanized IgG1), and HCD 122 (fully human IgG mAb). Soluble agonistic CD40 antibodies have been shown to substitute for T-cell help provided by CD4+ lymphocytes in murine models of T cell-mediated immunity (Khalil, et al., *Update Cancer Ther.,* 2:61-65 (2007)). In a preferred embodiment, the targeting moiety is an agonistic anti-CD40 antibody, CD40 ligand or antigen binding fragment thereof.

b. Integrin Ligand

In another embodiment, the targeting moiety is a ligand for an integrin. Studies show that integrins are overexpressed on the surface of tumor cells and can thus serve as a marker that distinguishes between tumor cells and normal cells. Certain integrins also activate TGF-β through an extracellular pathway. After latent TGF-β is released from a tumor cell, it binds with integrin on the surface of the tumor cell, leading to the activation of the latent TGF-β. Increased TGF-β concentrations in the tumor microenvironment support immune suppression and recruit regulatory T cells to the tumor environment.

RGD peptide can serve a dual function: it is not only a typical integrin-targeting ligand (Ruoslahti E., et al., *Annu. Rev. Cell Dev. Biol.,* 12:697-715 (1996)) but also serves as an immune danger signal, activating APCs (Altincicek, et al., *Biol Chem.,* 390, 1303-11 (2009)). Therefore, in a preferred embodiment, RGD peptide is loaded into, attached to the surface of, and/or enclosed within the delivery vehicle.

c. T Cell Receptor that Recognizes the p53 Antigen

In a particular embodiment, the targeting moiety is a T cell receptor (TCR) that recognizes the p53 antigen within the context of human MHC. T cell receptor recombinant proteins derived from bacterial, eukoryatic or yeast cells including T cell receptors composed of the alpha, beta chains or gamma/delta chains (α/βTCR or γ/δ TCRs). For example, the full length ectodomains conserved sequence derived from rhesus monkey TCR α (TCRAR2 5'CCCOGGC-CACTTTCAGGAGGAGG-3') (SEQ ID NO: 1) and β (TCRBR 5'-GTCCTGTCTGCAC-CATCCTC-3') (SEQ ID NO:2).

d. IL-15/IL-15Rα

In another embodiment, the targeting moiety is an IL-15/IL-15Rα complex. Interleukin-15 (IL-15) is a cytokine that shares certain receptor subunits with IL-2 and thus has some overlapping mechanisms of action. IL-15 is expressed by dendritic cells and provides a critical signal for the proliferation and priming of natural killer (NK) cells. Accordingly, IL-15/IL-15Rα complex can be used to target nanoparticulate compositions to, for example, natural killer (NK) cells.

```
Human IL-15:
                                          (SEQ ID NO: 3)
MRISKPHLRS ISIQCYLCLL LNSHFLTEAG IHVFILGCFS

AGLPKTEANWVNVISDLKKI EDLIQSMHID ATLYTESDVH

PSCKVTAMKC FLLELQVISLESGDASIHDT VENLIILANN

SLSSNGNVTE SGCKECEELE EKNIKEFLQSFVHIVQMFIN TS

Human IL-15 receptor:
                                          (SEQ ID NO: 4)
MAPRRARGCRTLGLPALLLLLLLRPPATRGITCPPPMSVEHADIWVK

SYSLYSRERYICNSGFKRKAGTSSLTECVLNKATNVAHWTTPSLKCIR

DPALVHQRPAPPSTVTTAGVTPQPESLSPSGKEPAASSPSSNNTAATT

AAIVPGSQLMPSKSPSTGTTEISSHESSHGTPSQTTAKNWELTASASH

QPPGVYPQGHSDTTVAISTSTVLLCGLSAVSLLACYLKSRQTPPLASV

EMEAMEALPVTWGTSSRDEDLENCSHHL
```

C. Host Molecules

Host molecules are molecules or materials which reversibly associate with an active agent to form a complex. By virtue of their ability to reversibly form complexes with active agents, host molecules can function to control the release of a complexed active agent in vivo.

In some cases, the host molecule is a molecule that forms an inclusion complex with an active agent. Inclusion complexes are formed when an active agent (i.e., the guest) or portion of an active agent inserts into a cavity of another molecule, group of molecules, or material (i.e., the host). Typically, the guest molecule associates with the host molecule without affecting the framework or structure of the host. For example, in the case of inclusion complexes, the size and shape of the available cavity in the host molecule remain substantially unaltered as a consequence of complex formation.

The host molecule may be a small molecule, an oligomer, a polymer, or combinations thereof. Exemplary hosts include polysaccharides such as amyloses, cyclodextrins, and other cyclic or helical compounds containing a plurality of aldose rings, for example, compounds formed through 1,4 and 1,6 bonding of monosaccharides (such as glucose, fructose, and galactose) and disaccharides (such as sucrose, maltose, and lactose). Other exemplary host compounds include cryptands, cryptophanes, cavitands, crown ethers, dendrimers, ion-exchange resins, calixarenes, valinomycins, nigericins, catenanes, polycatenanes, carcerands, cucurbiturils, and spherands.

In still other embodiments, organic host compounds or materials include carbon nanotubes, fullerenes, and/or grapheme-based host materials. Carbon nanotubes (CNTs) are allotropes of carbon with a cylindrical nanostructure. Nanotubes are members of the fullerene structural family, which also includes the spherical buckyballs, and the ends of a nanotube may be capped with a hemisphere of the buckyball structure. Their name is derived from their long, hollow structure with the walls formed by one-atom-thick sheets of carbon, called graphene. These sheets are rolled at specific and discrete ("chiral") angles, and the combination of the rolling angle and radius decides the nanotube properties. Nanotubes can be categorized as single-walled nanotubes (SWNTs) and multi-walled nanotubes (MWNTs). Nanotubes and/or fullerenes can serve as hosts, for example, by encapsulating or entrapping the material to be delivered (i.e., the guest) within the tubes or fullerenes. Alternatively, the exterior and/or interior of the tubes and/or fullerenes can be functionalized with functional groups which can complex to the guest to be delivered. Complexations include, but are not limited to, ionic interactions, hydrogen bonding, Van der Waals interactions, and pi-pi interactions, such as pi-stacking.

Graphenes are also an allotrope of carbon. The structure of graphene is a one-atom-thick planar sheet of $sp^2$-bonded carbon atoms that are densely packed in a honeycomb crystal lattice. Graphene is the basic structural element of some carbon allotropes including graphite, charcoal, carbon nanotubes and fullerenes. The guest to be delivered can associate with and/or complex to graphene or functionalized graphene as described above for nanotubes and fullerenes.

The host material can also be an inorganic material, including but not limited to, inorganic phosphates and silica.

Suitable host molecules are generally selected for incorporation into nanolipogels or nanoparticles in view of the identity of the active agent(s) to be delivered and the desired drug release profile. In order to form a complex with the active agent being delivered, the host molecule is generally selected to be complimentary to the active agent both in terms of sterics (size) and electronics (charge and polarity). For example, in the case of host molecules that form inclusion complexes with the active agent to be delivered, the host molecule will typically possess an appropriately-sized cavity to incorporate the active agent. In addition, the host molecule typically possesses a cavity of appropriate hydrophobicity/hydrophilicity to promote complex formation with the active agent. The strength of the guest-host interaction will influence the drug release profile of the active agent from the nanolipogel or nanoparticle, with stronger guest-host interactions generally producing more prolonged drug release.

Generally, the host molecules are dispersed within the polymeric matrix that forms the nanolipogel or nanoparticle core. In some cases, one or more host molecules are covalently coupled to the polymeric matrix. For example, the host molecules may be functionalized with one or more pendant reactive functional groups that react with the polymer matrix. In particular embodiments, the host molecules contain one or more pendant reactive functional groups that react with the polymer matrix to crosslink the polymer matrix. Examples of suitable reactive functional groups include methacrylates, acrylates, vinyl groups, epoxides, thiiranes, azides, and alkynes.

In certain embodiments, the host molecule is a cyclodextrin. Cyclodextrins are cyclic oligosaccharides containing six (α-cyclodextrin), seven (β-cyclodextrin), eight (γ-cyclodextrin), or more α-(1,4)-linked glucose residues. The hydroxyl groups of the cyclodextrins are oriented to the outside of the ring while the glucosidic oxygen and two rings of the non-exchangeable hydrogen atoms are directed towards the interior of the cavity. As a result, cyclodextrins possess a hydrophobic inner cavity combined with a hydrophilic exterior. Upon combination with a hydrophobic active agent, the active agent (I.e., the guest) inserts into the hydrophobic interior of the cyclodextrin (i.e., the host).

The cyclodextrin may be chemically modified such that some or all of the primary or secondary hydroxyl groups of the macrocycle, or both, are functionalized with one or more pendant groups. The pendant groups may be reactive functional groups that can react with the polymeric matrix, such as methacrylates, acrylates, vinyl groups, epoxides, thiiranes, azides, alkynes, and combinations thereof. The pendant groups may also serve to modify the solubility of the cyclodextrin. Exemplary groups of this type include sulfinyl, sulfonyl, phosphate, acyl, and $C_1$-$C_{12}$ alkyl groups optionally substituted with one or more (e.g., 1, 2, 3, or 4) hydroxy, carboxy, carbonyl, acyl, oxy, and oxo groups. Methods of modifying these alcohol residues are known in the art, and many cyclodextrin derivatives are commercially available.

Examples of suitable cyclodextrins include α-cyclodextrin; β-cyclodextrin; γ-cyclodextrin; methyl α-cyclodextrin; methyl β-cyclodextrin; methyl γ-cyclodextrin; ethyl β-cyclodextrin; butyl α-cyclodextrin; butyl β-cyclodextrin; butyl γ-cyclodextrin; pentyl γ-cyclodextrin; hydroxyethyl β-cyclodextrin; hydroxyethyl γ-cyclodextrin; 2-hydroxypropyl α-cyclodextrin; 2-hydroxypropyl β-cyclodextrin; 2-hydroxypropyl γ-cyclodextrin; 2-hydroxybutyl β-cyclodextrin; acetyl α-cyclodextrin; acetyl β-cyclodextrin; acetyl γ-cyclodextrin; propionyl β-cyclodextrin; butyryl β-cyclodextrin; succinyl α-cyclodextrin; succinyl β-cyclodextrin; succinyl γ-cyclodextrin; benzoyl β-cyclodextrin; palmityl β-cyclodextrin; toluenesulfonyl β-cyclodextrin; acetyl methyl β-cyclodextrin; acetyl butyl β-cyclodextrin; glucosyl α-cyclodextrin; glucosyl β-cyclodextrin; glucosyl γ-cyclodextrin; maltosyl α-cyclodextrin; maltosyl β-cyclodextrin; maltosyl γ-cyclodextrin; α-cyclodextrin carboxymethylether; β-cyclodextrin carboxymethylether; γ-cyclodextrin carboxymethylether; carboxymethylethyl β-cyclodextrin; phosphate ester α-cyclodextrin; phosphate ester β-cyclodextrin; phosphate ester γ-cyclodextrin; 3-trimethylammonium-2-hydroxypropyl β-cyclodextrin; sulfobutyl ether β-cyclodextrin; carboxymethyl α-cyclodextrin; carboxymethyl β-cyclodextrin; carboxymethyl γ-cyclodextrin, and combinations thereof.

Preferred cyclodextrins include α-cyclodextrins, β-cyclodextrins, and γ-cyclodextrins functionalized with one or more pendant acrylate or methacrylate groups. In a particular embodiment, the host molecule is a β-cyclodextrin functionalized with multiple methacrylate groups. An exemplary host molecule of this type is illustrated below, wherein R represents a $C_1$-$C_6$ alkyl group.

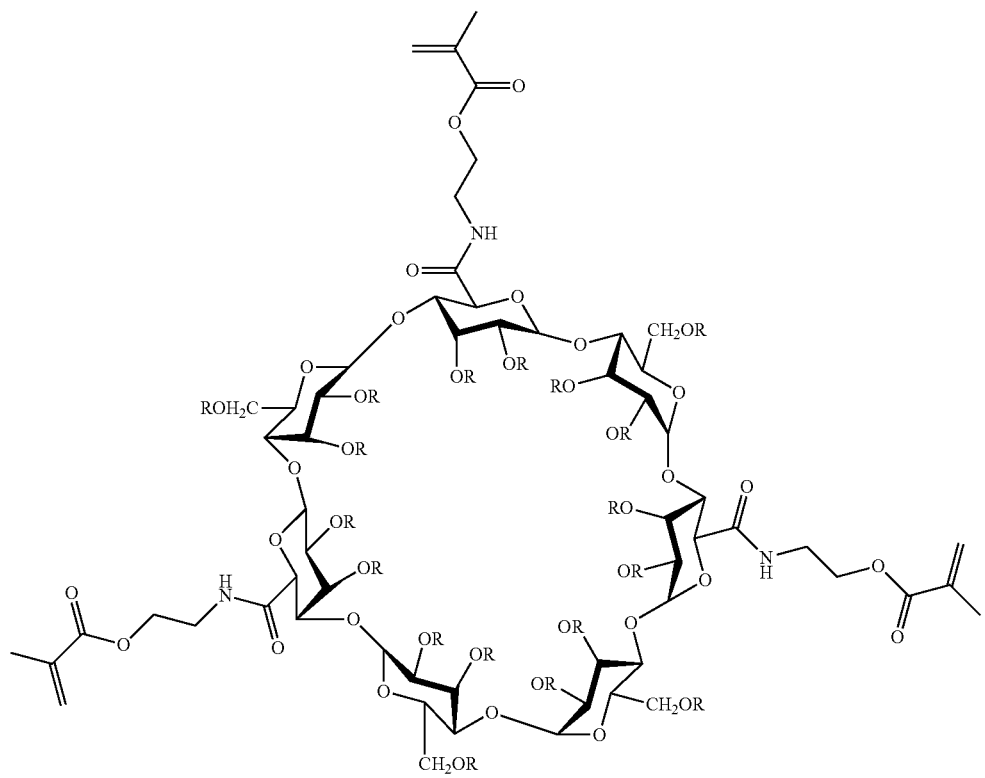

As a further example, the host molecule may also be a material that temporarily associates with an active agent via ionic interactions. For example, conventional ion exchange resins known in the art for use in controlled drug release may serve as host molecules. See, for example, Chen, et al. "Evaluation of ion-exchange microspheres as carriers for the anticancer drug doxorubicin: in vitro studies." *J. Pharm. Pharmacol.* 44(3):211-215 (1992) and Farag, et al. "Rate of release of organic carboxylic acids from ion exchange resins" *J. Pharm. Sci.* 77(10):872-875(1988).

By way of exemplification, when the active agent being delivered is a cationic species, suitable ion exchange resins may include a sulfonic acid group (or modified sulfonic acid group) or an optionally modified carboxylic acid group on a physiologically acceptable scaffold. Similarly, where the active agent is an anionic species, suitable ion exchange resins may include amine-based groups (e.g., trimethylamine for a strong interaction, or dimethylethanolamine for a weaker interaction). Cationic polymers, such as polyethyleneimine (PEI), can function as host molecules for complex oligonucleotides such as siRNA.

In other cases, the host molecule is a dendrimer, such as a poly(amidoamine) (PAMAM) dendrimer. Cationic and anionic dendrimers can function as host materials by ionically associating with active agents, as described above. In addition, medium-sized dendrimers, such as three- and four-generation PAMAM dendrimers, may possess internal voids spaces which can accommodate active agents, for example, by complexation of nucleic acids.

In some embodiments the host molecule is a dendrimer conjugated to a cyclodextrin. In some embodiments, the cyclodextrin(s) shields primary amines of dendrimer. Suitable dendrimers and cyclodextrins are discussed above. Unmodified dendrimer (i.e., generation 4 PAMAM dendrimer (G4)) was empirically better at endosomal disruption than dendrimer conjugated with cyclodexrin (CD) (See the Examples below). Without being bound by theory, it is believed that terminal amine groups on PAMAM dendrimers provide endosomal buffering and disrupt endosomes by the proton sponge effect. Accordingly, increasing CD results in a decrease in endosomal disruption. As discussed in the Examples below, different combinations of dendrimers and cyclodextrins can be used to modulate the transfection efficiency and level of endosomal disruption in the cell.

Preferably, the one or more host molecules are present in an amount of from about 0.1% to about 40% w/w of the polymeric matrix, more preferably from about 0.1% to about 25% w/w of the overall formulation.

III. Methods of Manufacture, Loading, and Pharmaceutical Compositions

A. Methods of Manufacture and Loading

1. Nanolipogels

A nanolipogel is a nanoparticle that combines the advantages of both liposomes and polymer-based particles for sustained delivery of nucleic acids, proteins and/or small molecules. The nanolipogel can be in the form of spheres, discs, rods or other geometries with different aspect ratios. The nanosphere can be larger, i.e., microparticles. The nanolipogel is typically formed of synthetic or natural polymers capable of encapsulating agents by remote loading and tunable in properties so as to facilitate different rates of release. Release rates are modulated by varying the polymer to lipid ratio from 0.05 to 5.0, more preferably from 0.5 to 1.5.

Nanolipogels are designed to be loaded with agents either prior to, during or after formation and subsequently function as controlled-release vehicles for the agents. The nanolipogel can be loaded with more than one agent such that controlled release of the multiplicity of agents is subsequently achieved.

The nanolipogel is loaded with one or more first agents during formation and one or more second agents following formation by the process of rehydration of the nanolipogel in the presence of the second agents. For example, the nanolipogel is loaded with a molecule that serves as an adjuvant and the nanolipogel thereafter incorporates one or more target antigens after formation, for the controlled release of adjuvant together with the antigens.

2. Polymeric Nanoparticles a. Emulsion Method

In some embodiments, the polymeric nanoparticle is prepared using an emulsion solvent evaporation method. For example, a polymeric material is dissolved in a water immiscible organic solvent and mixed with a drug solution or a combination of drug solutions. The water immiscible organic solvent can be, but is not limited to, one or more of the following: chloroform, dichloromethane, and acyl acetate. The drug can be dissolved in, but is not limited to, one or more of the following: acetone, ethanol, methanol, isopropyl alcohol, acetonitrile and dimethyl sulfoxide (DMSO). An aqueous solution is then added into the resulting mixture solution to yield emulsion solution by emulsification. The emulsification technique can be, but is not limited to, probe sonication or homogenization through a homogenizer. The peptides or fluorophores or drugs may be associated with the surface of, encapsulated within, surrounded by, and/or distributed throughout, the polymeric matrix of the particle.

b. Nanoprecipitation Method

In another embodiment, the polymeric nanoparticles are prepared using nanoprecipitation methods or microfluidic devices. A polymeric material is mixed with a drug or drug combinations in a water miscible organic solvent.

The resulting mixture solution is then added to an aqueous solution to yield a nanoparticle solution.

c. Exemplary Methods of Preparation

Particles can be fabricated from different polymers using a variety of methods that and can be selected based on criteria including the polymeric composition of the particle, the agent(s) being loaded into or associated with the particle according to method that are known in the art. Exemplary methods are provided below.

a. Solvent Evaporation. In this method the polymer is dissolved in a volatile organic solvent, such as methylene chloride. The drug (either soluble or dispersed as fine particles) is added to the solution, and the mixture is suspended in an aqueous solution that contains a surface active agent such as poly(vinyl alcohol). The resulting emulsion is stirred until most of the organic solvent evaporated, leaving solid particles. The resulting particles are washed with water and dried overnight in a lyophilizer. Particles with different sizes (0.5-1000 microns) and morphologies can be obtained by this method. This method is useful for relatively stable polymers like polyesters and polystyrene.

However, labile polymers, such as polyanhydrides, may degrade during the fabrication process due to the presence of water. For these polymers, the following two methods, which are performed in completely anhydrous organic solvents, are more useful.

b. Hot Melt Microencapsulation. In this method, the polymer is first melted and then mixed with the solid particles. The mixture is suspended in a non-miscible solvent (like silicon oil), and, with continuous stirring, heated to 5° C. above the melting point of the polymer. Once the emulsion is stabilized, it is cooled until the polymer particles solidify. The resulting particles are washed by decantation with petroleum ether to give a free-flowing powder. Particles with sizes between 0.5 to 1000 microns are obtained with this method. The external surfaces of spheres prepared with this technique are usually smooth and dense. This procedure is used to prepare particles made of polyesters and polyanhydrides. However, this method is limited to polymers with molecular weights between 1,000-50,000.

c. Solvent Removal. This technique is primarily designed for polyanhydrides. In this method, the drug is dispersed or dissolved in a solution of the selected polymer in a volatile organic solvent like methylene chloride. This mixture is suspended by stirring in an organic oil (such as silicon oil) to form an emulsion. Unlike solvent evaporation, this method can be used to make particles from polymers with high melting points and different molecular weights. Particles that range between 1-300 microns can be obtained by this procedure. The external morphology of spheres produced with this technique is highly dependent on the type of polymer used.

d. Spray-Driving. In this method, the polymer is dissolved in organic solvent. A known amount of the active drug is suspended (insoluble drugs) or co-dissolved (soluble drugs) in the polymer solution. The solution or the dispersion is then spray-dried. Typical process parameters for a mini-spray drier (Buchi) are as follows: polymer concentration=0.04 g/mL, inlet temperature=−24° C., outlet temperature=β-15° C., aspirator setting=15, pump setting=10 mL/minute, spray flow=600 NI/hr, and nozzle diameter=0.5 mm. Microparticles ranging between 1-10 microns are obtained with a morphology which depends on the type of polymer used.

e. Hydrogel Particles. Particles made of gel-type polymers, such as alginate, are produced through traditional ionic gelation techniques. The polymers are first dissolved in an aqueous solution, mixed with barium sulfate or some bioactive agent, and then extruded through a microdroplet forming device, which in some instances employs a flow of nitrogen gas to break off the droplet. A slowly stirred (approximately 100-170 RPM) ionic hardening bath is positioned below the extruding device to catch the forming microdroplets. The particles are left to incubate in the bath for twenty to thirty minutes in order to allow sufficient time for gelation to occur. Particle size is controlled by using various size extruders or varying either the nitrogen gas or polymer solution flow rates. Chitosan particles can be prepared by dissolving the polymer in acidic solution and crosslinking it with tripolyphosphate. Carboxymethyl cellulose (CMC) particles can be prepared by dissolving the polymer in acid solution and precipitating the particle with lead ions. In the case of negatively charged polymers (e.g., alginate, CMC), positively charged ligands (e.g., polylysine, polyethyleneimine) of different molecular weights can be ionically attached.

B. Pharmaceutical Compositions

Pharmaceutical compositions can be for administration by parenteral (intramuscular, intraperitoneal, intravenous (IV) or subcutaneous injection), by instillation, or in a depo, formulated in dosage forms appropriate for each route of administration.

In some embodiments, the compositions are administered systemically, for example, by intravenous or intraperitoneal administration, in an amount effective for delivery of the compositions to targeted cells. Other routes include instillation or mucosal.

In certain embodiments, the compositions are administered locally, for example, by injection directly into a site to be treated. In some embodiments, the compositions are injected or otherwise administered directly to one or more tumors or diseased tissues. Typically, local injection causes an increased localized concentration of the compositions which is greater than that which can be achieved by systemic administration. In some embodiments, the compositions are delivered locally to the appropriate cells by using a catheter or syringe. Other means of delivering such compositions locally to cells include using infusion pumps or incorporating the compositions into polymeric implants which can effect a sustained release of the compositions to the immediate area of the implant.

The compositions can be provided to the cells either directly, such as by contacting it with the cell, or indirectly, such as through the action of any biological process. For example, the compositions can be formulated in a physiologically acceptable carrier or vehicle, and injected into a tissue or fluid surrounding the cell. The compositions can cross the cell membrane by simple diffusion, endocytosis, or by any active or passive transport mechanism.

The selected dosage depends upon the desired therapeutic effect, on the route of administration, and on the duration of the treatment desired. Generally, nanoparticulate compositions can be administered in a range of about 0001 mg/kg to 100 mg/kg per administration (e.g., daily; or 2, 3, 4, 5 or more times weekly; or 2, 3, 4, 5 or more times a month, etc., as discussed in more detail below). The route of administration can be a consideration in determining dosage as well. For example, in a particular embodiment, a nanoparticulate composition is administered in a range of 0.01 mg/kg to 100 mg/kg (e.g., daily; or 2, 3, 4, 5 or more times weekly; or 2, 3, 4, 5 or more times a month, etc., as discussed in more detail below) by intravenous or interpretational routes, or in a range of 0.0001 mg/kg to 1 mg/kg (e.g., daily; or 2, 3, 4, 5 or more times weekly; or 2, 3, 4, 5 or more times a month, etc., as discussed in more detail below) for a subcutaneous route (e.g., local injection into or adjacent to the tumor or tumor microenvironment). More exemplary dosage are discussed below.

1. Formulations for Parenteral Administration

In a preferred embodiment the compositions are administered in an aqueous solution, by parenteral injection. The formulation can be in the form of a suspension or emulsion. In general, pharmaceutical compositions are provided including effective amounts of one or more active agents optionally include pharmaceutically acceptable diluents, preservatives, solubilizers, emulsifiers, adjuvants and/or carriers. Such compositions can include diluents such as sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and resuspended immediately before use. The formulation may be sterilized by, for example, filtration through a bacteria retaining filter, by incorporating sterilizing agents into the compositions, by irradiating the compositions, or by heating the compositions.

2. Formulations for Topical, Mucosal, and Oral Administration

The compositions can be applied topically or by instillation. Topical administration can include application to the lungs, nasal, oral (sublingual, buccal), vaginal, or rectal mucosa. These methods of administration can be made effective by formulating the shell with mucosal transport elements. Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art.

Formulations for administration to the mucosa will typically be spray dried drug particles, which may be incorporated into a tablet, gel, capsule, suspension or emulsion. Standard pharmaceutical excipients are available from any formulator.

Oral formulations may be in the form of chewing gum, gel strips, tablets, capsules, or lozenges. Oral formulations may include excipients or other modifications to the particle which can confer enteric protection or enhanced delivery through the GI tract, including the intestinal epithelia and mucosa (see Samstein, et al. *Biomaterials.* 0.29(6):703-8 (2008).

Transdermal formulations may also be prepared. These will typically be ointments, lotions, sprays, or patches, all of which can be prepared using standard technology. Transdermal formulations can include penetration enhancers. Chemical enhancers and physical methods including electroporation and microneedles can work in conjunction with this method.

IV. Methods of Treatment

A. Method of Stimulating or Enhancing an Immune Response

Nanoparticulate composition can be administered to a subject in need thereof in an effective amount to induce, enhance, or increase an immune response in the subject. Typically the immune response is an immune stimulating response. For example, the compositions can be administered in an amount effective to increase a cell (T-cell driven) immune response, a humoral (B-cell driven) immune response, T cell activity, and/or T cell proliferation, to reduce a T cell inhibitory signal, to enhance production of cytokines, to stimulate T cell differentiation or effector function, to promote survival of T cells, or any combination thereof.

In some embodiments, the compositions can reduce or inhibit an immune suppressive response. For example the compositions can be administered in an effective amount to deplete Tregs, block Treg differentiation, trafficking, and/or effector function, raises effector cell suppression threshold, or any combination thereof.

The delivery vehicles are particularly useful for simultaneous or ordered delivery of two or more active agents to the same target cell. For example, co-loading of two more active agents into or onto the same delivery vehicle could increase the likelihood that both agents will be delivered to the same target cell. The user can control which active agents are presented on the surface of the delivery vehicle and which are encapsulated therein. Therefore, the user can determine how and when each active agent is presented to the target cell (i.e., to a receptor on the exterior of the cell, intracellularly following endocytosis, etc.).

Co-delivery also allows for simultaneous targeting to two different pathways. For example, the nanoparticulate composition can induce or increase an immune stimulating response and simultaneously decrease or reduce an immune suppressive response. Typically such compositions include at least two active agents, the first of which increases an immune stimulating response and the second of which decreases an immune suppressive response. An exemplary composition includes a proinflammatory cytokine such as IL-2 and a TGF-β inhibitor such as SB505124 or losartan. In a further embodiment, the particles include a targeting moiety, for example, a tumor targeting moiety such as RGD peptide.

In another embodiment, each of the active agents is loaded into separate particles which are delivered to the subject together or separately, for example, when both agents do not need to act on the same cell or localized in the same microenvironment.

The nanoparticulate compositions disclosed herein can also be designed to emulate functional APC and T-helper cells, which can be depleted and/or ineffective in cancer patients. Immunity in humans is composed of two evolutionary responses—innate and adaptive. Presentation to APCs of triggering molecules, either foreign molecules or "self"-based molecules that are not normally presented to the immune system are important for both responses. These molecules, which have been collectively referred to as "danger signals", alert the immune system, particularly via APCs, to the presence of disease or situations likely to result in disease. Nanoparticles can be deployed to promote danger signaling and even to emulate activated APCs, serving as artificial APCs (aAPC's). In some specific embodiments, the particles are designed to mimic dendritic cells, or function as artificial dendritic cells. In a particular embodiment, the particles present IL-15/IL-15Rα complex on their surface.

The activity or effectiveness of a nanoparticle composition can be compared to a control. Suitable controls are known in the art. For example, a control can be the subject prior to treatment. The activity or effectiveness of the composition can be a change in a condition or symptom of the subject after treatment.

A control can also be a subject with the same conditions or symptoms treated in parallel with the same active agents in soluble form or in a different delivery vehicle. In some embodiments, less of the active agent is used, the active agent is administered less frequently, or a combination thereof compared to administration of the same active agent in soluble form or in a different delivery vehicle. For example, in some embodiments, 10, 25, 50, 75, 100, 500, 1,000, 5,000, or 10,000 fold less active agent is used in the nanoparticulate composition compared to active agent administered in the soluble form.

Typically, the disclosed nanoparticulate compositions show improved activity, effectiveness, or efficacy. For example, the therapeutic potency to vehicle delivered active agent(s) can exceed that of the agent(s) in the absence of the delivery vehicle. An improved therapeutic potency of the disclosed delivery vehicles can be due to an increase in avidity of the agent(s) for targets cells, simultaneous high local concentration of the two or more therapeutic agents, simultaneous damping of suppressive elements and enhancement of stimulatory elements of the immune system, selective targeting of stimulatory elements of the immune system, direct targeting of the disease cells, or any combination thereof.

B. Diseases to be Treated

The nanoparticulate compositions can be administered prophylactically or therapeutically to a subject in need thereof in an amount effective to prevent, delay, treat, or reduce the severity of a disease or disorder, or one or more symptoms thereof. The disclosed compositions offer the possibility of treatment and control of many diseases with drugs whose systemic half-lives and biodistribution are important and may be less effective or ineffective if administered in soluble form or otherwise absent a delivery vehicle.

The disease or disorder can be, for example, cancer or an infection.

1. Cancer

The disclosed compositions can be used to treat benign or malignant cancers, and tumors thereof. The treatment can directly target and kill cancer cells, indirectly target the cancer cells by increasing an immune response against the cancer cells; or a combination thereof.

In a mature animal, a balance usually is maintained between cell renewal and cell death in most organs and tissues. The various types of mature cells in the body have a given life span; as these cells die, new cells are generated by the proliferation and differentiation of various types of stem cells. Under normal circumstances, the production of new cells is so regulated that the numbers of any particular type of cell remain constant. Occasionally, though, cells arise that are no longer responsive to normal growth-control mechanisms. These cells give rise to clones of cells that can expand to a considerable size, producing a tumor or neoplasm. A tumor that is not capable of indefinite growth and does not invade the healthy surrounding tissue extensively is benign. A tumor that continues to grow and becomes progressively invasive is malignant. The term cancer refers specifically to a malignant tumor. In addition to uncontrolled growth, malignant tumors exhibit metastasis. In this process, small clusters of cancerous cells dislodge from a tumor, invade the blood or lymphatic vessels, and are carried to other tissues, where they continue to proliferate. In this way a primary tumor at one site can give rise to a secondary tumor at another site.

The disclosed compositions can delay or inhibit the growth of a tumor in a subject, reduce the growth or size of the tumor or eliminate it altogether, inhibit or reduce metastasis of the tumor, and/or inhibit or reduce symptoms associated with tumor development or growth. For example, in some embodiments, the compositions reduce tumor burden in the subject or slow or prevent tumor growth over time.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The types of cancer that can be treated with the provided compositions and methods include, but are not limited to, vascular cancers such as multiple myeloma, as well as solid cancers, including adenocarcinomas and sarcomas, of bone, bladder, brain, breast, cervix, colon, rectum, esophagus, kidney, liver, lung, nasopharynx, pancreas, prostate, skin, stomach, and uterus. In some embodiments, the disclosed compositions are used to treat multiple cancer types concurrently. The compositions can also be used to treat metastases or tumors at multiple locations.

Administration is not limited to the treatment of an existing tumor or infectious disease but can also be used to prevent or lower the risk of developing such diseases in an individual, i.e., for prophylactic use. Potential candidates for prophylactic vaccination include individuals with a high risk of developing cancer, i.e., with a personal or familial history of certain types of cancer.

2. Infections

The compositions can be used to stimulate an immune response in a subject suffering from an infection, for example a viral infection, bacterial infection, fungal infection or protozoan infection. Thus, one embodiment provides a method for treating infection by administering an effective amount of a nanoparticulate composition to increase an immune response against an infection.

Representative infections that can be treated, include but are not limited to infections cause by microoganisms including, but not limited to, *Actinomyces, Anabaena, Bacillus, Bacteroldes, Bdellovlbrlo, Bordetella, Borrelia, Campylobacter, Caulobacter, Chlamydia, Chlorobium, Chromatium, Clostridium, Corynebacterium, Cytophaga, Deinococcus, Escherlchla, Francisella, Halobacterlum, Hellobacter, Haemophllus, Hemophilus influenza* type B (HIB), *Hyphomicrobium, Legionella, Leptspirosis, Listeria, Meningococcus* A, B and C, *Methanobacterium, Micrococcus, Myobacterium, Mycoplasma, Myxococcus, Neisseria, Nltrobacter, Osclllatorla, Prochloron, Proteus, Pseudomonas, Phodospirillum, Rickettsia, Salmonella, Shigella, Spirillum, Spirochaeta, Staphylococcus, Streptococcus, Streptomyces, Suljolobus, Thermoplasma, Thiobacillus*, and *Treponema, Vibrio, Yersinia, Cryptococcus neoformans, Hlstoplasma capsulatum, Candida albicans, Candida tropicalls, Nocardla asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalls* and *Schistosoma mansoni*.

C. Exemplary Disease Treatment Strategies

Specific combinations of active agents are also disclosed herein and exemplified in the Examples below.

1. Proinflammatory Cytokine and TGF-β Inhibitor

One exemplary disease treatment strategy includes administration to a subject in need thereof of a nanoparticulate composition including a proinflammatory cytokine and a TGF-β inhibitor. The two agents can be loaded into or onto the same particle, or into or onto separate particles and co-administered. In a preferred embodiment, the proinflammatory cytokine and TGF-β inhibitor are loaded into or onto the same delivery vehicle, for example a nanolipogel or polymeric nanoparticle such as PLGA. The proinflammatory cytokine can be IL-2 or IFNγ and the TGF-β inhibitor can be SB505124 or losartan. In a particular embodiment, a nanolipogel or PLGA nanoparticle is co-loaded with recombinant IL-2 and losartan. In further embodiments, the delivery vehicle is decorated with a targeting moiety such as RGD.

Method of making nanoparticulate compositions containing proinflammatory cytokines and/or TGF-β inhibitors are discussed in more detail in the Examples below. For example, dosages of 0.5 mg to 5 mg have been tested in mouse. A preferred dosage range for these active agents is 0.01 mg/kg to 100 mg/kg of particles or nanolipogels by intravenous or intraperitoneal injection or infusion routes (e.g., daily; or 2, 3, 4, 5 or more times weekly; or 2, 3, 4, 5 or more times a month, etc., as discussed in more detail below); or 0.0001 mg/kg to 1 mg/kg by subcutaneous route (e.g., daily; or 2, 3, 4, 5 or more times weekly; or 2, 3, 4, 5 or more times a month, etc., as discussed in more detail below). It has been determined that 5 mg of nanolipogels loaded with IL-2 and losartan typically contain about 50 ng IL-2 and about 200 μg losartan.

2. Proinflammatory Cytokine and Targeting Moiety

Another exemplary disease treatment strategy includes administration to a subject in need thereof of a nanoparticulate composition including a targeting moiety and a proinflammatory cytokine. As discussed above, the targeting molecule can be, for example, RGD. In other embodiments, the targeting moiety is a T cell receptor (TCR) or an anti-CD40 agonist. Preferred proinflammatory cytokines are IL-2 or IFNγ.

In a particular embodiment, the targeting moiety is a T cell receptor (TCR) that recognizes the p53 antigen within the context of human MHC.

In another embodiment, the targeting moiety is a CD40 agonist, for example, an anti-CD40 antibody or antigen binding fragment thereof. Suitable CD40 agonists are known in the art and described above.

Accordingly, a delivery vehicle such as a nanolipogel or a nanoparticle such as a PLGA nanoparticle loaded with IL-2 and decorated with a T cell receptor (TCR) that recognizes the p53 antigen within the context of human MHC is disclosed. Also disclosed is a delivery vehicle such as a nanolipogel or a nanoparticle such as a PLGA nanoparticle loaded with IL-2 and decorated with a CD40 agonist. A nanolipogel or a nanoparticle such as a PLGA nanoparticle loaded with IFNγ, and decorated with a T cell receptor (TCR) that recognizes the p53 antigen within the context of human MHC or a CD40 agonist is also disclosed.

A preferred dosage for these active agents is a range of about 10 mg/kg to 100 mg/kg (e.g., daily; or 2, 3, 4, 5 or more times weekly; or 2, 3, 4, 5 or more times a month, etc., as discussed in more detail below).

3. IL-15/IL-15α

In some embodiments, the nanoparticulate compositions are designed to mimic APCs such as dendritic cells. Interleukin-15 (IL-15) is a cytokine that shares certain receptor subunits with IL-2 and thus has some overlapping mechanisms of action. IL-15 is expressed by dendritic cells and provides an important signal for the proliferation and priming of natural killer (NK) cells. IL-15 binds tightly to a receptor subunit not shared by IL-2, called IL-15Rα. IL-15Rα is capable of binding IL-15 independently of other subunits. It is believed that this property allows IL-15 to be produced by one cell, endocytosed by another cell, and then presented to a third cell. Soluble complexes of IL-15/IL-15Rα can be prepared displayed on delivery vehicles where they act like an artificial dendritic cell.

It is believed that multivalent presentation of IL-15/IL-15Rα complexes on the surface of delivery vehicles facilitates the adhesion of the particle to NK cells. In fact, IL-15/IL-15Rα complexes on nanoparticles expanded NK cells more effectively than IL-15 alone or soluble IL-15/IL-15Rα complexes (see Examples below). When stimulated with IL-15/IL-15Rα complexes on nanoparticles, these NK cells also demonstrate elevated levels of interferon-γ secretion even at nanoparticle concentrations that do not promote significant levels of cell division. IL-15/IL-15Rα complexes on nanoparticles also promote expansion of CD8$^+$ T cells.

Accordingly, in some embodiments, a nanolipogel or a nanoparticle such as a PLGA nanoparticle is decorated with IL-15/IL-15Rα complexes. The nanolipogel or a nanoparticle may be further loaded with one or more additional active agents. The one or more additional agents can be an anti-cancer agent or immunomodulator, for example, IL-2 or a TGF-β inhibitor such as losartan. In some embodiments, the nanolipogel or a nanoparticle is further loaded with one or more antigens or adjuvants, for example, a tumor antigen.

A preferred dosage these active agents is a range of about 1 mg/kg to 50 mg/kg, or about 1 mg/kg to 5 mg/kg; or about 10 mg/kg to 50 mg/kg; or 1-5 mg/kg-10-50 mg/kg (e.g., daily; or 2, 3, 4, 5 or more times weekly; or 2, 3, 4, 5 or more times a month, etc., as discussed in more detail below).

D. Adjuvant Strategies and Combination Therapies

In some embodiments, a nanoparticulate composition is used as an adjuvant and is co-administered in combination with an additional active agent that is not load onto or into the disclosed nanoparticulate composition. The adjuvant and combination therapies can include administration of the additional active agents together in the same admixture with the particles, or in separate admixtures.

In a preferred embodiment, one or more active agents (such as TGF-β inhibitor and/or a proinflammatory cytokine) is loaded into or onto nanolipogels or another delivery vehicle to form a nanoparticulate composition and administered to a subject in combination with one or more additional active agents which are in a free or soluble form or even part of a separate dosage unit.

In some embodiments, the pharmaceutical composition includes two, three, or more active agents, some of which are load into or onto particles and some of which are not.

The different active agents can have the same or different mechanisms of action. In some embodiments, the combination results in an additive effect on the treatment of the disease or disorder. In some embodiments, the combinations result in a more than additive effect on the treatment of the disease or disorder. For example, in particular embodiments, the nanoparticulate composition increases or improves an immune stimulating or immune enhancing therapy or a chemotherapeutic agent.

A nanoparticulate composition and one or more additional free or soluble active agents can be administered to a subject as part of a treatment regimen. Treatment regimen typically refers to a treatment of a disease or a method for achieving a desired physiological change or change in a symptom of the disease, such as increased or decreased response of the immune system to an antigen or immunogen, such as an increase or decrease in the number or activity of one or more cells, or cell types, that are involved in such response, wherein said treatment or method includes administering to an animal, such as a mammal, especially a human being, a sufficient amount of two or more chemical agents or components of said regimen to effectively treat the disease or to produce said physiological change or change in a symptom of the disease, wherein the chemical agents or components are administered together, such as part of the same composition, or administered separately and independently at the same time or at different times (i.e., administration of each agent or component is separated by a finite period of time from one or more of the agents or components). Preferably, administration of the one or more agents or components achieves a result greater than that of any of the agents or components when administered alone or in isolation. Preferably, one or more of the active agents is in a nanoparticulate composition.

Nanoparticulate compositions and/or additional active agent(s) can be administered together or separately on a daily basis for a finite time period, such as up to 3 days, or up to 5 days, or up to 7 days, or up to 10 days, or up to 15 days or up to 20 days or up to 25 days, are all specifically contemplated by the invention. In some embodiments, the nanoparticulate composition and/or additional active agent(s) is administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. In some embodiments, the frequency of administration is once weekly, or is once every two weeks, or is once every four weeks, or is twice every week. In some embodiments, a single administration is effective. In some embodiments two or more administrations are needed.

All such administrations of the nanoparticulate composition may occur before or after administration of the additional active agent(s). Alternatively, administration of one or more doses of active agent(s) may be temporally staggered with the administration of the nanoparticulate composition to form a uniform or non-uniform course of treatment whereby one or more doses of active agent(s) are administered, followed by one or more doses of nanoparticulate composition, followed by one or more doses of additional active agent(s); or vice versa, all according to whatever schedule is selected or desired by the researcher or clinician administering the agents.

In some embodiments the nanoparticulate composition is administered at least 1, 2, 3, 5, 10, 15, 20, 24 or 30 hours prior to or after administering of the additional active agent(s). In other embodiments, the additional active agent(s) is administered at least 1, 2, 3, 5, 10, 15, 20, 24 or 30 hours prior to or after administering of the nanoparticulate composition.

In an exemplary strategy, a subject in need thereof is administered a nanoparticulate composition including a proinflammatory cytokine and/or a TGF-β inhibitor in combination with one or more additional immune response stimulating or enhancing agents. The proinflammatory cytokine and/or TGF-β inhibitor agents can be loaded into or onto the same particle, or into or onto separate particles and co-administered. In some embodiments, only nanolipogels or particles including a proinflammatory cytokine, or including a TGF-β inhibitor is administered to the subject in the absence of the other. In a preferred embodiment, the proinflammatory cytokine and TGF-β inhibitor are loaded into or onto the same delivery vehicle, for example a nanolipogel or polymeric nanoparticle such as PLGA. The proinflammatory cytokine can be TL-2 or IFNγ and the TGF-β inhibitor can be SB505124 or losartan. In a particular embodiment, a nanolipogel or PLGA nanoparticle is co-loaded with recombinant IL-2 and losartan.

The one or more additional immune response stimulating or enhancing agents can be an agent that decreases an immune suppressive response in the subject. Exemplary agents are discussed in more detail above and include, for example, PD-1 antagonists and CTLA4 antagonists. In preferred embodiments the PD-1 antagonist is an antagonistic anti-PD1 antibody and the CTLA4 antagonist is an antagonistic anti-CTLA4 antibody.

In preferred embodiments the one or more additional immune response stimulating or enhancing agents are not loaded into or onto the nanolipogel or other particulate delivery vehicle. The one or more additional immune response stimulating or enhancing agents can be administered to the subject in a free or soluble form, or in another conventional dosage form.

In an exemplary preferred embodiment, losartan and/or IL-2 is loaded into or onto nanolipogels or nanoparticles such as PLGA nanoparticles administered to a subject in combination with anti-PD-1, anti-CTLA4, or a combination thereof.

Without being bound by theory, it is believed that the when one or more immune response stimulating agents such as antagonistic anti-PD-1 and/or antagonistic anti-CTLA4 are co-administered in combination with nanolipogels or particles loaded or associated with a proinflammatory cytokine such as IL-2 and/or a TGF-β inhibitor such as losartan, (1) the immune response stimulating agent(s) can be administered at a lower dose; (2) the immune response stimulating agent(s) will exhibit reduced side effects or toxicity to the subject; (3) the immune response stimulating agent will exhibit enhanced potency, and/or (4) the result achieved by the immune response stimulating agent in combination with the loaded nanolipogels or particles will have a greater than additive effect on the subject when compared to administration of the immune response stimulating agent(s) without the loaded nanolipogels or particles; or administering the loaded nanolipogels or particles in the absence of the immune response stimulating agent(s).

In another exemplary strategy, a subject in need thereof is administered a nanoparticulate composition including a proinflammatory cytokine and/or a TGF-β inhibitor in combination with one or more chemotherapeutic agents. The proinflammatory cytokine and/or TGF-β inhibitor agents can be loaded into or onto the same particle, or into or onto separate particles and co-administered. In some embodiments, only nanolipogels or particles including a proinflammatory cytokine or including a TGF-β inhibitor are administered to the subject in the absence of the other. In a preferred embodiment, the proinflammatory cytokine and TGF-β inhibitor are loaded into or onto the same delivery vehicle, for example a nanolipogel or polymeric nanoparticle such as PLGA. The proinflammatory cytokine can be IL-2 or IFNγ and the TGF-β inhibitor can be SB505124 or losartan. In a particular embodiment, a nanolipogel or PLGA nanoparticle is co-loaded with recombinant IL-2 and losartan.

In preferred embodiments, the one or more chemotherapeutic agents are not loaded into or onto the nanolipogel or other particulate delivery vehicle. The one or more chemotherapeutic agents can be administered to the subject in a free or soluble form, or in another conventional dosage form. Exemplary chemotherapeutic agents are discussed above. In a particular embodiment, the chemotherapeutic agent is doxorubicin.

In an exemplary preferred embodiment, losartan and/or IL-2 is loaded into or onto nanolipogels or nanoparticles such as PLGA nanoparticles administered to a subject in combination with doxorubicin.

As discussed above with respect to immune response stimulating agents, it is likewise believed that the when one or more chemotherapeutic agents such as doxorubicin is co-administered in combination with nanolipogels or particles loaded or associated with a proinflammatory cytokine such as L-2 and/or a TGF-β inhibitor such as losartan, (1) the chemotherapeutic agent(s) can be administered at a lower dose; (2) the chemotherapeutic agent(s) will exhibit reduced side effects or toxicity to the subject; (3) the chemotherapeutic agent will exhibit enhanced potency, and/or (4) the result achieved by the chemotherapeutic agent in combination with the loaded nanolipogels or particles will have a greater than additive effect on the subject when compared to administered the chemotherapeutic agent(s) without the loaded nanolipogels or particles; or administering the loaded nanolipogels or particles in the absence of the chemotherapeutic agent(s).

The combination therapies and treatment regimens can be used to induce, increase, or enhance an immune response (e.g. an increase or induction of T cell response such as T cell proliferation or activation) in a subject in need thereof. Exemplary subjects include those with cancer or an infectious disease as described in more detail above. The immune response, (e.g., increased or induced T cell response) can be against a cancer or disease antigen. The immune response can be effective to treat the cancer or infection. In some embodiments, the immune response is against cancerous or disease infected cells and can reduce one or more symptoms of the cancer or disease (e.g., tumor burden, tumor progression, disease progression, etc.).

Preferred dosages for nanoparticulate compositions include a proinflammatory cytokine and/or a TGF-β inhibitor are discussed above. In other particular embodiments, such as the adjuvant compositions and methods described here, the nanoparticulate composition is administered in a range of about 0.1 mg/kg to 100 mg/kg, or about 0.1 mg/kg to 1 mg/kg; or about 10 mg/kg to 100 mg/kg; or 0.1-1 mg/kg to 10-100 mg/kg (e.g., daily; or 2, 3, 4, 5 or more times weekly; or 2, 3, 4, 5 or more times a month, etc., as discussed in more detail above).

EXAMPLES

Example 1

Trafficking of Nanoparticles to Spleen and Presentation to Dendritic Cells

Materials and Methods

Nanoparticles were made and characterized according to previously described protocols (Look, et al., *J. Clinical Investigation*, 123(4):1741-9 (2013), Shirali, et al., *Am. J. Transplant*, 11(12):2582-92 (2011)). PLGA particles, fluorescent probe (COumarin 6) was dissolved with PLGA in ethyl acetate, and emulsified with poly(vinyl alcohol) and avidin-palmitate using a sonicator probe. PLGA particles were subsequently hardened, washed, and then lyophilized. Biotinylated poly(ethylene glycol) was added to PLGA particles at a ratio of 1.33 µg per mg particle prior to use in experiments.

Figure 1B:
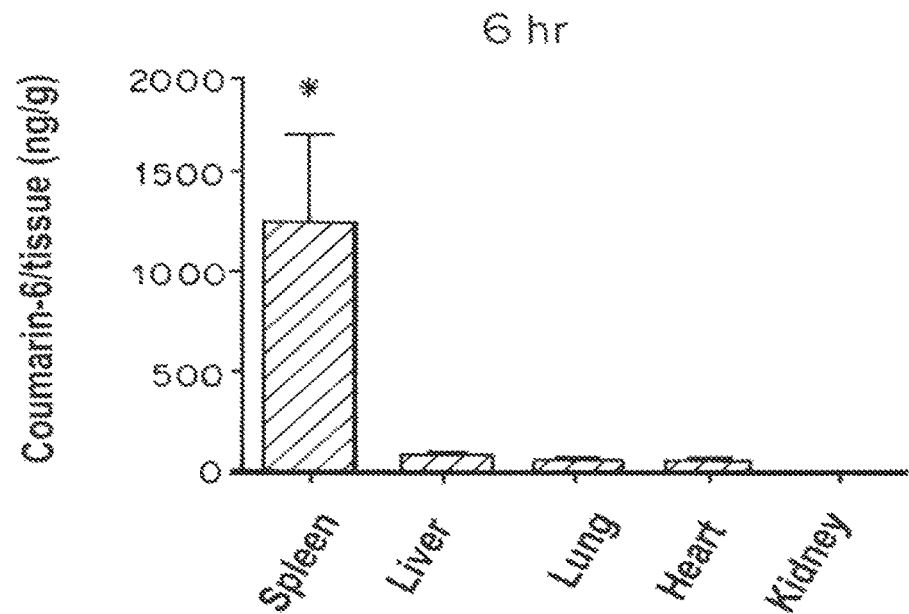
FIG. 1B is a bar graph showing the distribution of coumarin-6/tissue (ng/g) in the spleen, liver, lung, heart, and kidney of mice six (6) hours after injection with coumarin-6-loaded PLGA nanoparticles.
Figure 1C:
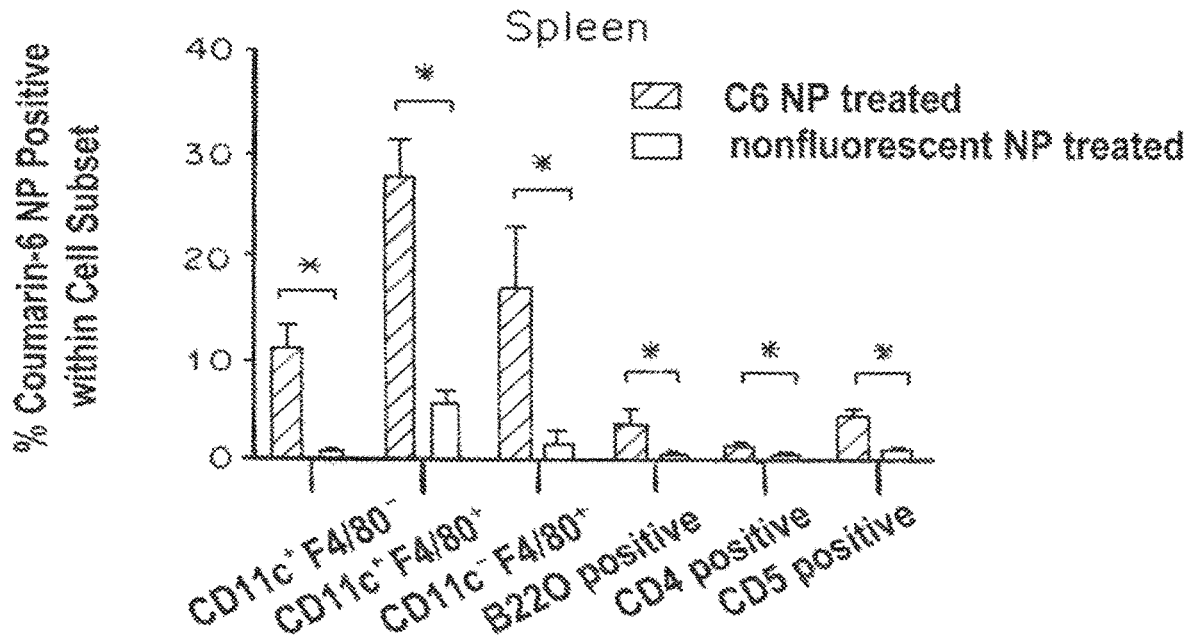
FIG. 1C is a bar graph showing the % coumarin-6 PLGA nanoparticle positive cells within cell subsets (CD11c$^|$F4/80$^-$, CD11c$^|$F4/80$^|$, CD11c$^-$F4/80$^-$, B220 positive, CD4 positive, and CD8 positive) in the spleen (C6 PLGA nanoparticle treated (closed bars), nonfluorescent PLGA nanoparticle treated (open bars).
Figure 1D:
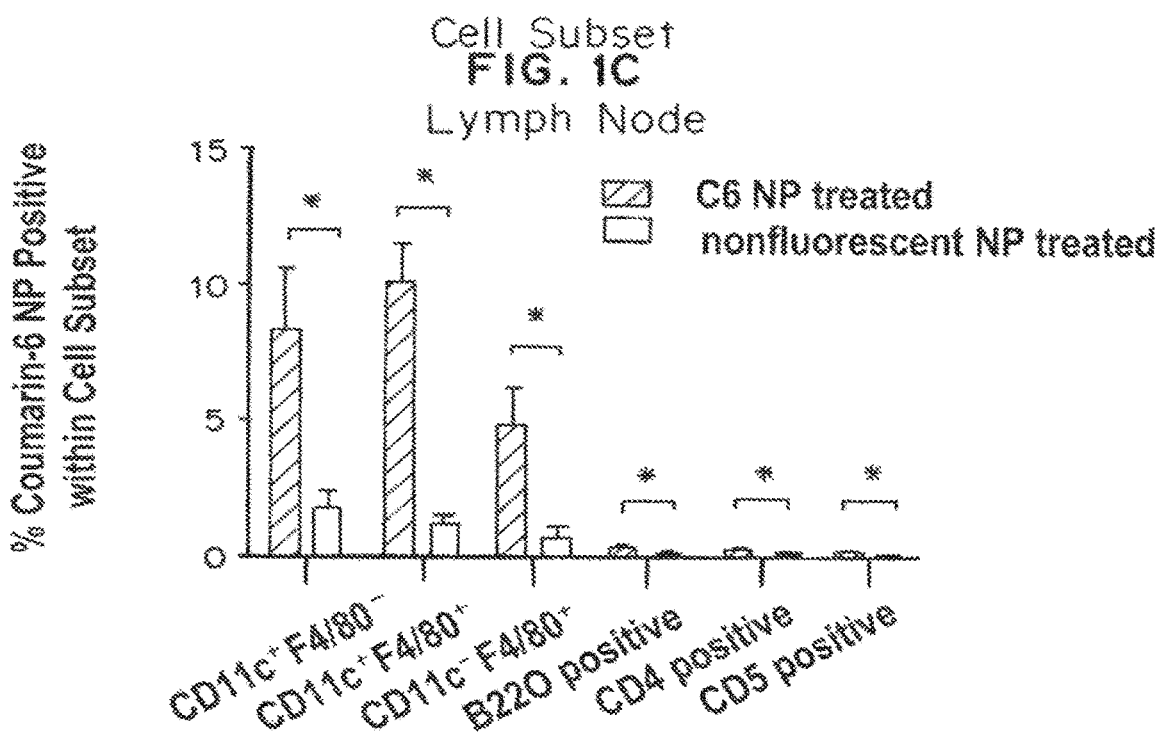
FIG. 1D is a bar graph showing the % coumarin-6 PLGA nanoparticle positive cells within cell subsets (CD11c$^+$F4/80$^-$, CD11c$^+$F4/80$^+$, CD11c$^-$F4/80$^-$, B220 positive, CD4 positive, and CD8 positive) in the lymph node (C6 PLGA nanoparticle treated (closed bars), nonfluorescent PLGA nanoparticle treated (open bars). * indicates p<0.05 by ANAOVA (organs) and by two tailed t-test.

Biodistribution studies: Particles (2 mg per animals) were prepared and then injected intraperitoneally into mice. Organs were harvested, weighed, and imaged with the IVIS imaging system to obtain quantitative fluorescence measurements. For histological analysis, spleens were snap-frozen in OCT embedding medium and then sectioned on a cryotome onto charged slides. Sections were fixed in ice cold acetone for 10 minutes, and subsequently stained with antibodies. Tissue sections were imaged on a Nikon TE-2000 microscope Results Trafficking by nanoparticles of antigens to APCs is a first important step in mobilizing a cell-based immune response against those antigens. An experiment was designed to track the accumulation of nanoparticles in vivo. Nanoparticles made of PLGA were loaded with a fluorescent agent, coumarin-6, and injected into mice. The results are presented in FIGS. 1A-1D. FIG. 1A shows that 3 hours following intravenous injection of mice with nanoparticles loaded with the fluorescent agent coumarin-6, these nanoparticles were broadly disseminated amongst a number of tissues; however, by 6 hours (FIG. 1B), the fluorescent nanoparticles were heavily concentrated in the spleen. Large populations of immune cells were concentrated in certain tissues, notably spleen. FIGS. 1C-1D show that coumarin-6 nanoparticles were prominently associated with the antigen-presenting cell populations, notably dendritic cells and macrophages, in the spleen (1C) and also lymph node (1D), another important site involved in immune stimulation.

Example 2

Nanoparticles Promote Antitumor Effects of IL-2

Materials and Methods

Nanogels were made with liposomes extruded from a lipid mixture of 1:2:0.1 molar ratio of cholesterol: phosphatidylcholine: 1,2-distearoyl-sn-glycero-3-phosphoethanolamine-N-[amino(polyethylene glycol)-2000]. Liposomes were lyophilized, and then rehydrated with a mixture of acrylated lactic acid-poly(ethylene glycol)-lactic acid, fluroscent probe (Rhodamine B) complexed in non-methylated β-cyclodextrins, and Irgacure 2959. The particles were cured under UV light, rinsed, and centrifuged and remotely loaded with 100 ug/ml of human IL-2 (Proleukin). Nanogels were functionalized with avidin using sulfo-N-hydroxysuccinimide/1-ethyl-3-[3-dimethylaminopropyl]carbodiimide hydrochloride (sNHS/EDC). Biotinylated T cell receptor was added at a concentration of 10 ug of TCR per mg of nanoparticles. (Look, et al., *J. Clinical Investigation*, 123 (4):1741-9 (2013), Joshi, et al., *J. Control Release*, 161(1): 25-37 (2012), Danhier, et al., *J. Control Release*, 161(2): 505-22 (2012), Elamanchili, et al., *Vaccine*, 22(19):2406-12 (2004), Shirali, et al., *Am. J. Transplant*, 11(12):2582-92 (2011)).

Results

Figure 2:
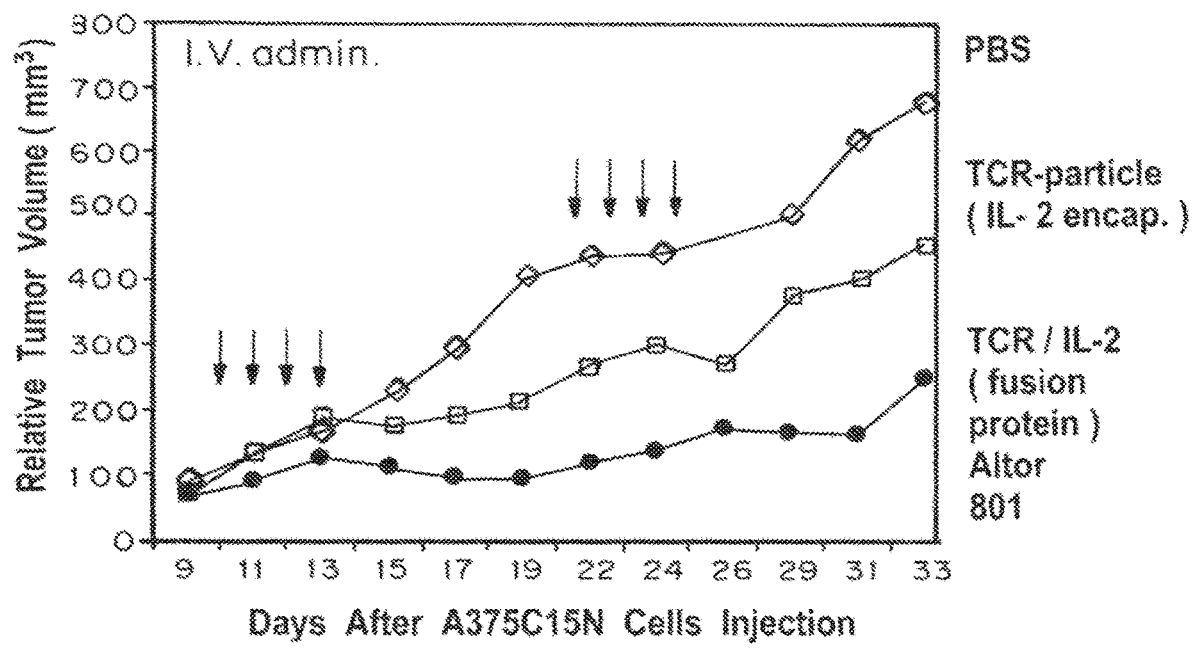
FIG. 2 is a line graph showing the relative tumor volume (mm$^3$) in nude mice over time (days) following subcutaneous A375C15N (p53+HLA-A2/Human melanoma) xenograft tumor establishment and subsequent treatment with PBS, TCR-particle (IL-2 encapsulated) nanolipogels, or TCR/IL-2 (soluble p53-specific scTCR/IL-2 fusion protein (Altor 801, Altor Biosciences, Miramar, Fla.)) nanoparticles.

Immunodeficient (nude) mice were xenografted subcutaneously with $10^5$ cells of human A37C515N melanoma cells expressing the p53 antigen. At the times indicated in FIG. 2 (arrows), the mice were either injected intravenously with nanoparticles coupled to the T cell receptor (TCR) that recognizes this p53 antigen within the context of human MHC and loaded with the cytokine IL-2, or with a soluble p53-specific scTCR/IL-2 fusion protein (Altor Biosciences, Miramar, Fla.). FIG. 2 shows that mean tumor volumes in mice treated with the chimeric protein were reduced by approximately 40% compared with tumors in PBS-treated control mice. However, at the end of the study period mean tumor volumes in nanoparticle-treated mice were reduced by approximately 70%, even though the amount of IL-2 loaded in nanoparticles was approximately 1000-fold lower compared to the relative TL-2 concentration in the TCR/IL-2 chimeric protein. An increased avidity for IL-2 and/or the TCR on the nanoparticle relative to the soluble fusion protein could explain the superior antitumor potency of the nanoparticle preparation.

Example 3

IL-2 or IFN Gamma in Combination with Anti-CD40 on Nanoparticles Show Anti-cancer Activity Materials and Methods PLGA nanoparticles was prepared as described in Example 1. IFN gamma (100 ug/ml) was loaded with 100 mg of PLGA. Anti-CD40 biotin (10 ug/ml) was added per 1 mg/ml of polymer np surfaced modified with avidin as described in Example 1.

Results

IL-2, which is produced and secreted by activated T cells, can be combined on nanoparticles with other immuno-promoting agents to elicit an anti-tumor effect. One such agent is an agonistic antibody to CD40. (Honeychurch, J., Glennie, M J, Johnson, P W, Illidge, T M.: Anti-CD40 monoclonal antibody therapy in combination with irradiation results in a CD8 T-cell-dependent immunity to B-cell lymphoma. *Blood* 2003; 102:1449-1457). CD40 is a costimulatory protein found on APCs and is required for their activation. Such activation occurs when CD40 binds to CD40L (CD154), a protein that is primarily expressed on activated T cells and is a member of the TNF superfamily of molecules. Agonistic anti-CD40 subserves the function of CD40L in activating APCs, and thus a nanoparticle carrying a combination of agonistic anti-CD40 and IL-2 can provide some functional aspect of a T helper cell.

Homotrimerization of some members of the TNF superfamily occurs during activation implicating a role for valency and high avidity interactions during signaling. Indeed, higher order oligomers as would be expected on the plasma membrane may be required to achieve an effective response (Grell, et al., *Cell*, 83: 793-802 (1995), Tanaka, et al., *Nat. Med.*, 4: 31-36 (1998), Schneider, et al., *J. Exp. Med.*, 187: 1205-121 (1998)).

Thus, experiments were designed to determine if nanoparticles displaying anti-CD40 interact with higher avidity to targets, and are capable of recapitulating physiological requirements for potent signaling that cannot be achieved with soluble monomeric or CD40 antibody complexes.

Figure 3:
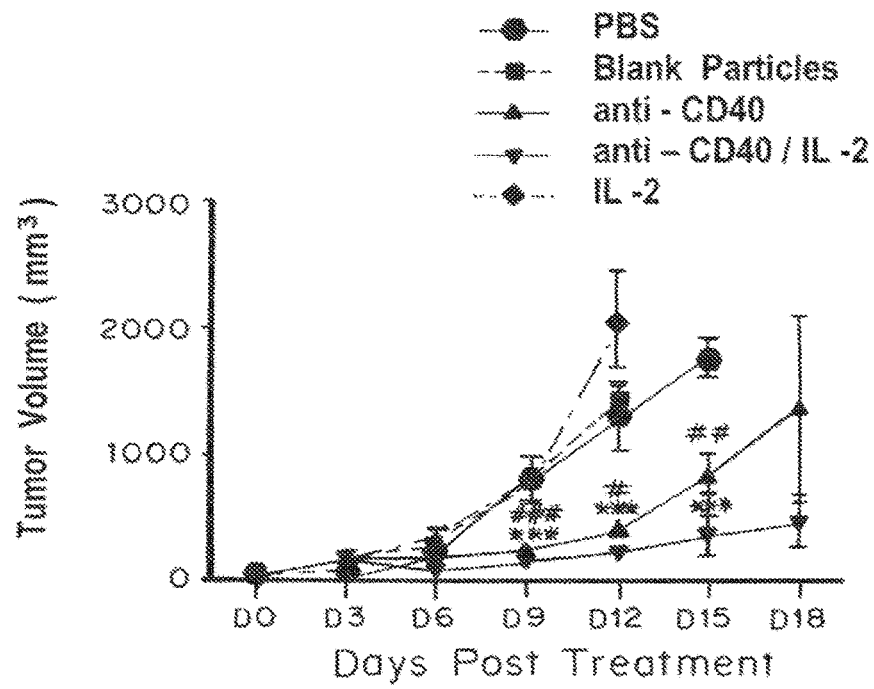
FIG. 3 is a line graph showing the tumor volume (mm$^3$) in mice over time (days) following treatment with 5 μg of PLGA nanoparticles surface modified with anti-CD40 (-▲-); or surface modified with anti-CD40 and loaded with IL-2 (-▼-); or, as controls, blank particles (clear surface and empty) (-■-); or buffered saline (1×PBS) (-●-) beginning approximately 7 days after inoculation with B16F10 melanoma cells.

Animals were inoculated with B16F10 melanoma cells in the hind limb. Tumor growth was monitored and approximately 7 days later, when the tumor reached 0.5 $mm^2$ in area, animals were treated peritrumorally with 5 ug of PLGA nanoparticles (a) surface modified with anti-CD40; (b) surface modified with anti-CD40 and loaded with IL-2; or, as controls, (c) blank nanoparticles (clear surface and empty) or (d) buffered saline (1×PBS). Unloaded PLGA nanoparticles had no effect on tumor growth compared with PBS treatment (FIG. 3). IL-2 alone on nanoparticles has little or no anti-tumor properties. Agonistic anti-CD40 on nanoparticles does show a significant anti-cancer effect during the term of the experiment, indicating that surface presentation of this antibody on its own may have therapeutic utility (FIG. 3). The most potent response was seen with nanoparticles containing agonistic anti-CD40 and IL-2 (FIG. 3).

Example 4

IL-15 on Nanoparticles Activates NK Cells

Materials and Methods

Poly(lactide-co-glycolide) (PLGA) 50/50 with an average molecular weight of 80 kDa was obtained from Durect Corporation (Cupertino, Calif.) and used for nanoparticle fabrication. Nanoparticles were formed using an oil-in-water emulsion technique, or a water-in-oil-in-water double emulsion technique for hydrophilic encapsulants. Emulsions were sonicated 3 times for 10 seconds each on a 600 W Ultrasonic Processor (Sonics & Materials Inc, Newtown, Conn.) probe sonicator, and allowed to harden for 1.5-3 hours in a 0.2% solution of poly(vinyl alcohol). Nanoparticles were surface-modified with avidin-palmitate conjugates as previously described. Particles were washed with $dH_2O$, lyophilized, and stored at −20° C.

Human IL-15: IL-15Rα heterodimer was a generous gift from the National Cancer Institute at Frederick (Frederick, Md.). TL-15 heterodimer was reacted at a 1:10 molar ratio with NHS-LC-LC-biotin (Thermo Scientific, Rockford, Ill.), then dialyzed for 48 h in PBS to remove excess unreacted biotin. Biotinylated IL-15 heterodimers were added to nanoparticles at indicated concentrations, and incubated on a rotary plate shaker for 15 min at room temperature.

Results

Figure 4:
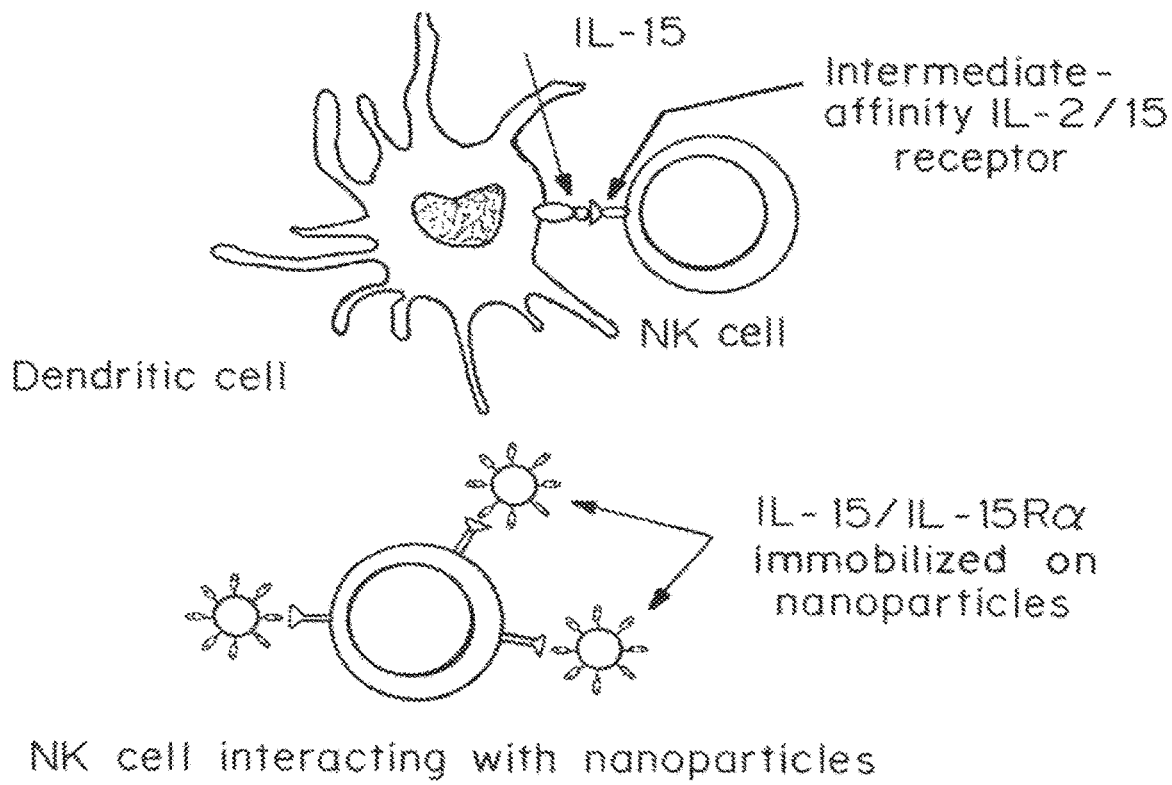
FIG. 4 is an illustration showing a PLGA nanoparticles displaying an avidin-biotin linked IL-15RαFC fusion protein, including how it is manufactured and how it is believed to interact with target cells such as NK cells based on the naturally occurring interaction between IL-15 (expressed on dendritic cells) and Intermediate-affinity IL-2/15 receptor expressed on NK cells.
Figure 4:
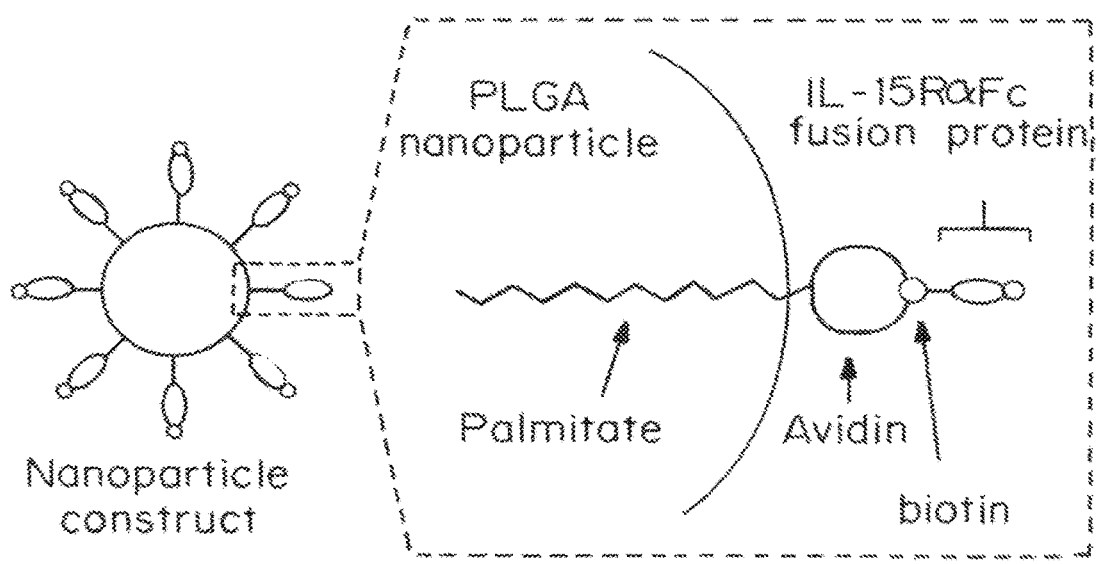
Figure 4:
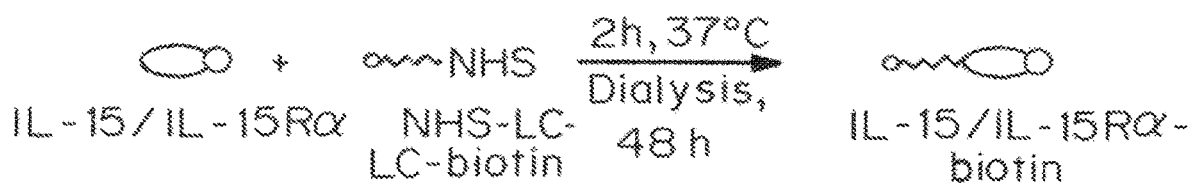

Interleukin-15 (IL-15) is a cytokine that shares certain receptor subunits with IL-2 and thus has some overlapping mechanisms of action. IL-15 is expressed by dendritic cells and provides a critical signal for the proliferation and priming of natural killer (NK) cells. IL-15 binds tightly to a receptor subunit not shared by IL-2, called IL-15Rα. IL-15Rα is capable of binding IL-15 independently of other subunits. It is suggested that this property allows IL-15 to be produced by one cell, endocytosed by second cell, and then presented to a third cell. Since soluble complexes of IL-15/IL-15Rα can be prepared, it is possible to evaluate the potential anti-cancer activity of the IL-15/IL-15Rα complex. Such complexes of IL-15/IL-15Rα can also be loaded onto nanoparticles and act in some respects as an artificial dendritic cell (FIG. 4).

Figure 5A:
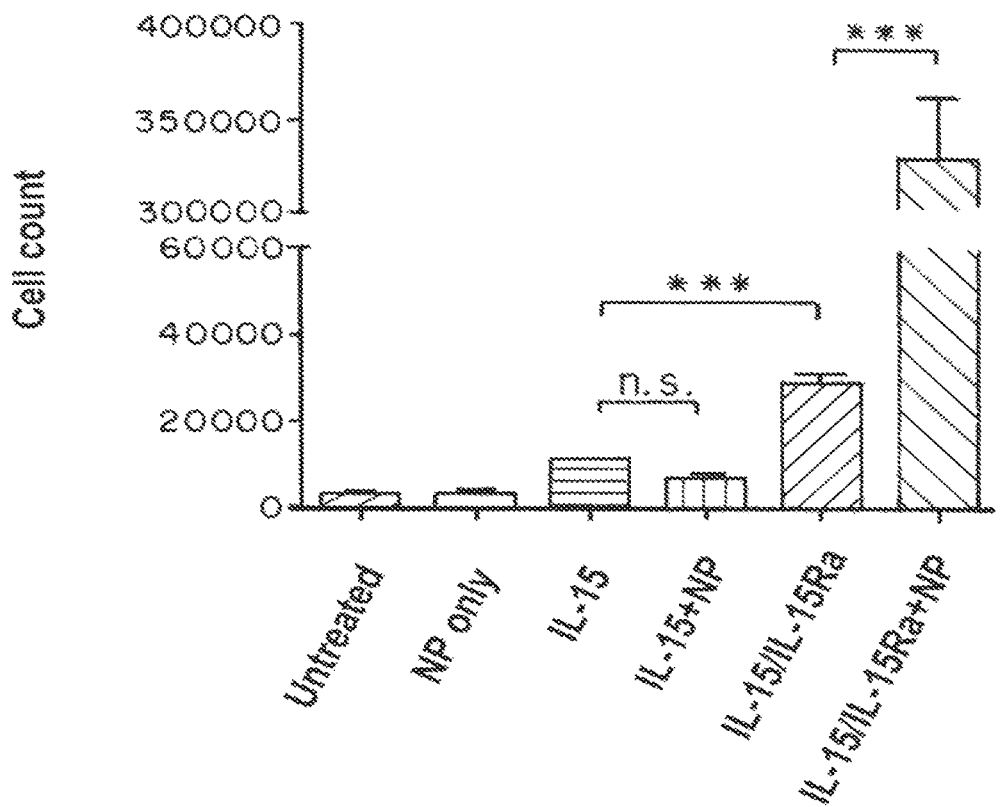
FIG. 5A is a bar graph showing NK proliferation (cell count) in untreated controls, and following treatment with PLGA nanoparticles only, IL-15 only, IL-15 loaded nanoparticles, IL-15/IL-15Rα complex only, IL-15/IL-15Rα complex decorated nanoparticles.
Figure 5B:
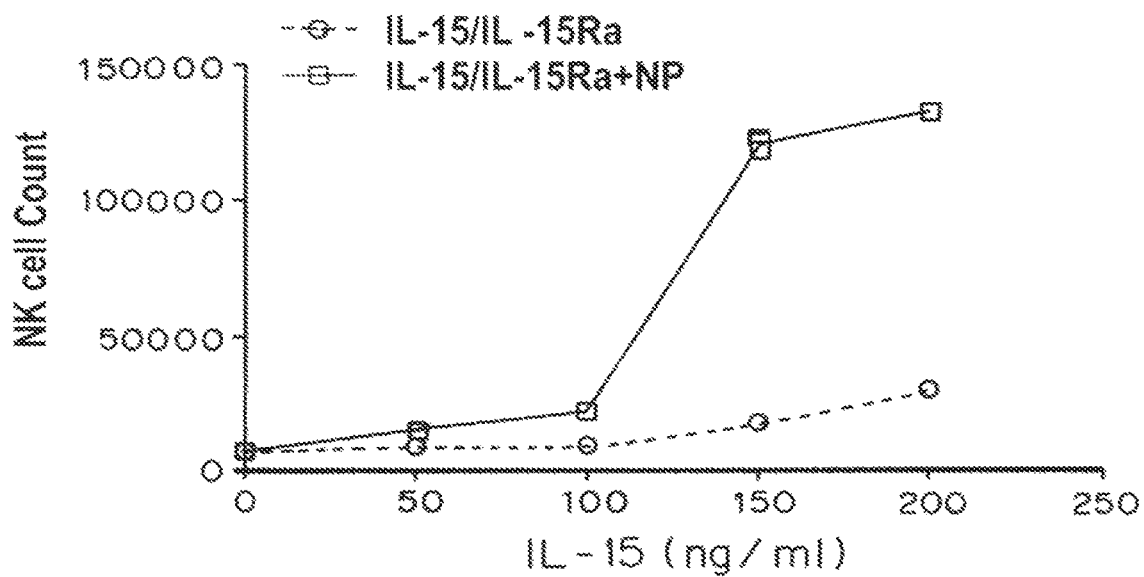
FIG. 5B is a line graph showing NK proliferation (cell count) following treatment with IL-15/IL-15Rα complex only and IL-15/IL-15Rα complex decorated nanoparticles as a function of concentration.
Figure 5C:
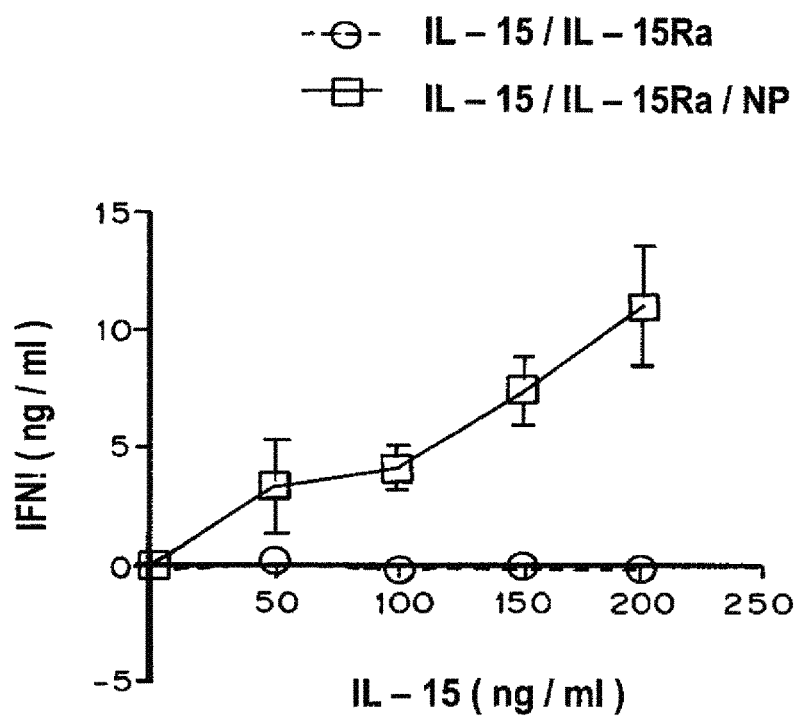
FIG. 5C is a line graph showing IFN-γ (ng/ml) following treatment with IL-15/IL-15Rα complex only and IL-15/IL-15Rα complex decorated nanoparticles as a function of concentration.

Experiments were designed to test the ability of IL-15/IL-15Rα complex decorated nanoparticles to modulate an immune response. The results indicate that multivalent presentation of IL-15/IL-15Rα complexes on the surface of nanoparticles facilitates the adhesion of nanoparticles to NK cells. IL-15/IL-15Rα complexes on nanoparticles expanded NK cells more effectively than IL-15 alone or soluble IL-15/IL-15Rα complexes (FIG. 5A). When stimulated with IL-15/IL-15Rα complexes on nanoparticles, these NK cells also demonstrated elevated levels of Interferon-γ even at nanoparticle concentrations that do not promote significant levels of cell division (FIGS. 5C and 5B, respectively) The results also show that IL-15/IL-15Rα complexes on nanoparticles promoted expansion of CD8$^+$ T cells.

Example 5

IL-15 on Nanoparticles Shows Anti-tumor Activity

Materials and Methods

IL-15/IL15R particles were used as described in Example 4. B16-OVA cells (ATCC) were cultured in DMEM (Gibco) and suspended at 2×10$^6$ cells/mL in 1×PBS (kept on ice) directly prior to injection. For subcutaneous tumor studies, female 6-8 week-old C57BL/6 mice were sedated with AErrane (isoflorane; Baxter) and the right hind flank was shaved prior to a subcutaneous injection of 50 μL of the cellular suspension. Tumors were monitored and treatment began when the average tumor area reached ~5.5 mm$^2$ (8-10 days after B16 injection; mice were rearranged to normalize tumor sizes across groups). Mice were sedated with isofluorane for nanolipogel administration, which was performed intratumorally. Each dose consisted of 2 mg IL-15/IL-15R NP. Observers were blinded for tumor area and survival studies. Mice were euthanized with carbon dioxide when any one tumor dimension >15 mm, when exhibiting any sign of sickness, or at one week post-treatment for FACS analyses studies. Five mice per group were euthanized at different timepoints and tumors were extracted and weighed.

Results

Figure 6:
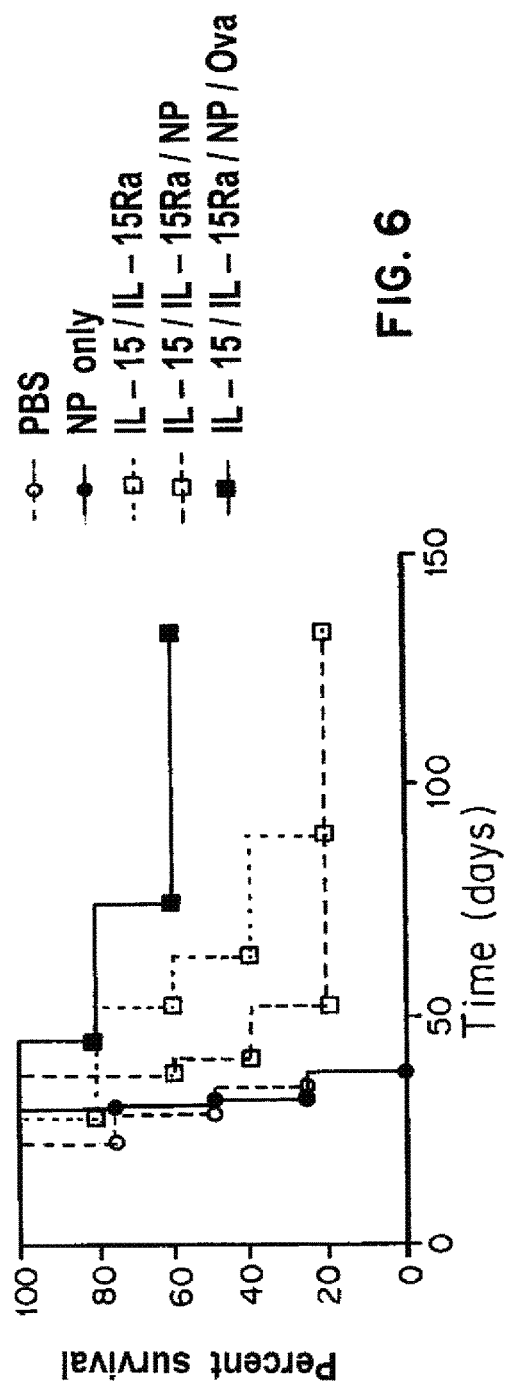
FIG. 6 is a Kaplan-Meier survival curve showing the percent survival over time of B16. Ova mice (mice injected with a derivative melanoma line, whose cells carry an ovalbumin surface antigen (OVA)) treated with PBS (-○-), nanoparticles only (-●-), IL-15/IL-15Rα complex only (-□-), IL-15/IL-15Rα complex decorated PLGA nanoparticles (-□-), and IL-15/IL-15Rα complex decorated nanoparticles encapsulating Ova (-■-).

In view of the ability of IL-15/IL-15Rα complexes on nanoparticles to promote a strong NK cell response, experiments were designed to determine the effectiveness of these complexes in a cancer model. In this Example, a metastatic B16 disease model was selected because IL-15/IL-15Rα complexes are known to play a role in an immune response to these tumors. The derivative melanoma line, B16.OVA, whose cells carry an ovalbumin surface antigen (OVA) was used. This provides the additional opportunity to evaluate the effect of tumor targeting via nanoparticles. nanoparticles were decorated with IL-15/IL-15Rα complexes and additionally loaded with endotoxin-free ovalbumin protein. 10$^5$ B16.OVA melanoma cells were injected into C57BL/6 mice and on days 1, 2 and 7 thereafter groups of 5 mice were injected with phosphate-buffered saline (PBS), unloaded PLGA nanoparticles, 1 μg IL-15/IL-15Rα of the entire complexes or the same amount of IL-15/IL-15Rα complex loaded on nanoparticles with or without encapsulated ovalbumin. FIG. 6 illustrates the results. All mice treated with PBS or unloaded nanoparticles died in less than 50 days. Mice treated with IL-15/IL-15Rα complex, either in solution or loaded onto nanoparticles, survived for longer periods of time. The most efficacious treatment was nanoparticles loaded with IL-15/IL-15Rα complex plus ovalbumin, demonstrating that targeting nanoparticles to the tumors could improve the anti-tumor effects of the IL-15/IL-15Rα complex (FIG. 6).

Example 6

Targeting TGF-β Inhibitor SB505124 with RGD Peptide Show Anti-Tumor Activity

Materials and Methods

Synthesis and Characterization of RGD/SB Nanoparticles

The conjugation of acid-terminated PLGA and amine-terminated PEG was as follows. Acid-terminated PLGA (500 mg) and a 10-fold excess of NHS and DCC were dissolved in 10 mL anhydrous DCM. After being stirred at room temperature for four hours, the reaction solution was filtered through a PTFE filter to remove the precipitate. The NHS-activated PLGA was obtained through precipitation in cold ethyl ether. After drying under vacuum, NHS-activated PLGA was dissolved in anhydrous DCM with an equivalent molar ratio of NH$_2$—PEG-COOH, and the solution was stirred at room temperature. The conjugate was precipitated in cold ethyl ether and dried under vacuum with a yield above 90%. RGD peptide was conjugated with the carboxylic group of PLGA-PEG-COOH using NHS and EDC. Using this block copolymer, a TGF-β inhibitor drug was encapsulated into the nanoparticles using a dialysis method. Specifically, the drug and polymer were dissolved in DMSO, and the solution was transferred into a dialysis membrane (MWCO 100,000). The dialysis was carried out for 24 hours against DI water. After that, the aqueous particle solution was centrifuged and sonicated to concentrate the particles.

The size of the nanoparticles or ID was determined by dynamic light scattering (DLS) using a Zetasizer (Malvern). The sample concentration was maintained at 0.5 mg/mL. The amount of SB encapsulation was derived from its absorbance measurement by dissolving 10 mL of SB nanoparticles into 990 mL DMSO, which released SB into the DMSO solution. Absorbance was then measured at 300 nm. Using a pre-measured calibration curve of SB absorbance according to its titrated concentration, the encapsulated SB concentration was calculated. The SB release profile was determined according to a different protocol. One milliliter of PBS-SB nanoparticles was prepared in an Eppendorf tube with moderate shaking. At each time point, the tube was centrifuged to pellet the nanoparticles, and the supernatant was gathered. The supernatant was diluted 100 times into DMSO, and its absorbance was measured at 300 nm.

Results

Studies have shown that integrin is overexpressed on the surface of tumor cells and can serve as a marker that distinguishes between tumor cells and normal cells. Integrin also activates TGF-β through an extracellular pathway. After latent TGF-β is released from a tumor cell, it binds with integrin on the surface of the tumor cell, leading to the activation of the latent TGF-β. As a result, increased TGF-β concentrations in the tumor microenvironment support immune suppression by recruiting regulatory T cells (Massayo, et al., *Eur J Clin Med Oncol.*, (4):27-32 (2013). Elevated TGF-β molecules can be inhibited by a TGF-β inhibitor such as SB505124 (2-(5-benzo[1,3]dioxol-5-yl-2-tert-butyl-3H-imidazol-4-yl)-6-methylpyridine hydrochloride). SB-505124 is a selective inhibitor of transforming growth factor-beta type I receptors ALK4, ALK5, and ALK7 (DaCosta, et al., *Mol Pharmacol.* 65:744-52 (2004)), also known as SB505124 (also abbreviated as SB).

In this Example, SB505124 was loaded directly into PLGA-PEG nanoparticles as described above.

RGD peptide can serve a dual function: it is not only a typical integrin-targeting ligand (Ruoslahti, et al., *Annu. Rev. Cell Dev. Biol.*, 12:697-715 (1996)) but serves as an immune danger signal, activating APCs (Altincicek, et al., *Biol Chem.*, (390)1303-11 (2009)).

Figure 7:
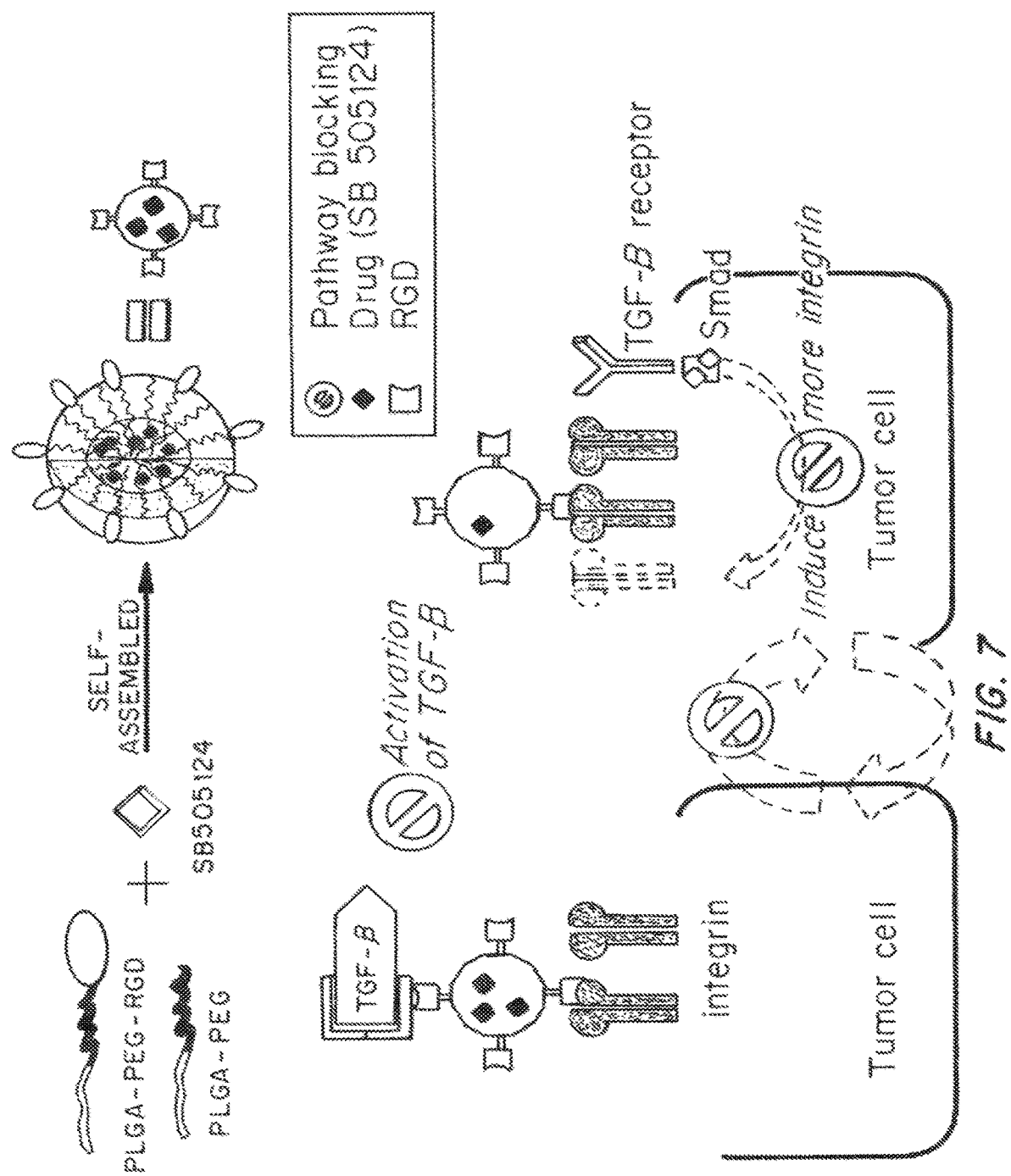
FIG. 7 is an illustration showing the formation of PLGA-PEG nanoparticles decorated with RGD peptide and encapsulating SB505124, and its proposed mechanism of action on tumor cells.

In this Example, PLGA nanoparticles were loaded with SB505124 and RGD peptide. These nanoparticles promoted a strong antitumor effect, involving prominently the modulation of TGF-β and its activation and function in multiple ways (FIG. 7); both agents also modulated elements of the immune system so that the local environment shifted from suppressive to stimulatory. The RGD peptide by virtue of its role as an immune danger signal can activate APCs and via its interaction with integrins it can block the binding between latent TGF-β and integrin. SB505124 can inhibit TGF-β activation. Thus, latent TGF-β is minimally activated and Treg-mediated tumor immune evasion is prevented.

Figure 8:
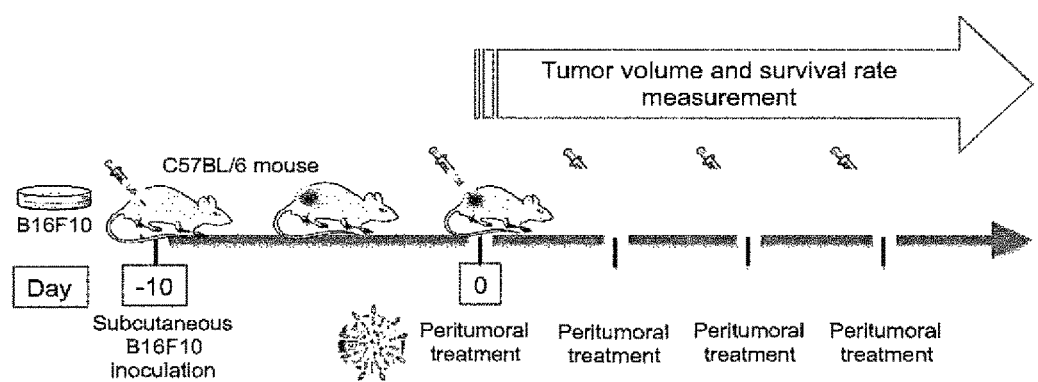
FIG. 8 is a diagram illustrating a mouse tumor model used in the Example 6 below. B16F10 melanoma tumor cells (500,000 cells) were injected into the tail vein of C57BL/6 mice on day 0 and later injected IV with SB505124 and RGD in solution or with one or both agents loaded onto PLGA-PEG nanoparticles. Mice were sacrificed, lungs were collected, and, tumor nodules were counted.

FIGS. 8 and 9A-9C summarize studies to determine the effects of SB505124 and/or RGD on B16f10 melanoma cells. Treatments were initiated 10 days after inoculation of the mice with tumor cells (FIG. 8). RGD (100 nM) and/or SB505124 (100 nM) were administered either in solution or loaded onto nanoparticles effect for delayed clearance (7 mice per group). In one set of experiments animals were given four weekly pertiumoral injections and both volumes and survival rates were tracked over a period of 5 weeks.

Figures 9A, 9B:
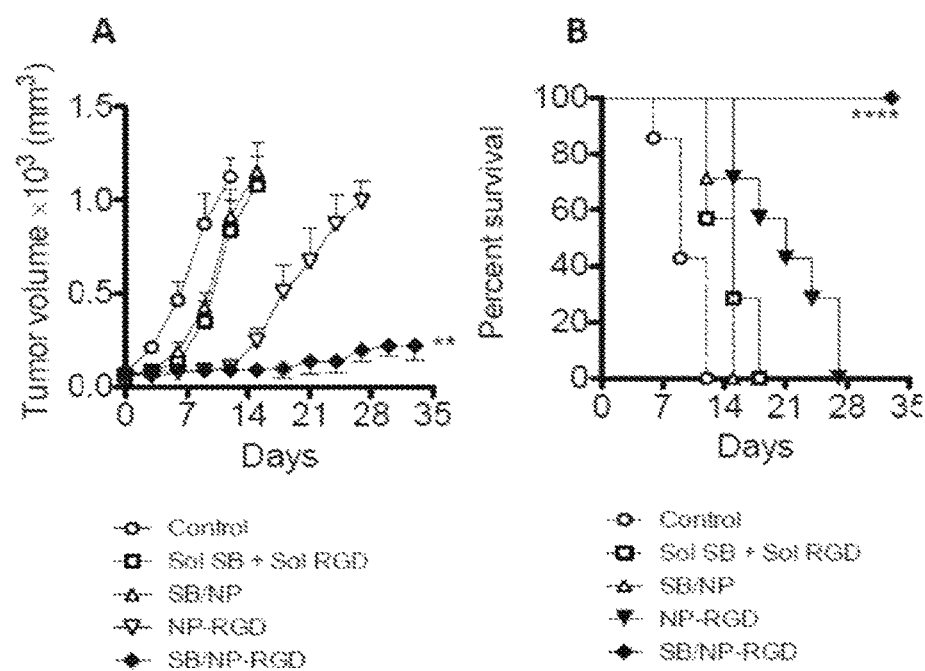
FIG. 9A is a bar graph showing the tumor volume×10$^3$ (mm$^3$) over time for mice treated according to the assay of FIG. 8. Control (-○-), soluble SB505124 and RGD (Sol SB+Sol RGD (-□-), SB505124 loaded PLGA-PEG nanoparticles (SB/NP -Δ-), RGD decorated nanoparticles (NP-RGD (-∇-)), or SB505124 loaded and RGD decorated nanoparticles (SB/NP-RGD (-♦-)).
FIG. 9B is a Kaplan-Meier survival curve showing the percent survival over time of mice treated according to the assay of FIG. 8. Control (-○-), soluble SB505124 and RGD (Sol SB+Sol RGD (-□-), SB505124 loaded nanoparticles (SB/NP -Δ-), RGD decorated nanoparticles (NP-RGD (-∇-)), or SB505124 loaded and RGD decorated nanoparticles (-♦-).
Figure 9C:
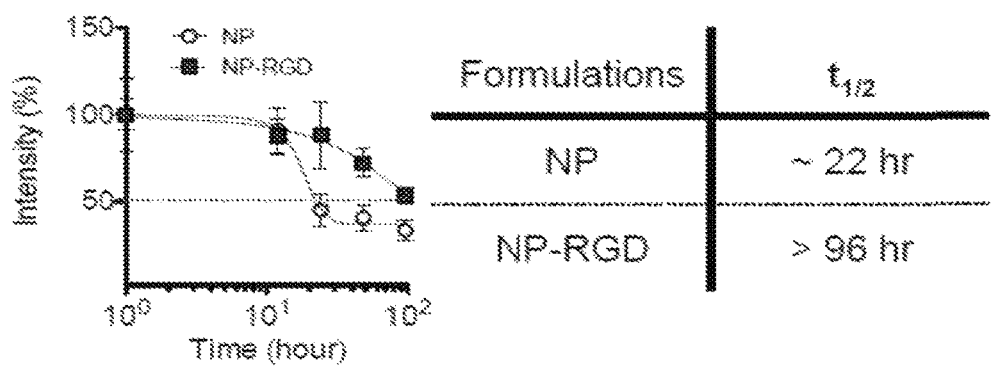
FIG. 9C is a line graph showing the half-life of nanoparticles (-○-) and RGD decorated nanoparticles (SB/NP-RGD (-■-)).

As shown in FIGS. 9A and 9B, soluble SB505124 and RGD had a modest anti-tumor effect, if any. The same was true when SB505124 was loaded onto nanoparticles and administered to the mice. Although nanoparticles carrying RGD appeared to have an antitumor effect, the combination of SB505124 and RGD on nanoparticles had a far superior, statistically significant antitumor effect. At least part of the increased efficacy via nanoparticle administration may have been due to decreased clearance, as illustrated when Coumarin-encapsulated nanoparticles with or without RGD were injected peritumorally into groups of 4 mice and scanned over a 96 hr period. Fluorescent intensity indicated a half-life of nanoparticle-bound RGD at least 4 times greater than that of free RGD (FIG. 9C).

Example 7

Targeting TGF-β Inhibitor SB505124 with RGD Peptide Show Anti-Tumor Activity

Materials and Methods

Materials are as described above. For the in vivo study, mice were housed in autoclaved micro-isolator cages that were placed in a positive pressure containment rack and maintained according to an approved protocol from the Yale University Institutional Animal Care and Use Committee.

The mice were randomly assigned to experimental and control groups of 5-7 animals each. B16F10 melanoma cells were cultured as described above. The melanoma xenografts were initiated by subcutaneously implanting $5 \times 10^6$ B16F10-Ova or B16F10 cells in the right rear flank of the mice. After 10 days, each mouse was treated with a different drug formulation. All formulations were injected directly into the tumor. For the multiple dose study, all formulations were injected once per week. The tumor inhibition activity was determined by the tumor volume, which was calculated using the following equation: $V=(w)^2 \times (l)/2$, where (w) and (l) were the width and length of the tumor as measured by a caliper.

For tumor biodistribution studies, mice were treated with coumarin 6-encapsulated RGD nanoparticles by intratumoral injection. Coumarin 6-encapsulated nanoparticles without RGD were used as a control. Using an in vivo molecular imaging instrument (Carestream molecular imaging), the mice were scanned to measure the fluorescence intensity of coumarin 6 in the tumor at different time points after injection. The coumarin 6 intensity of each mouse was analyzed in the region of interest (ROI) encompassing each tumor area at each time point.

Results

Figures 10A, 10B:
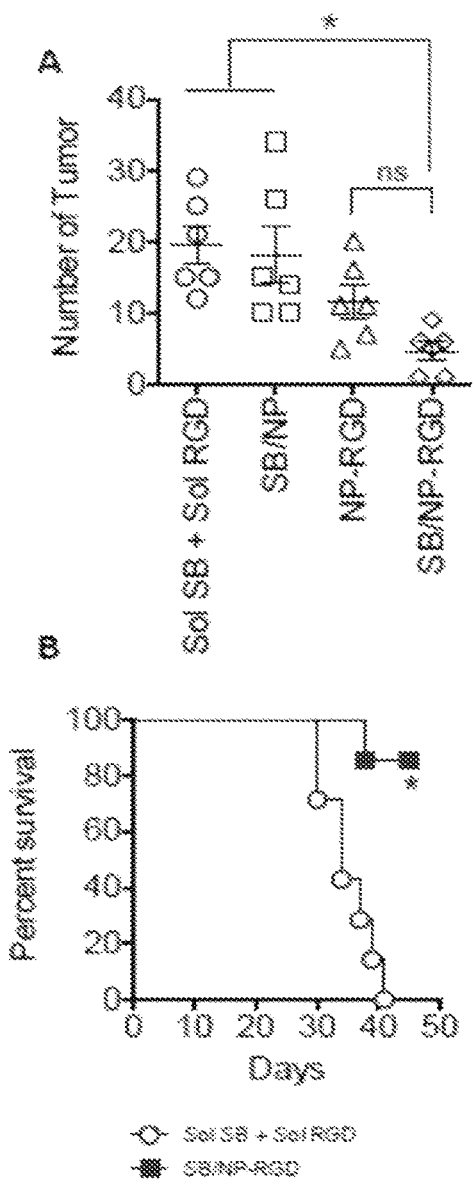
FIG. 10A is a dot plot showing the number of tumors in a mouse tumor model after treatment with soluble SB505124 and RGD (Sol SB+Sol RGD), SB505124 loaded PLGA-PEG nanoparticles (SB/NP), RGD decorated nanoparticles (NP-RGD), or SB505124 loaded and RGD decorated nanoparticles (SB/NP-RGD).
FIG. 10B is a Kaplan-Meier survival curve showing the percent survival over time of mice treated with soluble SB505124 and RGD (Sol SB+Sol RGD (-○-)) or SB505124 loaded and RGD decorated nanoparticles (SB/NP-RGD (-■-)).

B16F10 melanoma tumor cells (500,000 cells) were injected into the tail vein of C57BL/6 mice on day 0. On day 5, mice were injected IV with SB505124 and RGD in solution or with one or both agents loaded onto nanoparticles. Ten days later, mice were sacrificed, lungs were collected and, tumor nodules were counted. FIG. 10A illustrates that administration of nanoparticle-bound SB505124 and RGD led to a significant decrease in the number of nodules vs administration of the two agents in solution; nanoparticles containing either agent alone elicited an intermediate response.

To determine the effect of these agents on metastatic tumors over longer periods of time 500,000 B16f10 melanoma cells were injected i.v., via the tail vein on day 0. Once again, the tumor-bearing mice were injected with SB505124 and RGD, either in solution or loaded onto nanoparticles, in this case on days 5, 12, 19 and 26. FIG. 10B illustrates that treatment with nanoparticle-bound SB505124 and RGD led to a dramatically prolonged survival time when compared with mice receiving the agents in solution.

There are a number of mechanisms by which nanoparticle-bound SB505124 and RGD could elicit a potent inhibitory effect in a metastatic tumor model. One compelling mechanism involves the process of metastatis. Accumulating evidence indicates that a sub-fraction of cancer cells, cancer stem cells (CSCs), are exclusively capable of tumor formation and renewal (Clarke, et al., *Cancer Res.*, 66:9339-9344 (2006); Dalerba, et al., *Annu. Rev. Med.*, 58:267-284 (2007)). CSCs in solid tumors are generally thought to be a functionally homogeneous population of cancer cells that drive tumor maintenance. In an epithelial tumor, these CSCs maintain the epithelial characteristics of the tumor but lack the capacity to migrate and therefore cannot establish metastasis. Only a small subset has the potential to migrate and initiate metastasis formation. This property is associated with expression of TGF-β, which can serve an important role in cancer metastasis by inducing a epithelial-mesenchymal transition (EMT). Thus TGF-β, secreted by most cancer cells, can function in a paracrine manner to induce the formation of cancer cells with metastatic potential.

Experiments were designed to determine if inhibition of TGF-β in the tumor microenvironment could prevent the generation of mesenchymal cells and thus decreases metastatic tumor load.

Figure 10C:
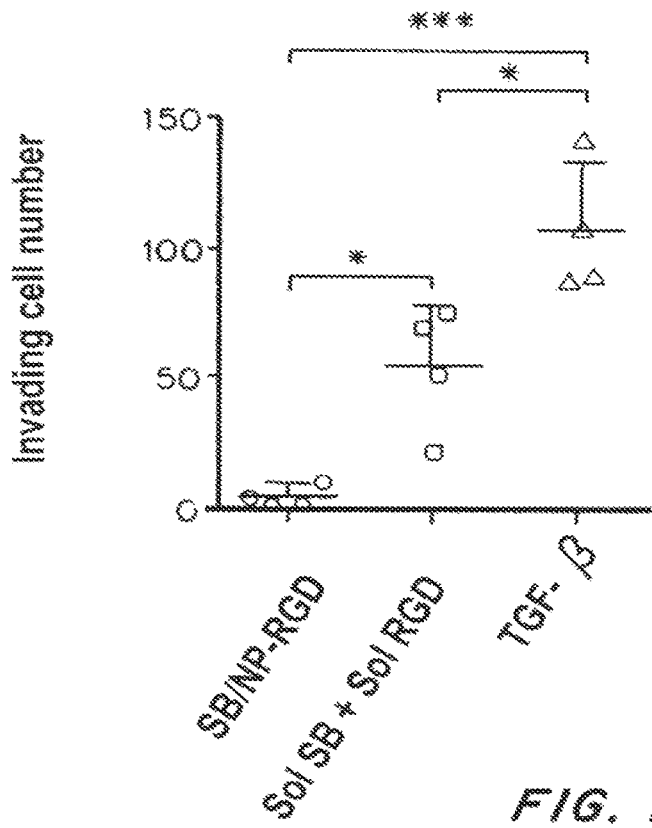
FIG. 10C is a dot plot showing the number of invading cells after treatment with SB505124 loaded and RGD decorated nanoparticles (SB/NP-RGD), soluble SB505124 and RGD (Sol SB+Sol RGD), SB505124 loaded nanoparticles (SB/NP), or TGF-β. Effector cells (NK, CD8+ T cells, CD4+ T cells) and regulatory T cells (CD4+FOXP3+CD25+) cells were assayed here.
Figure 10D:
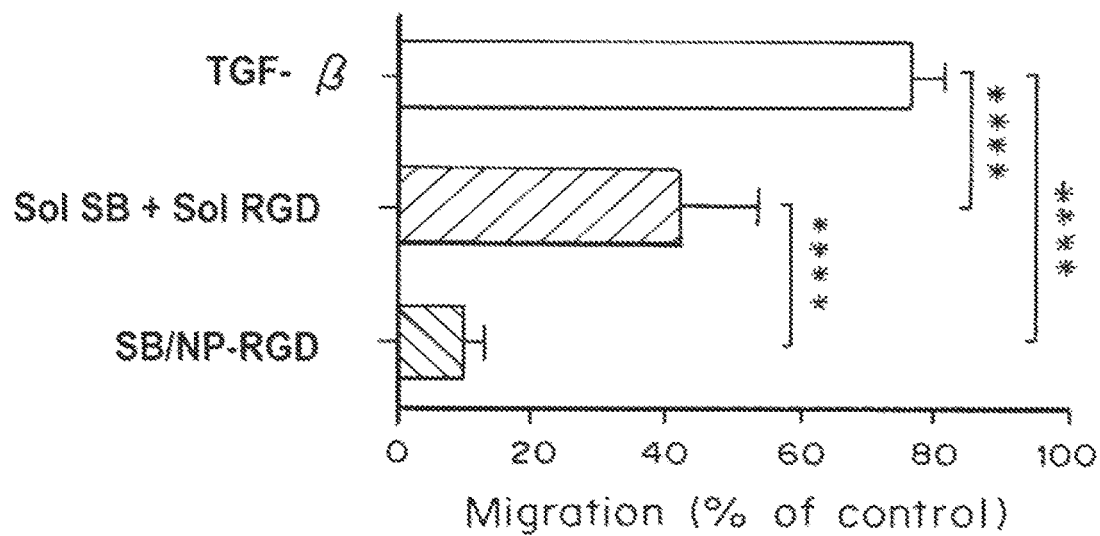
FIG. 10D is a bar graph showing the migration (% of control) of cells treated with TGF-β, soluble SB505124 and RGD, or SB505124 loaded and RGD decorated nanoparticles. Cancer cells (B16F10 melanoma cell line) known to transition from endothelial to mesencyhmal phenotypes (EMT) were assayed here in the presence of TGF-b and with the addition of PLGA-PEG NP loaded with the TGF-b inhibitor and directed to cancer cells overexpressing integrins.

To test potential reduction in cell migration with TGF-β inhibition, a scratch assay (FIG. 10C) and Spheroid formation assay (FIG. 10D) were used. In the former instance, cells were plated in a well and a region was scraped with a pipette tip at t=0. After 24 hours we compared cell migration in the scraped region in the presence of (1) TGF-β, (2) a mixture of SB505124, or (3) PLGA nanoparticles carrying RGD on the surface and loaded with SB505124. Reduction in cancer cell migration was plotted as a wound area ratio (cell free area after 24 hrs/cell free area at 0 hrs) (FIG. 10C). Similar effects were observed in an in vitro spheroid formation assay where we observed that synergistic targeting with RGD and SB505124 facilitated enhanced reduction in spheroid formation (FIG. 10D). These studies demonstrated that co-localized paracrine delivery of RGD and SB505124 strongly inhibited cancer cell migration and support the concept that that nanoparticle-based targeting with RGD further augments the anti-metastatic effect of a TGF-β inhibitor by promoting retention in the tumor microenvironment.

Example 8

Antitumor Effects of TGF-β Inhibitor Losartan in Combination with RGD Peptide

Materials and Methods

Materials were as described above in Example 6. Here Losartan was used instead of SB505124 at the same concentration.

Results

Figure 11A:
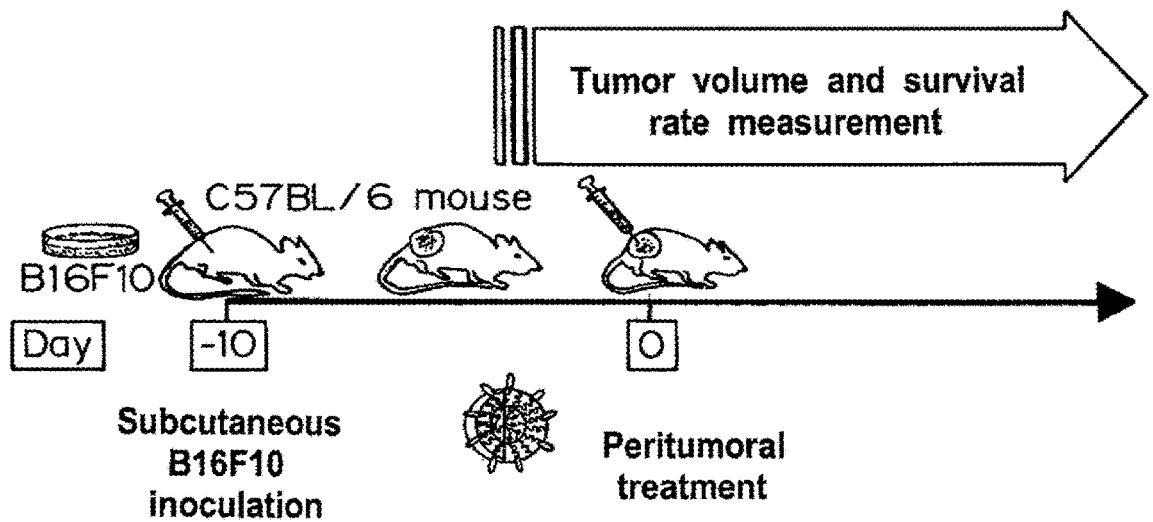
FIG. 11A is a diagram illustrating a mouse tumor model used in the Examples below. B16F10 melanoma tumor cells were injected into the tail vein of C57BL/6 mice on day −10. On day 0, mice were injected IV with losartan and RGD in solution or with one or both agents loaded onto PLGA-PEG nanoparticles. Mice were later sacrificed and tumor nodules were counted.
Figure 11B:
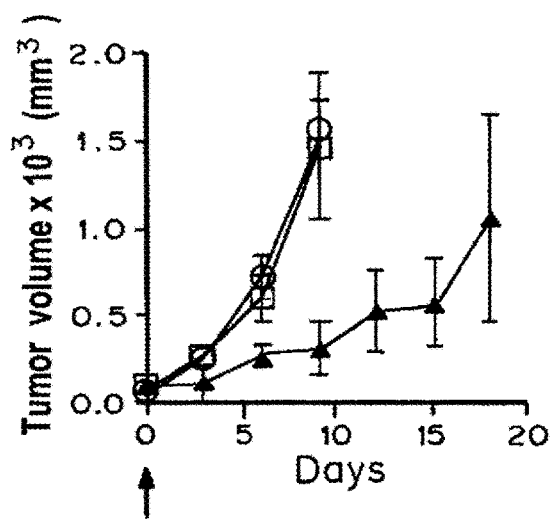
FIG. 11B is a line graph showing tumor volume×$10^3$ (mm$^3$) over time in animals treated with soluble losartan and RGD (Sol Los+Sol RGD (-○-), losartan loaded nanoparticles (Los/NP -Δ-), or losartan loaded and RGD decorated nanoparticles (Los/NP-RGD (-▲-)) according to the assay of FIG. 11A.
Figure 11C:
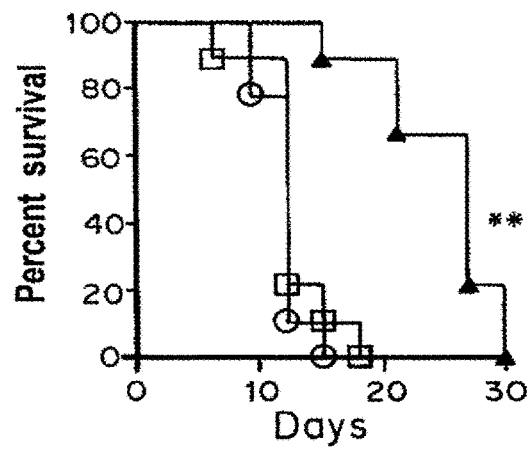
FIG. 11C is a Kaplan-Meier survival curve showing the percent survival over time of mice treated with soluble losartan and RGD (Sol Los+Sol RGD (-○-), losartan loaded nanoparticles (Los/NP -Δ-), or losartan loaded and RGD decorated nanoparticles (Los/NP-RGD (-▲-)) according to the assay of FIG. 11A.

The effect of RGD peptide was also tested in combination with Losartan. Losartan, best known as an angiotensin II receptor antagonist, also down-regulates TGF-β (Guo, et al., *Zhonghua Nei Ke Za Zhi*, 42:403-8 (2003)). FIGS. 11A-11C demonstrates that when C57BL/6 mice were injected with B16F10 melanoma cells followed by (1) empty nanoparticles, (2) soluble Losartan plus soluble RGD, (3) nanoparticles loaded with Losartan, or (4) nanoparticles loaded with Losartan plus RGD, the nanoparticles loaded with Losartan plus RGD were far more effective than any of the other treatments in reducing tumor growth and in prolonging survival of the tumor-bearing mice.

Example 9

Nanoparticles Encapsulating IL-12 Stimulate Antigen-specific CD4+ T Cells

Materials and Methods

Methods for making PLGA nanoparticles decorated with avidin and encapsulating IL-12 are identical to Example 3. IL-12 was used at a concentration of 100 ug/ml per 100 mg of PLGA. We use biotinylated peptide/MHC II specific for the ovalbumin peptide.

Results

One way to promote the development of a more durable cytotoxic T cell response is through CD4+ T cell help. CD4+ T cells have previously been shown to rescue exhausted cytotoxic T cells and fully restore their function in vivo (Aubert, et al., *Proc Natl Acad Sci*, 108:21182-21187 (2011)). CD4+ T cell help can be provided in the form of CD40-CD40L interactions to both dendritic cells and cytotoxic T cells, thus priming CD8+ anti-tumor responses in an indirect and direct manner (Nesbeth, et al., *Journal of immunology*, 184:5654-5662 (2010), Shafer-Weaver, et al., *Cancer Research*, 69:6256-626 (2009)). In addition to this CD4+ T cells can also activate natural killer cells and macrophages to promote the arrest of cancer cell growth (Corthay, *Immunity*, 22, 371-383 (2005)). Perez-Diez, A., *Blood*. 109:5346-5354 (2007). Braumuller, et al., *Nature*. 494:361-365 (2012)). Furthermore, CD4+ T cells can also direct killing towards tumor cells that have down-regulated MHC-I thus avoiding cytotoxic T cell destruction via interaction with MHC-II molecules that can be upregulated on certain solid tumors. It has also been shown that transfer of tumor-specific CD4+ T cells have produced clinically durable responses in a metastatic melanoma model (Hunder, et al., *The New England journal of medicine*, 358, 2698-2703 (2008), Kahn, *Journal of immunology*, 146:3235-3241 (1991)). More importantly, the transferred CD4+ T cells promoted T cell responses against non-cognate tumor antigens.

Figure 12:
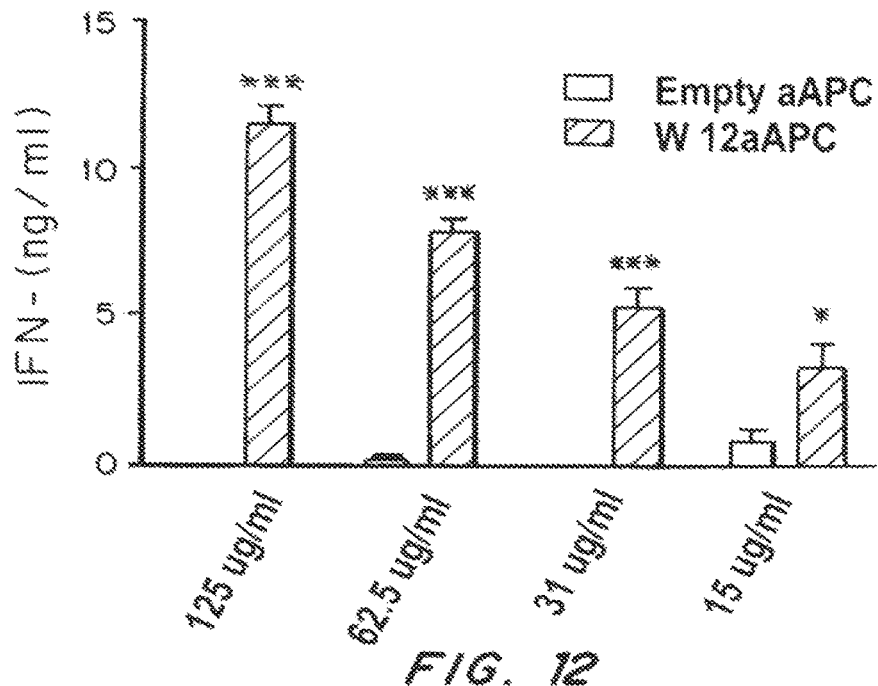
FIG. 12 is a bar graph showing IFNγ (ng/ml) levels following treatment of isolated CD4+ OT-II (Ova Specific) cells with either empty (open bars) or IL-12 encapsulating PLGA nanoparticles (closed bars) and displaying MHC-11 Ova-presenting complexes at varying concentrations (125 μg/ml, 62.5 μg/ml, 31 μg/ml, 15 μg/ml) for 4 days.

One of the driving factors in the differentiation of CD4+ T cells is the cytokine milieu, and IL-12 plays a role in promoting the differentiation of Th1 CD4+ T cells. Experiments were designed to test if particles encapsulating IL-12 and presenting MHC-II peptide complexes or ligands targeting polyclonal CD4 T cells would promote the differentiation of Th1 CD4+ T cells from a naive population. IL-12 can be efficiently encapsulated into PLGA and nanolipogel nanoparticles. CD4+ T cells treated with IL-12 encapsulating nanoparticles secreted significantly more IFN gamma than cells incubated with empty nanoparticles (FIG. 12). The levels of IL-4 secreted by these cells were below the detection limits of the assay indicating that these are Th1 CD4+ T cells. In addition, the nanoparticles encapsulating IL-12 promoted the upregulation of CD44, CD25 and CD27 expression compared to the starting naive population and cells treated with empty nanoparticles.

Figure 13A:
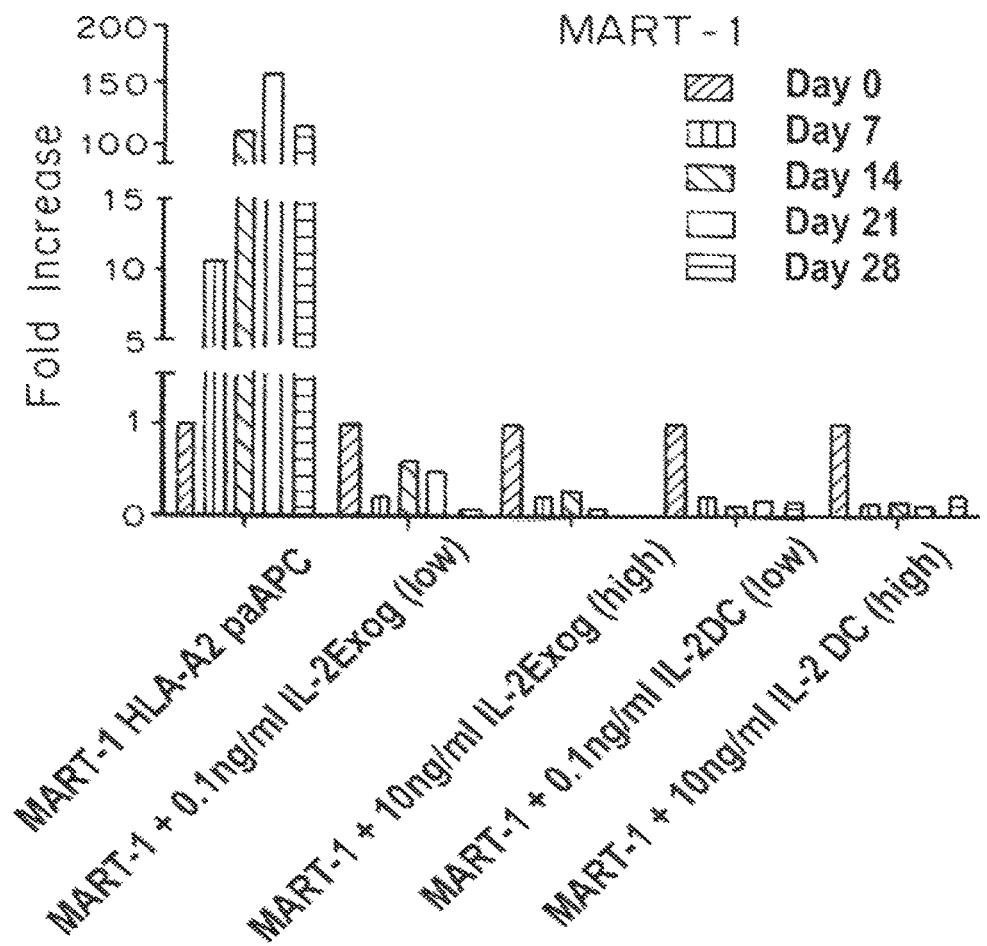
FIG. 13A is a bar graph showing the fold-increase of CD8+ T cells isolated from human PBLCs and treated with PLGA nanoparticles containing the melanoma antigen MART-1 in the context of HLA-A2 compared to soluble IL-2 (0.1 ng/ml or 10 ng/ml) plus MART-1 antigen or IL-2 (0.1 ng/ml or 10 ng/ml) plus dendritic cells that had been pulsed with the MART antigen. The results for each treatment group are shown at days 0, 7, 14, 21, and 28 (from left to right).

The level of MHC-II Ova-presenting complexes on the surface of our IL-12 encapsulated nanoparticles was titrated and the subsequent CD4 T cell response was compared to cells exposed to empty nanoparticles. Using cell trace indo violet it was determined that a greater percentage of CD4+ OT-II cells incubated with the nanoparticles encapsulating IL-12 had proliferated. In addition, these cells were more highly activated than CD4+ T cells as indicated by their expression of higher levels of CD25 and CD44 and the secretion of significantly higher levels of Interferon gamma (FIG. 13A). In conclusion, the encapsulation of the IL-12 in the CD4 targeted nanoparticles boosts the responsiveness and activation of CD4+ T cells.

Example 10

Immunological Mechanisms of Antitumor Effects of Nanolipogels

Figure 13B:
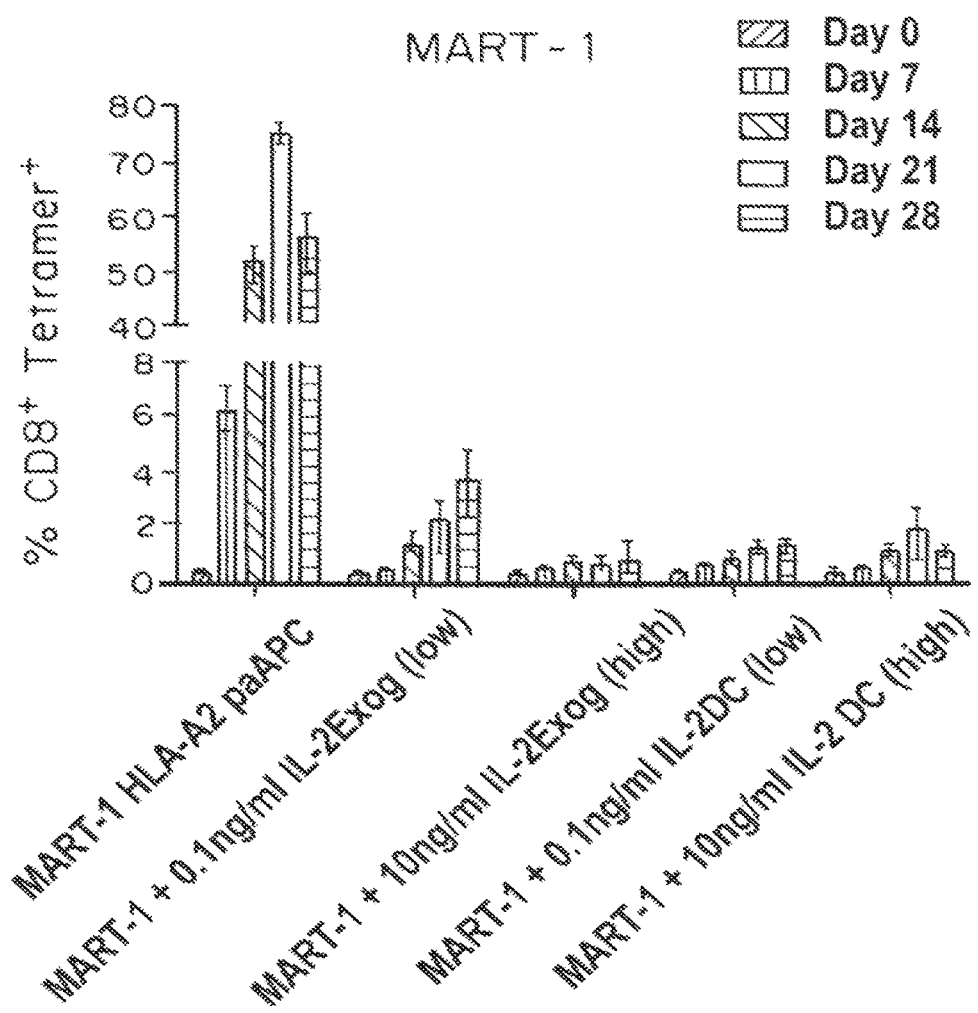
FIG. 13B is a bar graph showing the % tetramer-positive CD8+ T cells following treated with nanoparticles containing the melanoma antigen MART-1 in the context of HLA-A2 compared to soluble IL-2 (0.1 ng/ml or 10 ng/ml) plus MART-1 antigen or IL-2 (0.1 ng/ml or 10 ng/ml) plus dendritic cells that had been pulsed with the MART antigen. The results for each treatment group are shown at days 0, 7, 14, 21, and 28 (from left to right).

To test the ability to use nanoparticles to expand a tumor-antigen-specific T-cell population that could exhibit antitumor effects nanoparticles containing the melanoma antigen MART-1 in the context of HLA-A2 were generated and presented to CD8+ T cells isolated from human pBLs (FIGS. 13A-13B). As shown in FIG. 13A, these nanoparticles were very effective in expanding the T cell population during 28 days in culture, with a maximum increase of approximately 150-fold after 21 days in culture. The expansion was far more pronounced than that obtained by exposing the T-cell cultures to soluble IL-2 plus MART-I antigen or to IL-2 plus dendritic cells that had been pulsed with the MART antigen (FIG. 13A). From day 14 of culture and beyond, the majority of T cells in the cultures treated with MART-loaded nanoparticles formed tetramers upon exposure to MART (FIG. 13B), indicating that the expanded population of T-cells was indeed largely antigen-specific.

Example 11

Losartan/IL-2 Nanolipogels are an Adjuvant that Enhance the Potency of Anti-PD1 and Anti-CTLA4 Therapy Materials and Methods For the in vivo study, mice were housed in autoclaved micro-isolator cages that were placed in a positive pressure containment rack and maintained according to an approved protocol. The mice were randomly assigned to experimental and control groups of 6-8 animals each. B16F10 melanoma cells were cultured as follows: B16F10 melanoma cells were cultured in DMEM media with 10% FBS. After reaching confluence, the cells were detached using trypsin-EDTA, and $2 \times 10^5$ cells were injected intravenously (Tail vein i.v. injection of B16F10 (200,000 cells/50 uL) (Gorelik et al., Nat Med., 7(10):1118-22 (2001)).

Treatment was initiated 7-10 days later with each dose consisting of 5 mg nanolipogels administered intravenously via tail vein injection. Anti-CTLA4 and anti-PD1 were administered IP at the dose schedule shown in the table.

In vivo species—metastasis model
    C57BL/6 mouse (groups 1-10)
Treatments
    i.v. (group 10)
Schedule
    Dose×(number of repeats)
"IMM1" in this Example, and Table 1, FIG. 14 and the description associated therewith, refers to nanolipogels ("NLG") loaded with both IL-2 and Losartan. The nanplipogels have the same polymer and lipid composition as the nanolipogels described in the Examples above. "PD1" in this Example, and Table 1, FIG. 14 and the description associated therewith, refers to an antagonist anti-PD-1 antibody.

Figure 14:
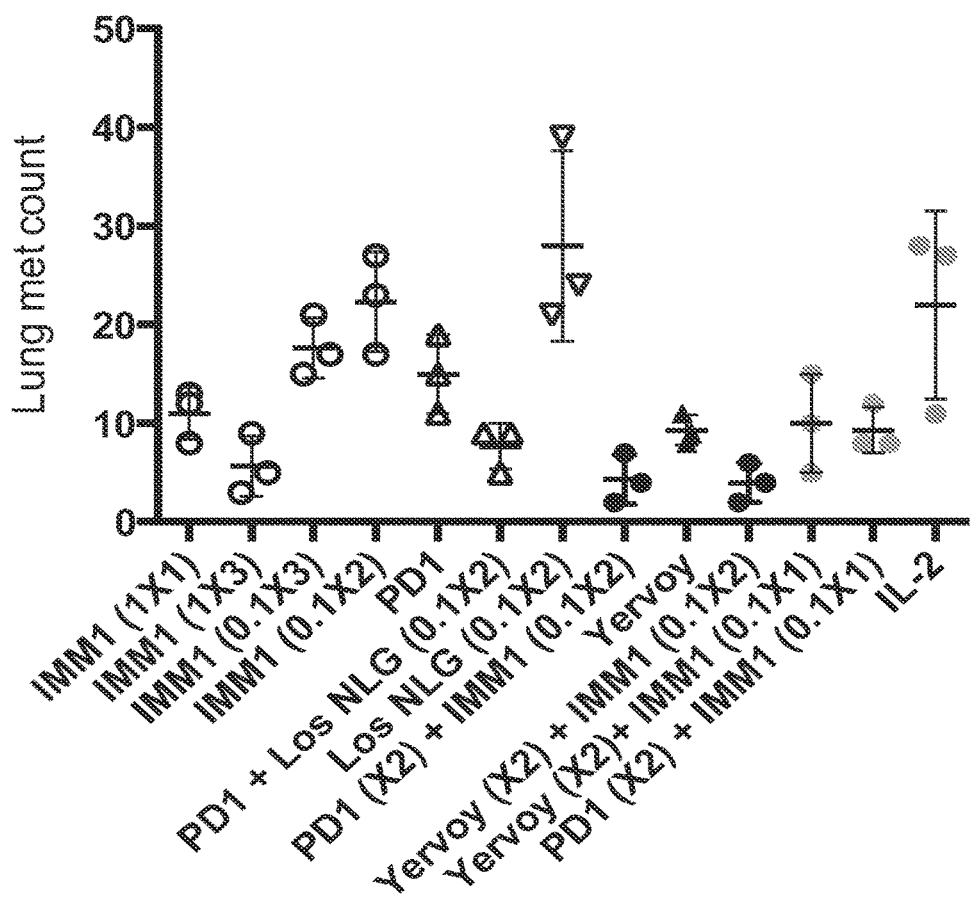
FIG. 14 is a scatter plot showing the effect of different treatment combination and regimens tested on B16F10 murine melanoma in a mouse metastasis model. "IMM 1" refers to nanolipogels loaded with losartan and IL-2; "PD1" refers to antagonistic anti-PD-1 antibody; "Yervoy" refers to antagonistic anti-CTLA4 antibody; "Los-NLG" refers to nanolipogels loaded with losartan, "IL-2" refers to free or soluble IL-2.

"Yervoy" in this Example, and Table 1, FIG. 14 and the description associated therewith, refers to an antagonist anti-CTLA4 antibody.

TABLE 1

Treatment Regimen for Groups 1-12

| Group | Drug | N | Dose | Drug Schedule | Cycle |
|---|---|---|---|---|---|
| 1 | IMM1 | 10* | 5 mg | 7, 14, 21, 28, 35 | |
| 2 | IMM1 | 10* | 5 mg | 7, 10, 13, 16, 19 | |
| 3 | IMM1 | 5 | 5 mg | 7, 10, 13, 16, 19 34, 37, 40, 43, 46 | Repeat once more after 2 weeks |
| 4 | IMM1 | 8** | 0.5 mg | 7, 10, 13, 16, 19 | |
| 4a | IMM1 | 2** | 0.5 mg | 7, 10 | |
| 5 | PD1 | 5* | 100 ug | Day 7 and 10 | |
| 6 | PD1 + LosNLG | 5* | 100 ug/0.5 mg | Day 7 and 10 | |
| 7 | LosNLG | 5* | 0.5 mg | Day 7 and 10 | |
| 8 | PD1 + IMM1 | 5* | 100 ug/0.5 mg | Day 7 and 10 | |
| 9 | Yervoy | 5* | 100 ug | Day 7 and 10 | |
| 10 | Yervoy + IMM1 | 5* | 100 ug/0.5 mg | Day 7 and 10 | |
| 11 | Yervoy + 1MM1 | 5* | 100 ug/0.5 mg | Day 7 and 10 for mAb and day 7 for IMM1 | |
| 12 | PD1 + IMM1 | 5* | 100 ug/0.5 mg | Day 7 and 10 for mAb and day 7 for IMM1 | |

*sacrifice 3 mice for lung mets count, liver weights, take blood for TCR sequencing, and CBC, fix lung tissue and stain for tumor and T cells.
**Sacrifice 2 mice for lung mets count, liver weights, take blood for TCR sequencing, and CBC, fix lung tissue and stain for tumor and T cells.
mAb given IP on day 7 and 10.

Groups 1-4 have a survival component in addition to a subset being sacrificed at day 14 for blood, tumor and tissue analyses.
Groups 5-12 are all sacrificed at day 14 for blood, tumor and tissue analyses.

Results

The data from the experiment, illustrated in FIG. 14, demonstrates two important points. (1) The frequency and dose can be important for therapeutic function of IMM 1 (Losartan-IL2) in nanolipogels alone. For example, IMM-1 administered three times at the highest dose lowers the number of metastatic lesions greater than a 10 fold decreased dose administered at the same frequency. (2) It also shows that anti-PD1 and anti-CTLA4 function more than additively with IMM 1 and/or that IMM-1 adjuvenates or enhances the therapeutic response of those antibodies. For example, IMMI administered twice at a 10 fold lower dose and anti-PD1 alone have a higher lung met count compared to the administration of both agents (therapeutic more than additive effect). Same applies for the anti-CTLA4 (Yervoy).

---

We claim:

1. A nanoparticulate composition comprising:
   a) a delivery vehicle selected from the group consisting of: a nanolipogel comprising a polymeric core and a lipid shell; a biodegradable polymeric particle; and a liposome; and
   b) a cytokine and a TGFβ inhibitor each loaded into, attached to the surface of, and/or enclosed within the delivery vehicle;
   wherein the TGFβ inhibitor is losartan or a pharmaceutically acceptable salt thereof or a 5-carboxylic acid metabolite thereof, and the cytokine is interferon gamma (IFN-γ).

2. The nanoparticulate composition of claim 1, wherein the cytokine is IFN-γ and the TGFβ inhibitor is losartan.

3. The nanoparticulate composition of claim 1, wherein the delivery vehicle is a nanolipogel comprising a polymeric core formed of non-crosslinkable polymers.

4. The nanoparticulate composition of claim 1, wherein the delivery vehicle is a nanolipogel comprising a polymeric core formed of one or more crosslinkable polymers.

5. The nanoparticulate composition of claim 4, wherein the polymers in the polymeric core are cross-linked by way of one or more photo-polymerizable groups.

6. The nanoparticulate composition of claim 1, wherein the delivery vehicle is a nanolipogel comprising a polymeric core formed of a block copolymer containing one or more poly(alkylene oxide) segments selected from polyethylene glycol, polypropylene, 1,2-glycol, poly(propylene oxide) and/or polypropylene 1,3-glycol segments; and/or one or more aliphatic polyester segments selected from polylactic acid (PLA), polyglycolic acid (PGA), and/or polylactide-coglycolide (PLGA) segments.

7. The nanoparticulate composition of claim 6, wherein the block copolymer is a tri-block copolymer containing a central poly(alkylene oxide) segment and adjoining aliphatic polyester segments attached to either end of the central poly(alkylene oxide) segment.

8. The nanoparticulate composition of claim 6, wherein the polymeric core further comprises one or more photo-polymerisable groups.

9. The nanoparticulate composition of claim 1, wherein the delivery vehicle is a nanolipogel comprising a polymer matrix core containing one or more host molecules dispersed within or covalently bound to the polymeric matrix, and a lipid shell.

10. The nanoparticulate composition of claim 9, wherein the one or more host molecules are selected from the group consisting of polysaccharides, cyclodextrins, cryptands, cryptophanes, cavitands, crown ethers, dendrimers, catenanes, polycatenanes, carcerands, spherands, carbon nanotubes, fullerenes, inorganic phosphates, and silica.

11. The nanoparticulate composition of claim 1, wherein the delivery vehicle is a nanolipogel comprising a polymeric core containing one or more host molecules and a lipid shell; and wherein each of the cytokine and TGFβ inhibitor is dispersed within the polymeric core, dispersed within the lipid shell, and/or attached to the lipid shell.

12. The nanoparticulate composition of claim 11, wherein the TGFβ inhibitor is associated with a host molecule and the cytokine is dispersed within the polymeric core.

13. The nanoparticulate composition of claim 9, wherein the one or more host molecules comprise cyclodextrin which is unfunctionalized or is functionalized with one or more reactive functional groups that react with the polymeric matrix core and/or with one or more reactive functional groups that modify the solubility of the cyclodextrin.

14. The nanoparticulate composition of claim 1, wherein the delivery vehicle is a nanolipogel comprising a lipid shell composed of a mixture of a phospholipid, a PEG-ylated phospholipid, and cholesterol.

15. The nanoparticulate composition of claim 1, wherein the delivery vehicle is a polymeric nanoparticle formed of one or more polymers selected from polymers of hydroxyacids, and copolymers of the hydroxyacids with polyethylene glycol, polyanhydrides, poly(ortho)esters, polyurethanes, poly(butyric acid), poly(valeric acid), poly(lactide-co-caprolactone), and blends and copolymers thereof.

16. The nanoparticulate composition of claim 1, wherein the delivery vehicle is decorated with a target moiety selected from the group consisting of RGD peptide, a CD40 agonist, an anti-CD40 antibody or fragment thereof, a T cell receptor (TCR), an IL-15/IL-15Rα complex, and a moiety that targets antigen presenting cells.

17. The nanoparticulate composition of claim 16, wherein the TCR is a T cell receptor that recognizes the p53 antigen.

18. The nanoparticulate composition of claim 1, further comprising at least one additional active agent which is an immune modulator or a chemotherapeutic agent, wherein the at least one additional active agent is not loaded into, attached to the surface of or enclosed within said delivery vehicle.

19. The nanoparticulate composition of claim 18, wherein the immune modulator is an immune response stimulating agent; an agent that blocks immune suppression; or an agent that targets tumor checkpoint blockade or costimulatory molecules.

20. The nanoparticulate composition of claim 19, wherein the immune response stimulating agent is a PD-1 antagonist, a CTLA4 antagonist or a combination thereof, or wherein the chemotherapeutic agent is doxorubicin.

* * * * *

UNITED STATES PATENT AND TRADEMARK OFFICE
CERTIFICATE OF CORRECTION

PATENT NO. : 10,751,291 B2
APPLICATION NO. : 15/860888
DATED : August 25, 2020
INVENTOR(S) : Tarek M. Fahmy and Brian Horsburgh It is certified that error appears in the above-identified patent and that said Letters Patent is hereby corrected as shown below:

In the Specification

The sentence at Column 3, Line 63 through Column 4, Line 2 should read as follows:
FIG. 2 is a line graph showing the relative tumor volume (mm3) in nude mice over time (days) following subcutaneous A375C15N (p53+HLA-A2/Human melanoma) xenograft tumor establishment and subsequent treatment with PBS, TCR-particle (IL-2 encapsulated) nanolipogels, or TCR/IL-2 (soluble p53-specific scTCR/IL-2 fusion protein (Altor 801, Altor Biosciences, Miramar, Fla.)) nanoparticles.

The sentence at Column 4, Lines 31-37 should read as follows:
Ova mice (mice injected with a derivative melanoma line, whose cells carry an ovalbumin surface antigen (OVA)) treated with PBS (-○-), nanoparticles only (-●-), IL-15/IL-15Rα complex only (--□--), IL-15/IL-15Rα complex decorated PLGA nanoparticles (-□-), and IL-15/IL-15Rα complex decorated nanoparticles encapsulating Ova (-■-).

The sentence at Column 5, Lines 41-46 should read as follows:
FIG. 12 is a bar graph showing IFNγ (ng/ml) levels following treatment of isolated CD4+ OT-II (Ova Specific) cells with either empty (open bars) or IL-12 encapsulating PLGA nanoparticles (closed bars) and displaying MHC-II Ova-presenting complexes at varying concentrations (125 μg/ml, 62.5 μg/ml, 31 μg/ml, 15 μg/ml) for 4 days.

The sentence at Column 9, Lines 11-13 should read as follows:
Nanolipogels can be constructed to incorporate a variety of active agents that can subsequently be released in a controlled fashion.

The sentence at Column 14, Lines 56-59 should read as follows:
Suitable TAP lipids include, but are not limited to, DOTAP (dioleoyl-), DMTAP (dimyristoyl-), DPTAP (dipalmitoyl-), and DSTAP (distearoyl-).

Signed and Sealed this
Twenty-sixth Day of July, 2022

Katherine Kelly Vidal
*Director of the United States Patent and Trademark Office*

CERTIFICATE OF CORRECTION (continued)
U.S. Pat. No. 10,751,291 B2

The sentence at Column 16, Lines 3-7 should read as follows:
In preferred embodiments, the lipid shell is formed froma mixture of phospholipid, such as phosphatidyl choline (PC), a PEGylated phospholipid, such as 1,2-distearoyl-sn-glycero-3-phosphoethanolamien-N-[amino(polyethylene glycol)-2000] (DSPE-PEG), and cholesterol.

The sentence at Column 19, Lines 23-29 should read as follows:
Exemplary cytokines include, but are not limited to, interleukins (e.g., IL-1, IL-2, IL-4, IL-5, IL-6, IL-7, IL-12, IL-15, etc.), interferons (e.g., interferon-• ), macrophage colony stimulating factor, granulocyte colony stimulating factor, tumor necrosis factor, Leukocyte Inhibitory Factor (LIF), chemokines, SDF-1• , and the CXC family of cytokines.

The sentence at Column 21, Lines 55-60 should read as follows:
Tumor growth is monitored and, beginning approximately 7 days later, when the tumor reaches 0.5 mm2 in area, animals are subjected to a course of peritumoral injections of 5 μg of nanoparticles (a) loaded with IL-2 and Losartan; or as controls, (b) blank particles (similar to assays described in the Examples below).

The sentence at Column 26, Lines 14-28 should read as follows:
Bacterial antigens can originate from any bacteria including, but not limited to Actinomyces, Anabaena, Bacillus, Bacteroides, Bdellovibrio, Bordetella, Borrellia, Campylobacter, Caulobacter, Chlamydia, Chlorobium, Chromatium, Escherichia, Francisella, Halobacterium, Heliobacter, Haemophilus, Hemophilus influenza type B (HIB), Hyphomicrobium, Legionella, Leptspirosis, Listeria, Meningococcus A, B, and C, Methanobacterium, Micrococcus, Myobacterium, Mycoplasma, Myxococcus, Neisseria, Nitrobacter, Oscillatoria, Prochloron, Proteus, Pseudomonas, Phodosprillum, Staphylococcus, Streptococcus, Streptomyces, Sulfolobus, Thermoplasma, Thiobacillus, and Treponema, Vibrio, and Yersinia.

The sentence at Column 26, Lines 30-37 should read as follows:
Parasite antigens can be obtained from parasites such as, but not limited to, an antigen derived from Cryptococccus neoformans, Histoplasma capsulatum, Candida albicans, Candida tropicalis, Nocardia asteroids, Rickettsia rickettsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vacinalis and Schistosoma mansoni.

The sentence at Column 27, Line 48 through Column 28, Line 8 should read as follows:
Representative anti-cancer agents include, but are not limited to, alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and decetaxel and vinca alkaloids such as vincristine, vinblastine, vinorelbine, and vindesine), antracyclins (including doxorubicin, daunorubicin, valrubicin, idarubicin, and epirubicin, as well as actinomycins such as actinomycin D), cytotoxic antibiotics (including mitomycin, plicamycin, and bleomycin), topoisomerase inhibitors (including camptothecins such as camptothecin, irinotecan, and topotecan as well derivatives of epipodophyllotoxins such as amsacrine, etoposide phosphate, and teniposide), antibodies to vascular endothelial growth factor (VEGF) such as becacizumab (AVASTIN®), other anti-VEGF compounds; thalidomide (THALOMID®) and

CERTIFICATE OF CORRECTION (continued)
U.S. Pat. No. 10,751,291 B2 derivatives thereof such as lenalidomide (REVLIMID®); endostatin; angiostatin; receptor tyrosine kinase (RTK) inhibitors such as sunitinib (SUTENT®); tyrosine kinase inhibitors such assorafenib (Nexavar®), erlotinib (Tarceva®), pazopanib, axitinib, and lapatinib; transforming growth factor-α or transforming growth factor-β inhibitors, and antibodies to the epidermal growth factor receptor such as panitumumab (VECTIBIX®) and cetuximab (ERBITUX®).

The subtitle at Column 36, Line 20 should read as follows:
d. Spray-Drying.

The sentence at Column 36, Lines 24-29 should read as follows:
Typical process parameters for a mini-spray drier (Buchi) are as follows: polymer concentration=0.04 g/mL, inlet temperature=-24° C., outlet temperature=13-15° C., aspirator settings=15, pump setting=10 mL/minute, spray flow=600 Nl/hr, and nozzle diameter=0.5 mm.

The sentence at Column 41, Lines 13-34 should read as follows:
Representative infections that can be treated, include but are not limited to infections caused by microorganisms including, but not limited to, Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobarcterium, Heliobacter, Haemophilus, Haemophilus influenza type B (HIB), Hyphomicrobium, Legionella, Leptspirosis, Listeria, Meningococcus A, B, and C, Methanobacterium, Micrococcus, Myobacterium, Mycoplasma, Myxococcus, Neisseria, Nitrobacter, Oscillatoria, Prochloron, Proteus, Psuedomonas, Phodospirillum, Rickettsia, Salmonella, Shigella, Spirillum, Spirochaeta, Staphylococcus, Streptococcus, Streptomyces, Sulfolobus, Thermoplasma, Thiobacillus, and treponema, Vibrio, Yersinia, Cryptococcus neoformans, Histoplasma capsulatum, Candida albicans, Candida tropicalis, Nocordia asteroids, Rickettsia rickettsia, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis and Schistosoma mansoni.

The sentence at Column 44, Lines 37-39 should read as follows:
The proinflammatory cytokine can be IL-2 or IFNγ and the TGF-β inhibitor can be SB505124 or losartan.

The sentence at Column 46, Lines 43-59 should read as follows:
As discussed above with respect to immune response stimulating agents, it is likewise believed that when one or more chemotherapeutic agents such as doxorubicin is co-administered in combination with nanolipogels or particles loaded or associated with proinflammatory cytokine such as IL-2 and/or a TGF-β inhibitor such as losartan, (1) the chemotherapeutic agent(s) can be administered at a lower dose; (2) the chemotherapeutic agent(s) will exhibit reduced side effects or toxicity to the subject; (3) the chemotherapeutic agent will exhibit enhanced potency, and/or (4) the result achieved by the chemotherapeutic agent in combination with the loaded nanolipogels or particles will have a greater than additive effect on the subject when compared to administered the chemotherapeutic agent(s) without the loaded nanolipogels or particles; or administering the loaded nanolipogels or particles in the absence of the chemotherapeutic agent(s).

CERTIFICATE OF CORRECTION (continued)
U.S. Pat. No. 10,751,291 B2

The sentence at Column 47, Lines 38-43 should read as follows:
However, at the end of the study period mean tumor volumes in nanoparticle-treated mice were reduced by approximately 70%, even though the amount of IL-2 loaded in nanoparticles was approximately 1000-fold lower compared to the relative IL-2 concentration in the TCR/IL-2 chimeric protein.

The sentence at Column 48, Lines 62-65 should read as follows:
IL-15 heterodimer was reacted at a 1:10 molar ratio with NHS-LC-LC-biotin (Thermo Scientific, Rockford, Ill.) then dialyzed for 48 h in PBS to remove unreacted biotin.

The sentence at Column 49, Lines 41-45 should read as follows:
For subcutaneous tumor studies, female 6-8 week-old C57BL/6 mice were sedated with AErrane (isofluorane; Baxter) and the right hind flank was shaved prior to a subcutaneous injection of 50 μL of the cellular suspension.

The sentence at Column 50, Lines 1-3 should read as follows:
Nanoparticles were decorated with IL-15/IL-15Rα complexes and additionally loaded with endotoxin-free ovalbumin protein.

SEQUENCE LISTING

```
<160> NUMBER OF SEQ ID NOS: 4

<210> SEQ ID NO 1
<211> LENGTH: 22
<212> TYPE: DNA
<213> ORGANISM: Rhesus monkey

<400> SEQUENCE: 1
cccggccact ttcaggagga gg                                                 22

<210> SEQ ID NO 2
<211> LENGTH: 20
<212> TYPE: DNA
<213> ORGANISM: Rhesus monkey

<400> SEQUENCE: 2
gtcctgtctg caccatcctc                                                    20

<210> SEQ ID NO 3
<211> LENGTH: 162
<212> TYPE: PRT
<213> ORGANISM: Homo sapiens

<400> SEQUENCE: 3

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser

<210> SEQ ID NO 4
<211> LENGTH: 267
<212> TYPE: PRT
<213> ORGANISM: Homo sapiens
```

-continued

```
<400> SEQUENCE: 4

Met Ala Pro Arg Arg Ala Arg Gly Cys Arg Thr Leu Gly Leu Pro Ala
1               5                  10                  15

Leu Leu Leu Leu Leu Leu Leu Arg Pro Pro Ala Thr Arg Gly Ile Thr
                20                  25                  30

Cys Pro Pro Pro Met Ser Val Glu His Ala Asp Ile Trp Val Lys Ser
            35                  40                  45

Tyr Ser Leu Tyr Ser Arg Glu Arg Tyr Ile Cys Asn Ser Gly Phe Lys
        50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
        195                 200                 205

Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
            260                 265
```